US012734252B2

(12) United States Patent
Davidson et al.

(10) Patent No.: US 12,734,252 B2
(45) Date of Patent: Sep. 15, 2026

(54) ADENO-ASSOCIATED VIRAL VECTOR VARIANTS

(71) Applicant: The Children's Hospital of Philadelphia, Philadelphia, PA (US)

(72) Inventors: Beverly Davidson, Philadelphia, PA (US); Yonghong Chen, Philadelphia, PA (US); Paul T. Ranum, Philadelphia, PA (US); Xueyuan Liu, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 194 days.

(21) Appl. No.: 18/491,365

(22) Filed: Oct. 20, 2023

(65) Prior Publication Data

US 2024/0100194 A1 Mar. 28, 2024

Related U.S. Application Data

(63) Continuation of application No. 17/778,783, filed as application No. PCT/US2020/061464 on Nov. 20, 2020.

(60) Provisional application No. 63/084,709, filed on Sep. 29, 2020, provisional application No. 62/939,315, filed on Nov. 22, 2019.

(51) Int. Cl.

| | |
|---|---|
| ***A61K 48/00*** | (2006.01) |
| ***A61P 25/00*** | (2006.01) |
| ***C07K 7/06*** | (2006.01) |
| ***C12N 15/86*** | (2006.01) |

(52) U.S. Cl.
CPC .......... *A61K 48/0075* (2013.01); *A61P 25/00* (2018.01); *C07K 7/06* (2013.01); *C12N 15/86* (2013.01); *C12N 2750/14122* (2013.01); *C12N 2750/14143* (2013.01); *C12N 2750/14171* (2013.01)

(58) Field of Classification Search
CPC ..... A61K 48/0075; A61K 48/00; A61P 25/00; A61P 25/28; C07K 7/06; C07K 14/005; C07K 2319/33; C12N 15/86; C12N 2750/14122; C12N 2750/14143; C12N 2750/14171; C12N 2750/14145
See application file for complete search history.

(56) References Cited

U.S. PATENT DOCUMENTS

| | | | | |
|---|---|---|---|---|
| 8,299,215 | B2 | 10/2012 | Davidson et al. | |
| 8,691,948 | B2 | 4/2014 | Davidson et al. | |
| 9,585,971 | B2 * | 3/2017 | Deverman | A61K 38/47 |
| 10,472,650 | B2 | 11/2019 | Davidson et al. | |
| 2004/0031072 | A1 | 2/2004 | La Rosa et al. | |
| 2013/0224836 | A1 | 8/2013 | Muramatsu | |
| 2013/0330335 | A1 | 12/2013 | Bremel et al. | |
| 2017/0029464 | A1 | 2/2017 | Körbelin et al. | |
| 2019/0175763 | A1 | 6/2019 | Shapiro et al. | |

FOREIGN PATENT DOCUMENTS

| | | |
|---|---|---|
| KR | 10-2017-0086537 | 7/2017 |
| KR | 10-2018-0097629 | 8/2018 |
| KR | 10-2019-0034239 | 4/2019 |
| WO | WO2003/052051 | 6/2003 |
| WO | WO2006105392 | 10/2006 |
| WO | WO2012057363 | 5/2012 |
| WO | WO2015/038958 | 3/2015 |
| WO | WO2016/081811 | 5/2016 |
| WO | WO2017/100671 | 6/2017 |
| WO | WO2018/022905 | 2/2018 |
| WO | WO 2018/152333 | 8/2018 |
| WO | WO 2018/209317 | 11/2018 |
| WO | WO 2019/060454 | 3/2019 |
| WO | WO 2019/067840 | 4/2019 |
| WO | WO 2019/222329 | 11/2019 |
| WO | WO2020/014471 | 1/2020 |
| WO | WO 2021/163556 | 8/2021 |

OTHER PUBLICATIONS

Chekhonin et al., "Targeted Transport of Genetic Material into Brain" *Biootechnology*, 5, 14-23, 2007.
Dalton et al., "Multiple Myeloma" *American Society of Hematology*, 2001, 157-177.
Lundberg et al., "Direct delivery of leptin to the hypothalamus using recombinant adeno-associated virus vectors results in increased therapeutic efficacy", *Nature Biotechnology*, 19, 169-172, 2001.
Muller et al., "Spliceosomal Peptide P140 for Immunotherapy of Systemic Lupus Erythematosus" *Arthritis & Rheumatism*, 58(12):3873-3883, 2008.
Pires et al. "Old and new challenges in Parkinson's disease therapeutics", *Progress in Neurobiology*, 156, 69-89, 2017.
Schwab et al., "Dopamine and Huntington's disease", *Expert Rev. Neurother*, 15(4):445-458, 2015.
Smirnova et al., "Structure of the nervous system", *Human anatomy. Nervous system: educational manual, MSEI named after A.D. Sakharov BSU*, 2018.
Zhou et al., "Mitochondria-homing peptide functionalized nanoparticles performing dual extracellular/intracellular roles to inhibit aminoglycosides induced ototoxicity", *Artificial Cells, Nanomedicine, and Biotechnologyi*, 46(2), 2018.
Zvěřová "Clinical aspects of Alzheimer's disease", *Clinical Biochemistry*, 72, 3-6, 2019.
Chen et al., "Fusion Protein Linkers: Property, design, and functionality", *Advanced Drug Delivery Reviews*, 65, 1357-1369, 2013.
Pham et al., "Chemical approaches to probe and engineer AAV vectors", *Nanoscale*, 16, 13820-13833, 2024.
Singh et al., Protein Engineering Approaches in the Post-Genomic Era, *Current Protein and Peptide Science*, 18, 1-11, 2017.

(Continued)

*Primary Examiner* — Paul J Holland
(74) *Attorney, Agent, or Firm* — pH IP Law

(57) ABSTRACT

Provided herein are targeting peptides and vectors containing a sequence that encodes the targeting peptides that deliver agents to specific substructures in the brain.

19 Claims, 22 Drawing Sheets

Specification includes a Sequence Listing.

(56) References Cited

OTHER PUBLICATIONS

Zhang et al., "Propagated Perturbations from a Peripheral Mutation Show Interactions Supporting WW Domain Thermostability", *Structure*, 26, 1474-1485, 2018.
Chen et al., Molecular signatures of disease brain endothelia provide new sites for CNS-directed enzyme therapy. Nat Med, 2009. 15(10): p. 1215-8.
Chen et al., Overcoming Limitations Inherent in Sulfamidase to Improve Mucopolysaccharidosis IIIA Gene Therapy. Mol Ther, 2018. 26(4): p. 1118-1126.
Deverman et al., Cre-dependent selection yields AAV variants for widespread gene transfer to the adult brain. Nat Biotechnol, 2016. 34(2): p. 204-9.
Hartz et al., Isolation of Cerebral Capillaries from Fresh Human Brain Tissue. J Vis Exp, 2018(139).
Hordeaux et al., The Neurotropic Properties of AAV-PHP.B Are Limited to C57BL/6J Mice. Mol Ther, 2018. 26(3): p. 664-668.
International Preliminary Report on Patentability issued in Patent Application No. PCT/US20/61464, dated May 27, 2022.
International Search Report issued in Patent Application No. PCT/US20/61464, dated Apr. 9, 2021.
Katz et al., AAV gene transfer delays disease onset in a TPP1-deficient canine model of the late infantile form of Batten disease. Sci Transl Med, 2015. 7(313): p. 313ra180.
Keiser et al., Broad distribution of ataxin 1 silencing in rhesus cerebella for spinocerebellar ataxia type 1 therapy. Brain, 2015. 138(Pt 12): p. 3555-66.
Koerber et al., DNA shuffling of adeno-associated virus yields functionally diverse viral progeny. Mol Ther, 2008. 16(10): p. 1703-9.
Matsuzaki et al., Intravenous administration of the adeno-associated virus-PHP.B capsid fails to upregulate transduction efficiency in the marmoset brain. Neurosci Lett, 2018. 665: p. 182-188.
McBride et al., Preclinical safety of RNAi-mediated HTT suppression in the rhesus macaque as a potential therapy for Huntington's disease. Mol Ther, 2011. 19(12): p. 2152-62.
Monteys et al., CRISPR/Cas9 Editing of the Mutant Huntingtin Allele In Vitro and In Vivo. Mol Ther, 2017. 25(1): p. 12-23.
Muller et al., Random peptide libraries displayed on adeno-associated virus to select for targeted gene therapy vectors. Nat Biotechnol, 2003. 21(9): p. 1040-6.
Schaffer & Maheshri, Directed evolution of AAV mutants for enhanced gene delivery. Conf Proc IEEE Eng Med Biol Soc, 2004. 5: p. 3520-3.
Zhong et al., Next generation of adeno-associated virus 2 vectors: point mutations in tyrosines lead to high-efficiency transduction at lower doses. Proc Natl Acad Sci U S A, 2008. 105(22): p. 7827-32.
Extended European Search Report for EP Application No. 20890214.8 dated Dec. 11, 2023, 9 pages.
Lee et al. "Adeno-Associated Virus (AAV) Vectors: Rational Design Strategies for Capsid Engineering", *Curr Opin Biomed Eng.*, 7:58-63, 2018.
Stover et al., "Transduction of the contralateral ear after adenovirus-mediated cochlear gene transfer", *Gene Therapy*, 7, 377-383, 2000.
Office Action for Korean Application No. 10-2022-7021143 dated Sep. 19, 2025; 8 pages, inclusive of machine translation to English.
Büning et al., "Capsid Modifications for Targeting and Improving the Efficacy of AAV Vectors", *Molecular Therapy Methods & Clinical Development*, 12, 248-265, 2019.
Office Action for Canadian Application No. 3,159,113 dated Mar. 24, 2026, 8 pages.
Office Action for Columbian Application No. NC2022/0008507 dated Aug. 8, 2025; 20 pages, inclusive of machine translation to English.
Office Action for Singapore Application No. 11202205339R dated Sep. 19, 2025, 13 pages.

* cited by examiner

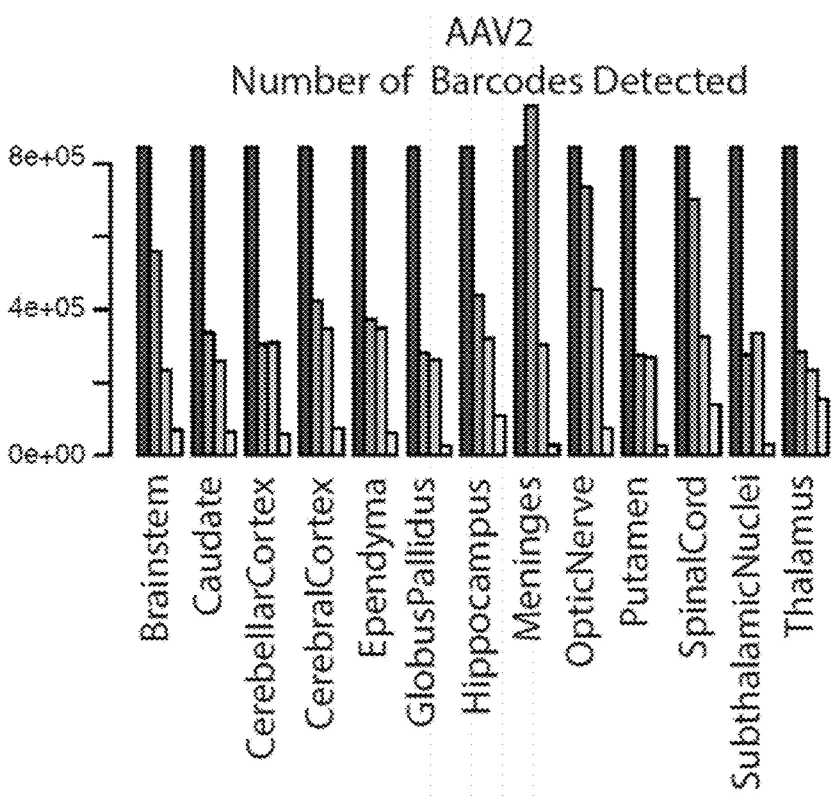
FIG. 4, con't.

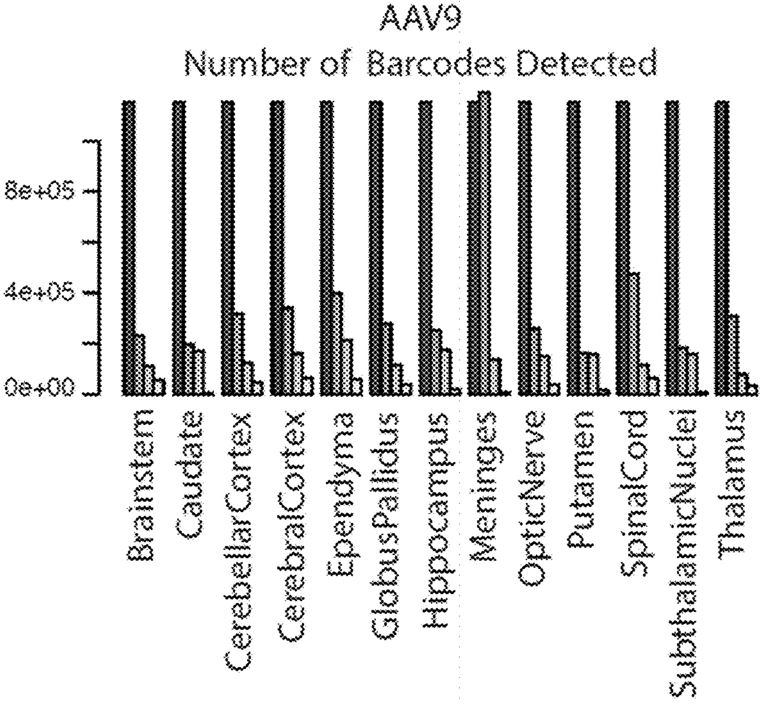
FIG. 4, con't.

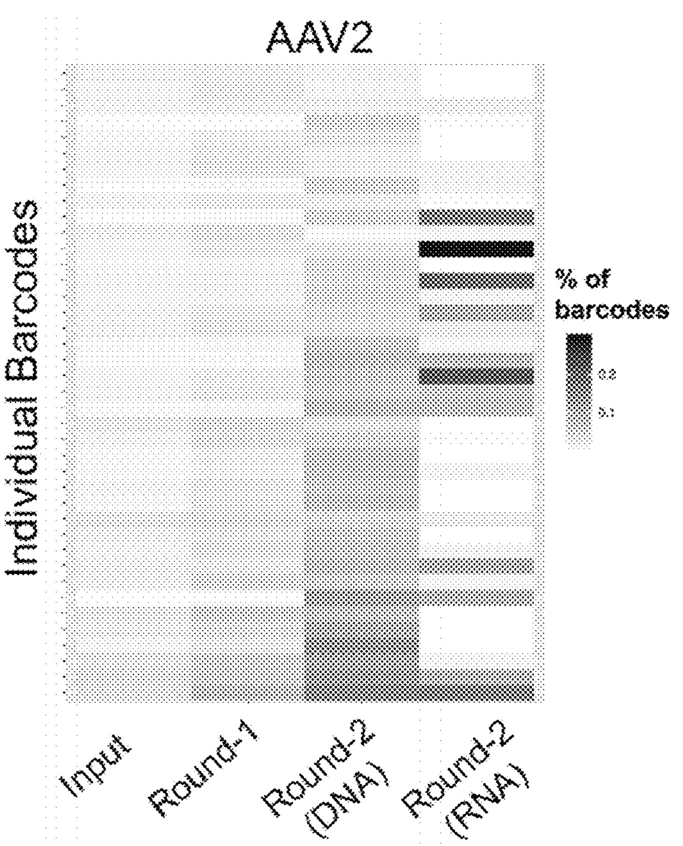
FIG. 5, con't.

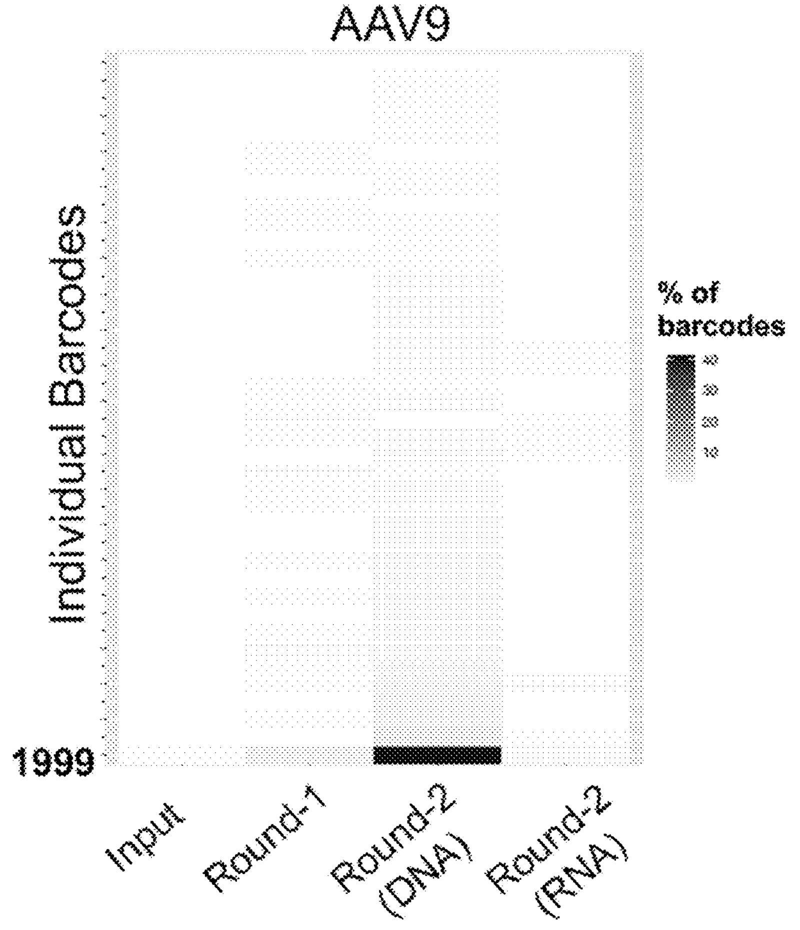
FIG. 5, con't.

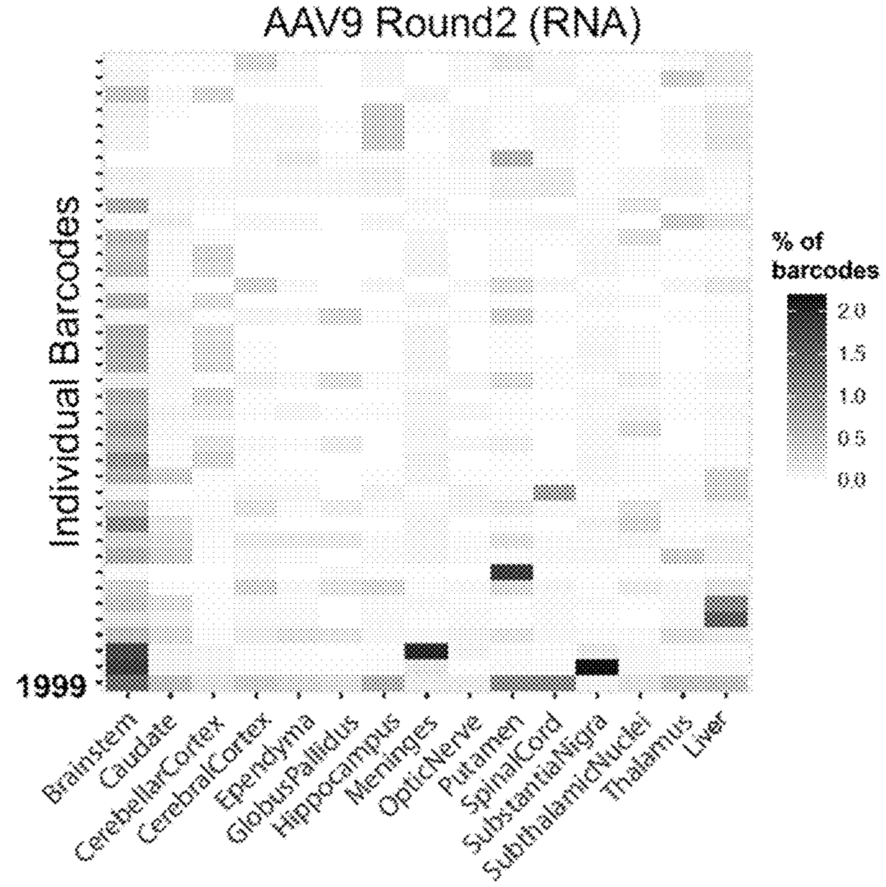
FIG. 6, con't.

AAV-1999
AAV9
FIG. 9A
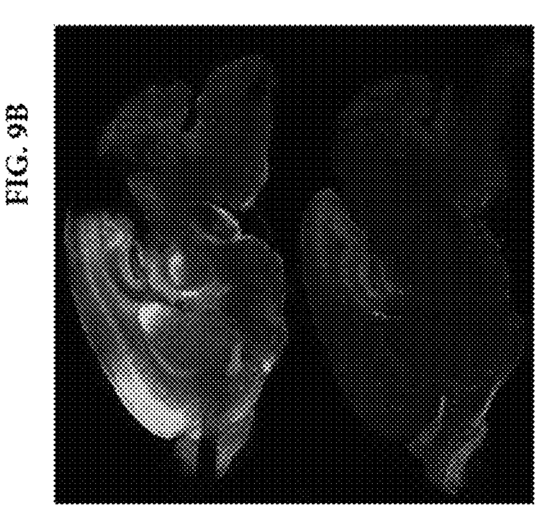
FIG. 9B
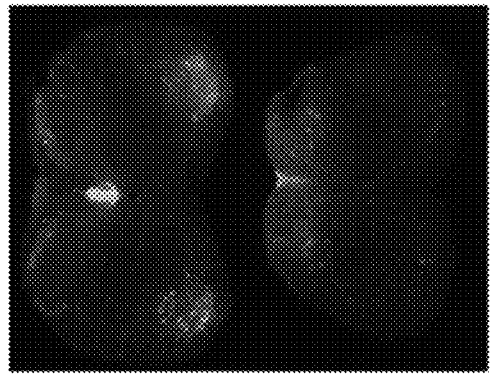
FIG. 9D
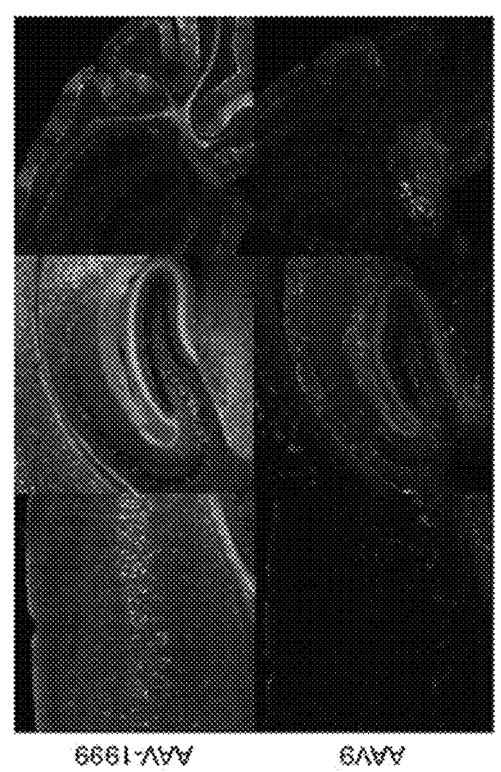
FIG. 9C

ADENO-ASSOCIATED VIRAL VECTOR VARIANTS

REFERENCE TO RELATED APPLICATIONS

This application is a continuation application of U.S. application Ser. No. 17/778,783 filed May 20, 2022 entitled “Adeno-Associated Viral Vector Variants”, which is a national phase application under 35 U.S.C. § 371 of International Application No. PCT/US2020/061464, filed Nov. 20, 2020, which claims benefit of priority to U.S. Provisional Application Ser. No. 62/939,315, filed Nov. 22, 2019, and 63/084,709, filed Sep. 29, 2020, the entire contents of each of which are being hereby incorporated by reference in their entirety.

REFERENCE TO A SEQUENCE LISTING

The instant application contains a Sequence Listing, which has been submitted in ST26 XML format via EFS-Web and is hereby incorporated by reference in its entirety. Said XML copy, created on Oct. 24, 2023, is named CHOPP0038USC1-Sequence-Listing-2.xml and is 184,352 bytes in size.

BACKGROUND

1. Field

The present invention relates generally to the fields of medicine, virology, and neurology. More particularly, it concerns targeting peptides that target delivery of viral vectors to distinct structures in the brain.

2. Description of Related Art

Different strategies have been developed to generate AAV vector variants including rational design and directed evolution. The rational design approach utilizes knowledge of AAV capsids to make targeted changes to the capsid to alter transduction efficiency or specificity, such as tyrosine mutations on the capsid surface for increasing transduction efficiency. The directed evolution approach does not require any knowledge of capsid structure and is done through random mutagenesis, capsid shuffling, or random peptide insertions. These strategies generally use in vitro systems or mice, which are ideal for cell-based or mouse studies, but do not imply translation to the clinic. In fact, no AAV variants target distinct brain structures specifically or efficiently. As such, AAV variants that are able to target distinct primate brain structures are needed.

SUMMARY

Provided herein are viral vectors each comprising a modified capsid, wherein the modified capsid comprises at least one amino acid sequence that targets the viral vector to a distinct brain structure.

In one embodiment, provided are modified adeno-associated virus (AAV) capsid proteins comprising a targeting peptide that targets a viral vector comprising the modified AAV capsid protein to a distinct organ or brain structure, and the targeting peptide is three to ten amino acids in length. In some aspects, the modified AAV capsid proteins are modified AAV1 capsid proteins, modified AAV2 capsid proteins, or modified AAV9 capsid proteins.

In some aspects, the modified AAV capsid proteins are derived from an AAV1 capsid protein (see SEQ ID NO: 138), and the targeting peptide is inserted after residue 590 of the AAV1 capsid protein. In some aspects, the targeting peptide is flanked by linker sequences, and the linker sequences on each side of the targeting peptides are two or three amino acids long. In some aspects, the linker sequences are SSA on the N-terminal side of the targeting peptide and AS on the C-terminal side of the targeting peptide. In some aspects, the modified AAV1 capsid proteins have a sequence at least 95% identical to SEQ ID NO: 141.

In some aspects, the modified AAV capsid proteins are derived from an AAV2 capsid protein (see SEQ ID NO: 139), and the targeting peptide is inserted after residue 587 of the AAV2 capsid protein. In some aspects, the targeting peptide is flanked by linker sequences, and the linker sequences on each side of the targeting peptides are two or three amino acids long. In some aspects, the linker sequences are AAA on the N-terminal side of the targeting peptide and AA on the C-terminal side of the targeting peptide. In some aspects, the modified AAV2 capsid proteins have a sequence at least 95% identical to SEQ ID NO: 142.

In some aspects, the modified AAV capsid proteins are derived from an AAV9 capsid protein (see SEQ ID NO: 140), and the targeting peptide is inserted after residue 588 of the AAV9 capsid protein. In some aspects, the targeting peptide is flanked by linker sequences, and the linker sequences on each side of the targeting peptides are two or three amino acids long. In some aspects, the linker sequences are AAA on the N-terminal side of the targeting peptide and AS on the C-terminal side of the targeting peptide. In some aspects, the modified AAV9 capsid proteins have a sequence at least 95% identical to SEQ ID NO: 143.

In some aspects, the target peptide comprises a sequence up to ten amino acids in length having therein an amino acid sequence selected from the group consisting of SEQ ID NOs: 1-137 and 144. In some aspects, the targeting peptide is seven amino acids in length.

In some aspects, the distinct brain structure is the brainstem, caudate, cerebellar cortex, cerebral cortex, ependyma, globus pallidus, hippocampus, meninges, optic nerve, putamen, spinal cord, substantia nigra, subthalamic nuclei, or thalamus. In certain aspects, the modified AAV capsid protein is a modified AAV1 capsid protein, and the targeting peptide is selected from those listed in Table 1 in order to target a corresponding brain structure. In certain aspects, the modified AAV capsid protein is a modified AAV2 capsid protein, and the targeting peptide is selected from those listed in Table 2 in order to target a corresponding brain structure. In certain aspects, the modified AAV capsid protein is a modified AAV9 capsid protein, and the targeting peptide is selected from those listed in Table 3 in order to target a corresponding brain structure.

In some aspects, the distinct organ is the brain, kidney, heart, liver, gonad, spleen, or liver. In certain aspects, the modified AAV capsid protein is a modified AAV1 capsid protein, and the targeting peptide is selected from those listed in Table 4 in order to target a corresponding organ. In certain aspects, the modified AAV capsid protein is a modified AAV2 capsid protein, and the targeting peptide is selected from those listed in Table 5 in order to target a corresponding organ. In certain aspects, the modified AAV capsid protein is a modified AAV9 capsid protein, and the targeting peptide is selected from those listed in Table 6 in order to target a corresponding organ.

In one embodiment, provided herein are nucleic acids comprising a sequence encoding the modified capsid protein of any one of the present embodiments.

In one embodiment, provided herein are recombinant adeno-associated viruses (rAAV) comprising the modified capsid protein of any one of the present embodiments. In some aspects, combinations of rAAVs are provided. For example, the combination of an rAAV having a modified AAV1 capsid protein and a targeting peptide of SEQ ID NO: 21, an rAAV having a modified AAV2 capsid protein and a targeting peptide of SEQ ID NO: 53, an rAAV having a modified AAV2 capsid protein and a targeting peptide of SEQ ID NO: 80, and an rAAV having a modified AAV9capsid protein and a targeting peptide of SEQ ID NO: 113 is provided.

In one embodiment, provided herein are viral vectors comprising a nucleic acid encoding the modified capsid protein of any one of the present embodiments. In some aspects, the viral vectors further comprise a nucleic acid sequence encoding a nucleic acid of interest. In some aspects, the nucleic acid of interest is a therapeutic agent. In some aspects, the therapeutic agent is an enzyme or an RNAi molecule.

In one embodiment, provided herein are cells comprising the viral vector of any one of the present embodiments. In some aspects, the cell is a mammalian cell, such as a human cell. In some aspects, the cell is in vitro or in vivo.

In one embodiment, provided herein are pharmaceutical compositions comprising the viral vector of the present embodiments and a pharmaceutically acceptable carrier.

In one embodiment, provided herein are methods to deliver an agent to a distinct brain structure of a subject, comprising administering a virus of the present embodiments to the subject. In some aspects, the distinct brain structure is the brainstem, caudate, cerebellar cortex, cerebral cortex, ependyma, globus pallidus, hippocampus, meninges, optic nerve, putamen, spinal cord, substantia nigra, subthalamic nuclei, or thalamus. In certain aspects, an rAAV having a modified AAV1 capsid protein is used, and the targeting peptide is selected from those listed in Table 1 in order to target a corresponding brain structure. In certain aspects, an rAAV having a modified AAV2 capsid protein is used, and the targeting peptide is selected from those listed in Table 2 in order to target a corresponding brain structure. In certain aspects, an rAAV having a modified AAV9 capsid protein is used, and the targeting peptide is selected from those listed in Table 3 in order to target a corresponding brain structure. In various aspects, combinations of any of the rAAVs are used. For example, the combination of an rAAV having a modified AAV1 capsid protein and a targeting peptide of SEQ ID NO: 21, an rAAV having a modified AAV2 capsid protein and a targeting peptide of SEQ ID NO: 53, an rAAV having a modified AAV2 capsid protein and a targeting peptide of SEQ ID NO: 80, and an rAAV having a modified AAV9capsid protein and a targeting peptide of SEQ ID NO: 113 is used.

In one embodiment, provided herein are methods to deliver an agent to a distinct organ of a subject, comprising administering a virus of the present embodiments to the subject. In some aspects, the organ is the brain, kidney, heart, liver, gonad, spleen, or liver. In certain aspects, an rAAV having a modified AAV1 capsid protein is used, and the targeting peptide is selected from those listed in Table 4 in order to target a corresponding organ. In certain aspects, an rAAV having a modified AAV2 capsid protein is used, and the targeting peptide is selected from those listed in Table 5 in order to target a corresponding organ. In certain aspects, an rAAV having a modified AAV9 capsid protein is used, and the targeting peptide is selected from those listed in Table 6 in order to target a corresponding organ. In various aspects, combinations of any of the rAAVs are used.

In some aspects, the agent is an siRNA, shRNA, miRNA, non-coding RNA, lncRNA, therapeutic protein, or CRISPR system. In some aspects, the administration is to the central nervous system. In some aspects, the administration is to a cisterna magna, an intraventricular space, an ependyma, a brain ventricle, a subarachnoid space, and/or an intrathecal space. In some aspects, the brain ventricle is the rostral lateral ventricle, and/or the caudal lateral ventricle, and/or the right lateral ventricle, and/or the left lateral ventricle, and/or the right rostral lateral ventricle, and/or the left rostral lateral ventricle, and/or the right caudal lateral ventricle, and/or the left caudal lateral ventricle.

In some aspects, a plurality of viral particles is administered. In some aspects, the virus is administered at a dose of about $1\times10^6$ to about $1\times10^{18}$ vector genomes per kilogram (vg/kg). In some aspects, the virus is administered at a dose from about $1\times10^7$-$1\times10^{17}$, about $1\times10^8$-$1\times10^{16}$, about $1\times10^9$-$1\times10^{15}$, about $1\times10^{10}$-$1\times10^{14}$, about $1\times10^{10}$-$1\times10^{13}$, about $1\times10^{10}$-$1\times10^{13}$, about $1\times10^{10}$-$1\times10^{11}$, about $1\times10^{11}$-$1\times10^{12}$, about $1\times10^{12}$-$\times10^{13}$, or about $1\times10^{13}$-$1\times10^{14}$ vg/kg of the patient. In some aspects, the subject is human.

In one embodiment, provided herein are methods of treating a disease in a mammal comprising administering the virus of the present embodiments to the mammal. In some aspects, the disease is a neurodegenerative disease. In some aspects, the neurodegenerative disease is Huntington's disease, ALS, hereditary spastic hemiplegia, primary lateral sclerosis, spinal muscular atrophy, Kennedy's disease, Alzheimer's disease, a polyglutamine repeat disease, or Parkinson's disease. In some aspects, the mammal is human.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, the variation that exists among the study subjects, or a value that is within 10% of a stated value.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

In FIG. 7A, RPGREAS is SEQ ID NO: 144, RDATRSS is SEQ ID NO: 12, NSVRPLT is SEQ ID NO: 23, TAPKSLK is SEQ ID NO: 25, RGVLVTT is SEQ ID NO: 2, DKTRAGS is SEQ ID NO: 5, RDSTROL is SEQ ID NO: 26, PIPAGKK is SEQ ID NO: 9, SGVLVOR is SEQ ID NO: 32, NSVHNTA is SEQ ID NO: 18, TATPRKG is SEQ ID NO: 49, VSLKERV is SEQ ID NO: 29, DETSRLV is SEQ ID NO: 30, SVASAKK is SEQ ID NO: 48, NDVRAKG is SEQ ID NO: 40, SGTFVKA is SEQ ID NO: 33, DRLKGIV is SEQ ID NO: 31, KAAGRTV is SEQ ID NO: 46, ERDRTRG is SEQ ID NO: 21, NSVKSVL is SEQ ID NO: 27, VKALGRP is SEQ ID NO: 39, AKLNKSS is SEQ ID NO: 17, KGLRTPT is SEQ ID NO: 51, HVIRLPS is SEQ ID NO: 47, and TNRMALS is SEQ ID NO: 43. In FIG. 7B, HDGGASR is SEQ ID NO: 103, GSRAGVG is SEQ ID NO: 105, ESTGRER is SEQ ID NO: 73, KAQGVGG is SEQ ID NO: 79, RGSTQVG is SEQ ID NO: 94, EAQSHPR is SEQ ID NO: 91, RDDVPLR is SEQ ID NO: 56, GRSTGMT is SEQ ID NO: 95, VPGRTAG is SEQ ID NO: 81, ARGSGVN is SEQ ID NO: 82, GRGGAAL is SEQ ID NO: 100, TKSLSSG is SEQ ID NO: 92, RAVPAGG is SEQ ID NO: 84, NARPVSA is SEQ ID NO: 76, DDPSARR is SEQ ID NO: 53, TSNRGOV is SEQ ID NO: 63, VOGROGG is SEQ ID NO: 60, SSSKTGS is SEQ ID NO: 58, KASGAGG is SEQ ID NO: 88, VTOSKGA is SEQ ID NO: 74, STPAPKS is SEQ ID NO: 86, RSNAPOT is SEQ ID NO: 90, LTSRTSP is SEQ ID NO: 52, RGSGSAV is SEQ ID NO: 75, and KLSISGN is SEQ ID NO: 106. In FIG. 7C, MMGRPGR is SEQ ID NO: 136, KGGGFHG is SEQ ID NO: 110, RGDLOWV is SEQ ID NO: 113, MDLTKAV is SEQ ID NO: 135, RGGGVYG is SEQ ID NO: 126, RAKPGME is SEQ ID NO: 111, GGRPGSW is SEQ ID NO: 123, RSDVGSL is SEQ ID NO: 120, KGGGVHG is SEQ ID NO: 117, RGDLRFI is SEQ ID NO: 125, AGVKPGR is SEQ ID NO: 121, GRDVTRS is SEQ ID NO: 112, AWDGTRV is SEQ ID NO: 131, GGDRTRG is SEQ ID NO: 114, ARGDGWR is SEQ ID NO: 132, RRGDAWS is SEQ ID NO: 134, GADRTRG is SEQ ID NO: 127, RDTTRNL is SEQ ID NO: 116, RGDLASV is SEQ ID NO: 115, GRDYTRL is SEQ ID NO: 133, RRDETRT is SEQ ID NO: 129, RGDMYRV is SEQ ID NO: 118, RGDEMGL is SEQ ID NO: 128, RGDWPRG is SEQ ID NO: 122, and RGDYPRS is SEQ ID NO: 124.

FIGS. 9A-D. AAV9 1999 in vivo mouse validation. An eGFP expression construct was packaged into AAV9 1999 driven by the CAG promoter. AAV9 1999 and AAV9 capsids containing the eGFP construct were delivered to C57BL/6 p0 mouse pups by ICV injection at 1E10 vg. Representative images of eGFP fluorescence signal is the whole brain (FIG. 9A), whole brain sagittal section (FIG. 9B), Si cortex sections (FIG. 9C, left), hippocampus sections (FIG. 9C, middle), cerebellum sagittal section (FIG. 9C, right), and lumbar spinal cord coronal section (FIG. 9D).

DETAILED DESCRIPTION

Figure 1:
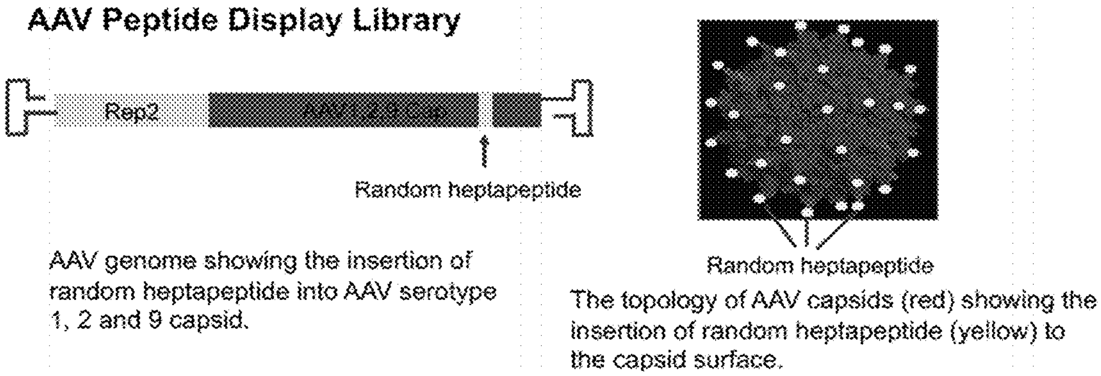
FIG. 1. AAV peptide display library schematic.

Provided herein are viral vectors each comprising a modified capsid, wherein the modified capsid comprises at least one amino acid sequence that targets the viral vector to a distinct brain structure. In certain embodiments, the brain structure is the brainstem, caudate, cerebellar cortex, cerebral cortex, ependyma, globus pallidus, hippocampus, meninges, optic nerve, putamen, spinal cord, substantia nigra, subthalamic nuclei, or thalamus. The targeting peptides for each brain structure are provided in Tables 1-3.

In certain embodiments, the viral vector is an adeno associated viral vector (AAV). In certain embodiments, the AAV is AAV1, AAV2, or AAV9. An exemplary wildtype reference AAV1 capsid protein sequence is provided in SEQ ID NO: 138. An exemplary wildtype reference AAV2 capsid protein sequence is provided in SEQ ID NO: 139. An exemplary wildtype reference AAV9 capsid protein sequence is provided in SEQ ID NO: 140. In certain aspects, the targeting peptide is inserted at position 590 of the AAV1 capsid, position 587 of the AAV2 capsid, or position 588 of the AAV9 capsid. An exemplary modified AAV1 capsid protein sequence is provided in SEQ ID NO: 141, which shows the targeting peptide insertion after position 590 as SSAX$_7$AS, where the leading SSA and the trailing AS are linker sequences and X$_7$ represents the targeting peptide. An exemplary modified AAV2 capsid protein sequence is provided in SEQ ID NO: 142, which shows the targeting peptide insertion after position 587 as AAAX$_7$AA, where the leading AAA and the trailing AA are linker sequences and X$_7$ represents the targeting peptide. An exemplary modified AAV9 capsid protein sequence is provided in SEQ ID NO: 143, which shows the targeting peptide insertion after position 588 as $AAAX_7AS$, where the leading AAA and the trailing AS are linker sequences and $X_7$ represents the targeting peptide.

TABLE 1

AAV1 targeting peptides for each brain structure.

| Region | Peptide | SEQ ID NO |
|---|---|---|
| Brainstem | RPGREQA | 1 |
| | RGVLVTT | 2 |
| | RPGRESA | 3 |
| | NESLKKK | 4 |
| | DKTRAGS | 5 |
| | TAKSKQA | 6 |
| | PVKKKDA | 7 |
| | GRETLKG | 8 |
| | PIPAGKK | 9 |
| Caudate | RPGRESA | 3 |
| | PVKKKDA | 7 |
| | RPGREQA | 1 |
| | NVVRAGT | 10 |
| | KATANTR | 11 |
| | RDATRSS | 12 |
| | VPTKSPK | 13 |
| | AGVARSK | 14 |
| | RSRSEVL | 15 |
| | EVKGKGK | 16 |
| | RPGREAS | 144 |
| | RDSTRQL | 26 |
| | SGVLVQR | 32 |
| | DKTRAGS | 5 |
| | TAPKSLK | 25 |
| Cerebellar Cortex | AKLNKSS | 17 |
| | NESLKKK | 4 |
| | NSVHNTA | 18 |
| | NVVRGGA | 19 |
| | NRLVAGG | 20 |
| | RPGRESA | 3 |
| | ERDRTRG | 21 |
| | PIPAGKK | 9 |
| | RPGREQA | 1 |
| Cerebellar Cortex; Vermis | RPGREAS | 144 |
| | DKTRAGS | 5 |
| | NSVRPLT | 23 |
| | RDSTRQL | 26 |
| | RDATRSS | 12 |
| Cerebellum; right upper vermis | NSVRPLT | 23 |
| | RDATRSS | 12 |
| | DKTRAGS | 5 |
| | TAPKSLK | 25 |
| | RPGREAS | 144 |
| Cerebellum; lateral to brainstem (right) | NSVRPLT | 23 |
| | TAPKSLK | 25 |
| | RDSTRQL | 26 |
| | RPGREAS | 144 |
| | PIPAGKK | 9 |
| | RDATRSS | 12 |
| Cerebellum; Left hemisphere adjacent to upper vermis | RPGREAS | 144 |
| | DKTRAGS | 5 |
| | RDATRSS | 12 |
| | RDSTRQL | 26 |
| | TAPKSLK | 25 |
| Cerebellum; Left hemisphere, Most lateral point | RPGREAS | 144 |
| | RDSTRQL | 26 |
| | DKTRAGS | 5 |
| | TAPKSLK | 25 |
| | NSVRPLT | 23 |
| | RDATRSS | 12 |

TABLE 1-continued

AAV1 targeting peptides for each brain structure.

| Region | Peptide | SEQ ID NO |
|---|---|---|
| Cerebellum; Left hemisphere, Adjacent to brain stem | NSVRPLT | 23 |
| | RPGREAS | 144 |
| | RDATRSS | 12 |
| | DKTRAGS | 5 |
| | NSVHNTA | 18 |
| | TAPKSLK | 25 |
| Cerebral Cortex | VQGSKMK | 22 |
| | RDATRSS | 12 |
| | NSVRPLT | 23 |
| | RPGRESA | 3 |
| | NKIHANP | 24 |
| | ERDRTRG | 21 |
| | DKTRAGS | 5 |
| | TAPKSLK | 25 |
| | RDSTRQL | 26 |
| | RPGREQA | 1 |
| Cochlea (ear) | RDATRSS | 12 |
| | RPGREAS | 144 |
| | TAPKSLK | 25 |
| | DKTRAGS | 5 |
| | NSVRPLT | 23 |
| | TATPRKG | 49 |
| Deep Cerebellar Nuclei | RPGREAS | 144 |
| | TAPKSLK | 25 |
| | RDATRSS | 12 |
| | RDSTRQL | 26 |
| | DKTRAGS | 5 |
| Dorsal Root Ganglia, Lumbar | RPGREAS | 144 |
| | RDATRSS | 12 |
| | NSVRPLT | 23 |
| | DKTRAGS | 5 |
| | TAPKSLK | 25 |
| Dorsal Root Ganglia, Cervical | RPGREAS | 144 |
| | DKTRAGS | 5 |
| | TAPKSLK | 25 |
| | RDATRSS | 12 |
| | NSVHNTA | 18 |
| | NSVRPLT | 23 |
| Dorsal Root Ganglia, Thoracic | RDATRSS | 12 |
| | RPGREAS | 144 |
| | DKTRAGS | 5 |
| | TAPKSLK | 25 |
| | RDSTRQL | 26 |
| Ependyma | ERDRTRG | 21 |
| | RGVLVTT | 2 |
| | RPGRESA | 3 |
| | PIPAGKK | 9 |
| | NESLKKK | 4 |
| | NSVKSVL | 27 |
| | PVKKKDA | 7 |
| | VQGSKMK | 22 |
| | NVTIKSK | 28 |
| Ependyma; 3rd Ventrical | DKTRAGS | 5 |
| | TAPKSLK | 25 |
| | RPGREAS | 144 |
| | RDATRSS | 12 |
| | DRLKGIV | 31 |
| Ependyma; 4th Ventrical | TAPKSLK | 25 |
| | NSVRPLT | 23 |
| | RPGREAS | 144 |
| | KAAGRTV | 46 |
| | RDATRSS | 12 |
| | DKTRAGS | 5 |

TABLE 1-continued

AAV1 targeting peptides for each brain structure.

| Region | Peptide | SEQ ID NO |
|---|---|---|
| Ependyma; Lt Ventrical | RPGREAS | 144 |
| | NSVRPLT | 23 |
| | RDATRSS | 12 |
| | TAPKSLK | 25 |
| | DETSRLV | 30 |
| | DKTRAGS | 5 |
| Globus Pallidus | RPGRESA | 3 |
| | ERDRTRG | 21 |
| | VSLKERV | 29 |
| | VQGSKMK | 22 |
| | DKTRAGS | 5 |
| | DETSRLV | 30 |
| | RDATRSS | 12 |
| | AGVARSK | 14 |
| | EVKGKGK | 16 |
| | DRLKGIV | 31 |
| Globus Pallidus External | RGVLVTT | 2 |
| | SGTFVKA | 33 |
| | EVKGKGK | 16 |
| | SVASAKK | 48 |
| | VSLKERV | 29 |
| | TATPRKG | 49 |
| Globus Pallidus Internal | RGVLVTT | 2 |
| | TAPKSLK | 25 |
| | TKTGLKL | 50 |
| | ERDRTRG | 21 |
| | SGVLVQR | 32 |
| | TATPRKG | 49 |
| | RPGREAS | 144 |
| Hippocampus | RGVLVTT | 2 |
| | RPGRESA | 3 |
| | SGVLVQR | 32 |
| | PVKKKDA | 7 |
| | NESLKKK | 4 |
| | SGTFVKA | 33 |
| | RPGREQA | 1 |
| | NSIARPV | 34 |
| Hippocampus; CA1 | RGVLVTT | 2 |
| | SGVLVQR | 32 |
| | SVASAKK | 48 |
| | RDATRSS | 12 |
| | DKTRAGS | 5 |
| | TAPKSLK | 25 |
| Hippocampus; CA3 | RPGREAS | 144 |
| | DETSRLV | 30 |
| | RDATRSS | 12 |
| | DKTRAGS | 5 |
| | ERDRTRG | 21 |
| | RDSTRQL | 26 |
| Hippocampus; DG | NSVRPLT | 23 |
| | RDATRSS | 12 |
| | TAPKSLK | 25 |
| | RDSTRQL | 26 |
| | RPGREAS | 144 |
| Inferior Olive | RPGREAS | 144 |
| | DKTRAGS | 5 |
| | TAPKSLK | 25 |
| | NDVRAKG | 40 |
| | RDATRSS | 12 |
| | NSVRPLT | 23 |
| Lateral Geniculate Nuclei | NSVRPLT | 23 |
| | TAPKSLK | 25 |
| | RPGREAS | 144 |
| | DKTRAGS | 5 |
| | RDATRSS | 12 |

TABLE 1-continued

AAV1 targeting peptides for each brain structure.

| Region | Peptide | SEQ ID NO |
|---|---|---|
| Meninges | RPGRESA | 3 |
| | ERDRTRG | 21 |
| | RDATRSS | 12 |
| | DKTRAGS | 5 |
| | PIPAGKK | 9 |
| | NRARAGE | 35 |
| | ARHALGG | 36 |
| | HSSRPVA | 37 |
| | PVKKKDA | 7 |
| | RPGREAS | 144 |
| | TAPKSLK | 25 |
| | NSVRPLT | 23 |
| Motor Cortex | RPGREAS | 144 |
| | RGVLVTT | 2 |
| | NSVRPLT | 23 |
| | TAPKSLK | 25 |
| | DKTRAGS | 5 |
| | RDATRSS | 12 |
| Optic Nerve | AGVARSK | 14 |
| | RSRSEVL | 15 |
| | EVKGKGK | 16 |
| | DRLKGIV | 31 |
| | KTGTARL | 38 |
| | RPGRESA | 3 |
| | PVKKKDA | 7 |
| | RGVLVTT | 2 |
| | ERDRTRG | 21 |
| | RPGREAS | 144 |
| | NSVRPLT | 23 |
| | TAPKSLK | 25 |
| | DKTRAGS | 5 |
| | NDVRAKG | 40 |
| | RDATRSS | 12 |
| Prefrontal Cortex | RPGREAS | 144 |
| | NSVRPLT | 23 |
| | TAPKSLK | 25 |
| | DKTRAGS | 5 |
| | RDATRSS | 12 |
| Pons | RPGREAS | 144 |
| | NSVRPLT | 23 |
| | TAPKSLK | 25 |
| | RDATRSS | 12 |
| | DKTRAGS | 5 |
| Putamen | DETSRLV | 30 |
| | VKALGRP | 39 |
| | NDVRAKG | 40 |
| | NESLKKK | 4 |
| | ERDRTRG | 21 |
| | RPGREAS | 144 |
| | QGVLVVR | 41 |
| | KQYAGSQ | 42 |
| | RDATRSS | 12 |
| | VPTKSPK | 13 |
| | DKTRAGS | 5 |
| | KAAGRTV | 46 |
| | TAPKSLK | 25 |
| Reticular Formation | RPGREAS | 144 |
| | RDSTRQL | 26 |
| | KGLRTPT | 51 |
| | RDATRSS | 12 |
| | NSVRPLT | 23 |
| | DKTRAGS | 5 |

TABLE 1-continued

AAV1 targeting peptides for each brain structure.

| Region | Peptide | SEQ ID NO |
|---|---|---|
| Spinal Cord | PVKKKDA | 7 |
| | RGVLVTT | 2 |
| | PIPAGKK | 9 |
| | SGVLVQR | 32 |
| | NESLKKK | 4 |
| | RPGRESA | 3 |
| | TNRMALS | 43 |
| | ERDRTRG | 21 |
| | SGTFVKA | 33 |
| Spinal Cord, Thoracic | NSVRPLT | 23 |
| | SGTFVKA | 33 |
| | RPGREAS | 144 |
| | RGVLVTT | 2 |
| | RDATRSS | 12 |
| | TAPKSLK | 25 |
| | DKTRAGS | 5 |
| Spinal Cord, Lumbar | RPGREAS | 144 |
| | TATPRKG | 49 |
| | TAPKSLK | 25 |
| | RDATRSS | 12 |
| | KAAGRTV | 46 |
| Spinal Cord, Cervical | SGVLVQR | 32 |
| | NSVRPLT | 23 |
| | RPGREAS | 144 |
| | RGVLVTT | 2 |
| | SGTFVKA | 33 |
| | TAPKSLK | 25 |
| | RDATRSS | 12 |
| | DKTRAGS | 5 |
| Substantia Nigra | RGVLVTT | 2 |
| | GITLGRL | 44 |
| | RPGRESA | 3 |
| | PIPAGKK | 9 |
| | AGIMVRV | 45 |
| | SGVLVQR | 32 |
| | VSLKERV | 29 |
| | RDSTRQL | 26 |
| | RPGREAS | 144 |
| | RDATRSS | 12 |
| Subthalamic Nuclei | KAAGRTV | 46 |
| | RDATRSS | 12 |
| | RGVLVTT | 2 |
| | RPGRESA | 3 |
| | HVIRLPS | 47 |
| | EVKGKGK | 16 |
| | NESLKKK | 4 |
| | DETSRLV | 30 |
| | NSVRPLT | 23 |
| | SGTFVKA | 33 |
| | PIPAGKK | 9 |
| | VKALGRP | 39 |
| Temporal Cortex | NSVRPLT | 23 |
| | RPGREAS | 144 |
| | TAPKSLK | 25 |
| | RDATRSS | 12 |
| | DKTRAGS | 5 |
| Thalamus | GRETLKG | 8 |
| | RPGREQA | 1 |
| | ERDRTRG | 21 |
| | RGVLVTT | 2 |
| | SVASAKK | 48 |
| | TATPRKG | 49 |
| | RDATRSS | 12 |
| | NVTIKSK | 28 |
| | TKTGLKL | 50 |
| | KGLRTPT | 51 |
| Thalamus, Anterior | SGVLVQR | 32 |
| | NSVHNTA | 18 |

TABLE 1-continued

AAV1 targeting peptides for each brain structure.

| Region | Peptide | SEQ ID NO |
|---|---|---|
| | PIPAGKK | 9 |
| | DETSRLV | 30 |
| | AKLNKSS | 17 |
| | RPGREAS | 144 |
| VA/VL Thalamus | RGVLVTT | 2 |
| | DKTRAGS | 5 |
| | DETSRLV | 30 |
| | RDSTRQL | 26 |
| | NKIHANP | 24 |
| | TAPKSLK | 25 |
| Visual Cortex | RPGREAS | 144 |
| | NSVRPLT | 23 |
| | TAPKSLK | 25 |
| | RDATRSS | 12 |
| | NSVHNTA | 18 |
| | DKTRAGS | 5 |

TABLE 2

AAV2 targeting peptides for each brain structure.

| Region | Peptide | SEQ ID NO |
|---|---|---|
| Brainstem | LTSRTSP | 52 |
| | DDPSARR | 53 |
| | GEQDLRR | 54 |
| | VSTALPR | 55 |
| | RDDVPLR | 56 |
| | TRVGTAG | 57 |
| | SSSKTGS | 58 |
| | SLSTGPK | 59 |
| | VQGRQGG | 60 |
| Caudate | RGASGAV | 61 |
| | NARAQGV | 62 |
| | TSNRGQV | 63 |
| | AVRGGMA | 64 |
| | RGLDKGT | 65 |
| | KGVDLKP | 66 |
| | TAVREER | 67 |
| | GNAGITK | 68 |
| | SLSTGPK | 59 |
| | SARAGAP | 69 |
| | GSRAGVG | 105 |
| | NARPVSA | 76 |
| | HDGGASR | 103 |
| | VTQSKGA | 74 |
| | KAQGVGG | 79 |
| | ESTGRER | 73 |
| Cerebellar Cortex | SGEFVGR | 70 |
| | SGRKLEV | 71 |
| | SARSGSV | 72 |
| | ESTGRER | 73 |
| | SSSKTGS | 58 |
| | RDDVPLR | 56 |
| | VQGRQGG | 60 |
| | VTQSKGA | 74 |
| | RGSGSAV | 75 |
| Cerebellar Cortex; Vermis | HDGGASR | 103 |
| | EAQSHPR | 91 |
| | ESTGRER | 73 |
| | GRSTGMT | 95 |
| | GSRAGVG | 105 |

TABLE 2-continued

AAV2 targeting peptides for each brain structure.

| Region | Peptide | SEQ ID NO |
|---|---|---|
| Cerebellum; right upper vermis | HDGGASR | 103 |
| | RAVPAGG | 84 |
| | RSNAPQT | 90 |
| | TKSLSSG | 92 |
| | ESTGRER | 73 |
| | RGSTQVG | 94 |
| Cerebellum; lateral to brainstem (right) | HDGGASR | 103 |
| | ESTGRER | 73 |
| | KAQGVGG | 79 |
| | EAQSHPR | 91 |
| | RAVPAGG | 84 |
| | RDDVPLR | 56 |
| Cerebellar Left hemisphere adjacent to upper vermis | HDGGASR | 103 |
| | ESTGRER | 73 |
| | EAQSHPR | 91 |
| | NARAQGV | 62 |
| | LTSRTSP | 52 |
| | KAQGVGG | 79 |
| Cerebellar Left hemisphere Most lateral point | HDGGASR | 103 |
| | ESTGRER | 73 |
| | EAQSHPR | 91 |
| | KAQGVGG | 79 |
| | GSRAGVG | 105 |
| Cerebellar Left hemisphere Adjacent to brain stem | ESTGRER | 73 |
| | HDGGASR | 103 |
| | EAQSHPR | 91 |
| | GSRAGVG | 105 |
| | KAQGVGG | 79 |
| | GRGGAAL | 100 |
| Cerebral Cortex | DDPSARR | 53 |
| | NARPVSA | 76 |
| | TSNRGQV | 63 |
| | NARAQGV | 62 |
| | TARGGGG | 77 |
| | KGVDLKP | 66 |
| | GRSASGS | 78 |
| | SSSKTGS | 58 |
| | KAQGVGG | 79 |
| | VQGROGG | 60 |
| Cochlea (ear) | HDGGASR | 103 |
| | KAQGVGG | 79 |
| | RSNAPQT | 90 |
| | LTSRTSP | 52 |
| | EAQSHPR | 91 |
| Deep Cerebellar Nuclei | GSRAGVG | 105 |
| | RAVPAGG | 84 |
| | EAQSHPR | 91 |
| | AVRGGMA | 64 |
| | VPGRTAG | 81 |
| | VTQSKGA | 74 |
| Dorsal Root Ganglia Lumbar | HDGGASR | 103 |
| | TKSLSSG | 92 |
| | KAQGVGG | 79 |
| | GSRAGVG | 105 |
| | VPGRTAG | 81 |
| Dorsal Root Ganglia Cervical | GRSTGMT | 95 |
| | AVRGGMA | 64 |
| | HDGGASR | 103 |
| | TAAGGQR | 99 |
| | KAQGVGG | 79 |
| Dorsal Root Ganglia Thoracic | HDGGASR | 103 |
| | GSRAGVG | 105 |
| | ARGSGVN | 82 |
| | RAVPAGG | 84 |
| | KAQGVGG | 79 |

TABLE 2-continued

AAV2 targeting peptides for each brain structure.

| Region | Peptide | SEQ ID NO |
|---|---|---|
| Ependyma | GRGAPGG | 80 |
| | DDPSARR | 53 |
| | TSNRGQV | 63 |
| | RGSGSAV | 75 |
| | VQGROGG | 60 |
| | VTQSKGA | 74 |
| | NARPVSA | 76 |
| | KGVDLKP | 66 |
| | NARAQGV | 62 |
| | TARGGGG | 77 |
| Ependyma; 4th Ventrical | GSRAGVG | 105 |
| | RDDVPLR | 56 |
| | RGSTQVG | 94 |
| | KAQGVGG | 79 |
| | GRGGAAL | 100 |
| Ependyma; Lt Ventrical | HDGGASR | 103 |
| | ESTGRER | 73 |
| | EAQSHPR | 91 |
| | NARPVSA | 76 |
| | KAQGVGG | 79 |
| Ependyma; 3rd Ventrical | GRSTGMT | 95 |
| | LTSRTSP | 52 |
| | KAQGVGG | 79 |
| | GRGGAAL | 100 |
| | EAQSHPR | 91 |
| | ARGSGVN | 82 |
| Globus Pallidus | VQGROGG | 60 |
| | VPGRTAG | 81 |
| | ARGSGVN | 82 |
| | SVRVGGQ | 83 |
| | RGSGSAV | 75 |
| | RAVPAGG | 84 |
| | VMSSGKP | 85 |
| | STPAPKS | 86 |
| | RGGAQVV | 87 |
| Globus Pallidus External | EAQSHPR | 91 |
| | GSRAGVG | 105 |
| | VQGRQGG | 60 |
| | ESTGRER | 73 |
| | GRGGAAL | 100 |
| | KASGAGG | 88 |
| Globus Pallidus Internal | RDDVPLR | 56 |
| | GSRAGVG | 105 |
| | GAVGGVK | 107 |
| | DDPSARR | 53 |
| | RGSTQVG | 94 |
| | KAQGVGG | 79 |
| Hippocampus | DDPSARR | 53 |
| | KASGAGG | 88 |
| | KAQGVGG | 79 |
| | TSNRGQV | 63 |
| | VQGRQGG | 60 |
| | VSTALPR | 55 |
| | TGTAGLK | 89 |
| | NARPVSA | 76 |
| | SSSKTGS | 58 |
| Hippocampus; CA1 | VAPISKS | 101 |
| | HDGGASR | 103 |
| | LTSRTSP | 52 |
| | ESTGRER | 73 |
| | KAQGVGG | 79 |
| Hippocampus; CA3 | VQGROGG | 60 |
| | GRSTGMT | 95 |
| | GRGGAAL | 100 |
| | KAQGVGG | 79 |
| | RGSTQVG | 94 |
| | TSNRGQV | 63 |

TABLE 2-continued

AAV2 targeting peptides for each brain structure.

| Region | Peptide | SEQ ID NO |
|---|---|---|
| Hippocampus; DG | HDGGASR | 103 |
| | ESTGRER | 73 |
| | RGSTQVG | 94 |
| | EAQSHPR | 91 |
| | KAQGVGG | 79 |
| | GSRAGVG | 105 |
| Inferior Olive | VPGRTAG | 81 |
| | HDGGASR | 103 |
| | VQGROGG | 60 |
| | GSRAGVG | 105 |
| | RDDVPLR | 56 |
| | KAQGVGG | 79 |
| Lateral geniculate nuclei | HDGGASR | 103 |
| | ESTGRER | 73 |
| | GSRAGVG | 105 |
| | KAQGVGG | 79 |
| | EAQSHPR | 91 |
| | VPGRTAG | 81 |
| Meninges | SSSKTGS | 58 |
| | NARPVSA | 76 |
| | RSNAPQT | 90 |
| | EAQSHPR | 91 |
| | TKSLSSG | 92 |
| | GRGAPGG | 80 |
| | AAGAKVM | 93 |
| | ESTGRER | 73 |
| | KGVDLKP | 66 |
| | VQGRQGG | 60 |
| | HDGGASR | 103 |
| | KAQGVGG | 79 |
| | RGSTQVG | 94 |
| | VPGRTAG | 81 |
| | GSRAGVG | 105 |
| Optic Nerve | DDPSARR | 53 |
| | RGGAQVV | 87 |
| | KASGAGG | 88 |
| | RGSGSAV | 75 |
| | VQGROGG | 60 |
| | KAQGVGG | 79 |
| | TRVGTAG | 57 |
| | GEQDLRR | 54 |
| | RGSTQVG | 94 |
| | SSSKTGS | 58 |
| | GSRAGVG | 105 |
| | ESTGRER | 73 |
| | HDGGASR | 103 |
| | RDDVPLR | 56 |
| Pons | ESTGRER | 73 |
| | GSRAGVG | 105 |
| | HDGGASR | 103 |
| | KAQGVGG | 79 |
| | RDDVPLR | 56 |
| | GRGGAAL | 100 |
| Prefrontal Cortex | HDGGASR | 103 |
| | GSRAGVG | 105 |
| | ESTGRER | 73 |
| | KAQGVGG | 79 |
| | RGSTQVG | 94 |
| Primary motor cortex | GSRAGVG | 105 |
| | VPGRTAG | 81 |
| | ESTGRER | 73 |
| | RGSTQVG | 94 |
| | GRGGAAL | 100 |
| | KAQGVGG | 79 |
| Primary Visual Cortex | HDGGASR | 103 |
| | ESTGRER | 73 |
| | EAQSHPR | 91 |

TABLE 2-continued

AAV2 targeting peptides for each brain structure.

| Region | Peptide | SEQ ID NO |
|---|---|---|
| | TKSLSSG | 92 |
| | GSRAGVG | 105 |
| | KAQGVGG | 79 |
| Putamen | GRSTGMT | 95 |
| | RATSQST | 96 |
| | VGRSVGA | 97 |
| | VQGRQGG | 60 |
| | GEGGGGR | 98 |
| | VSTALPR | 55 |
| | RGASGAV | 61 |
| | TAAGGQR | 99 |
| | SLSTGPK | 59 |
| | GRGGAAL | 100 |
| | RAVPAGG | 84 |
| | KAQGVGG | 79 |
| | GSRAGVG | 105 |
| | VPGRTAG | 81 |
| | HDGGASR | 103 |
| | RDDVPLR | 56 |
| Reticular Formation | VTQSKGA | 74 |
| | DDPSARR | 53 |
| | TGTAGLK | 89 |
| | ARGSGVN | 82 |
| | RGSTQVG | 94 |
| | RDDVPLR | 56 |
| Spinal Cord | SLSTGPK | 59 |
| | GRSTGMT | 95 |
| | RGASGAV | 61 |
| | TARGGGG | 77 |
| | KASGAGG | 88 |
| | VAPISKS | 101 |
| | DDPSARR | 53 |
| | TSNRGQV | 63 |
| | SSSKTGS | 58 |
| | VQGROGG | 60 |
| Spinal Cord Thoracic | HDGGASR | 103 |
| | ESTGRER | 73 |
| | EAQSHPR | 91 |
| | GSRAGVG | 105 |
| | VQGROGG | 60 |
| | KAQGVGG | 79 |
| Spinal Cord Lumbar | HDGGASR | 103 |
| | EAQSHPR | 91 |
| | DDPSARR | 53 |
| | KLSISGN | 106 |
| | VMSSGKP | 85 |
| | KAQGVGG | 79 |
| | TSNRGQV | 63 |
| Spinal Cord Cervical | ESTGRER | 73 |
| | HDGGASR | 103 |
| | EAQSHPR | 91 |
| | GSRAGVG | 105 |
| | RGSTQVG | 94 |
| | KAQGVGG | 79 |
| Substantia Nigra | LTSRTSP | 52 |
| | NARPVSA | 76 |
| | SSSKTGS | 58 |
| | RGGAQVV | 87 |
| | APPVKLS | 102 |
| | DDPSARR | 53 |
| | RGSGSAV | 75 |
| | HDGGASR | 103 |
| | TRVGTAG | 57 |
| | GSRAGVG | 105 |
| | KLSISGN | 106 |
| | KAQGVGG | 79 |
| | TGTAGLK | 89 |
| | ARGSGVN | 82 |

TABLE 2-continued

AAV2 targeting peptides for each brain structure.

| Region | Peptide | SEQ ID NO |
|---|---|---|
| Subthalamic Nuclei | VQGRQGG | 60 |
| | RSGGAAV | 104 |
| | KASGAGG | 88 |
| | SSSKTGS | 58 |
| | KAQGVGG | 79 |
| | GSRAGVG | 105 |
| | RGGAQVV | 87 |
| | APPVKLS | 102 |
| | RGSGSAV | 75 |
| | TRVGTAG | 57 |
| | RGSTQVG | 94 |
| | KLSISGN | 106 |
| | RDDVPLR | 56 |
| | GRGGAAL | 100 |
| | TSNRGQV | 63 |
| Temporal Cortex | ESTGRER | 73 |
| | HDGGASR | 103 |
| | GSRAGVG | 105 |
| | KAQGVGG | 79 |
| | RDDVPLR | 56 |
| Thalamus | KASGAGG | 88 |
| | RDDVPLR | 56 |
| | LTSRTSP | 52 |
| | KLSISGN | 106 |
| | VSTALPR | 55 |
| | VMSSGKP | 85 |
| | GAVGGVK | 107 |
| | KNESGKV | 108 |
| | VTQSKGA | 74 |
| | AGQLAGR | 109 |
| Thalamus, Anterior | RGSTQVG | 94 |
| | KAQGVGG | 79 |
| | TKSLSSG | 92 |
| | RAVPAGG | 84 |
| | TSNRGQV | 63 |
| | RDDVPLR | 56 |
| VA/VL Thalamus | TRVGTAG | 57 |
| | ARGSGVN | 82 |
| | GRGGAAL | 100 |
| | NARPVSA | 76 |
| | VQGRQGG | 60 |
| | GSRAGVG | 105 |

TABLE 3

AAV9 targeting peptides for each brain structure.

| Region | Peptide | SEQ ID NO |
|---|---|---|
| Brainstem | KGGGFHG | 110 |
| | RAKPGME | 111 |
| | GRDVTRS | 112 |
| | RGDLQWV | 113 |
| | GGDRTRG | 114 |
| | RGDLASV | 115 |
| | RDTTRNL | 116 |
| | KGGGVHG | 117 |
| Caudate | KGGGFHG | 110 |
| | RGDLQWV | 113 |
| | RGDMYRV | 118 |
| | RGDRPVS | 119 |
| | RSDVGSL | 120 |
| | RGDLASV | 115 |
| | RDTTRNL | 116 |
| | AGVKPGR | 121 |
| | KGGGVHG | 117 |
| | RAKPGME | 111 |
| | GADRTRG | 127 |

TABLE 3-continued

AAV9 targeting peptides for each brain structure.

| Region | Peptide | SEQ ID NO |
|---|---|---|
| | GRDVTRS | 112 |
| | ARGDGWR | 132 |
| | RGGGVYG | 126 |
| | GGDRTRG | 114 |
| | GRDYTRL | 133 |
| Cortex, Cerebellar | KGGGFHG | 110 |
| | RGDLQWV | 113 |
| | RAKPGME | 111 |
| | RGDWPRG | 122 |
| | RGDRPVS | 119 |
| | GGRPGSW | 123 |
| | RGDYPRS | 124 |
| | RGDLRFI | 125 |
| Cortex, Cerebral | KGGGFHG | 110 |
| | RAKPGME | 111 |
| | RDTTRNL | 116 |
| | RGGGVYG | 126 |
| | GGDRTRG | 114 |
| | GADRTRG | 127 |
| | RGDLQWV | 113 |
| | RGDLRFI | 125 |
| Cortex, Prefrontal | KGGGFHG | 110 |
| | MMGRPGR | 136 |
| | AGVKPGR | 121 |
| | RGGGVYG | 126 |
| | RGDLRFI | 125 |
| | RGDWPRG | 122 |
| | RGDLQWV | 113 |
| | RGDRPVS | 119 |
| Cortex, Motor | MMGRPGR | 136 |
| | KGGGFHG | 110 |
| | AGVKPGR | 121 |
| | RGGGVYG | 126 |
| | RGDLRFI | 125 |
| | RGDWPRG | 122 |
| | RGDLQWV | 113 |
| Cortex, Temporal | KGGGFHG | 110 |
| | RGGGVYG | 126 |
| | MMGRPGR | 136 |
| | RGDLRFI | 125 |
| | RGDLQWV | 113 |
| | RGDWPRG | 122 |
| Cortex, Visual | AGVKPGR | 121 |
| | MMGRPGR | 136 |
| | RGDLRFI | 125 |
| | RGDLQWV | 113 |
| | RGDFMGL | 128 |
| | RGGGVYG | 126 |
| | KGGGFHG | 110 |
| | AWDGTRV | 131 |
| Cochlea (ear) | MMGRPGR | 136 |
| | KGGGFHG | 110 |
| | RGDLASV | 115 |
| | AGVKPGR | 121 |
| | GGRPGSW | 123 |
| | RGGGVYG | 126 |
| | GGDRTRG | 114 |
| Deep Cerebellar Nuclei | RSDVGSL | 120 |
| | KGGGFHG | 110 |
| | RGDLQWV | 113 |
| | GRDVTRS | 112 |
| | RGDLRFI | 125 |
| | RGGGVYG | 126 |
| | RAKPGME | 111 |
| Dorsal Root Ganglia Lumbar | MMGRPGR | 136 |
| | AGVKPGR | 121 |
| | GGRPGSW | 123 |

TABLE 3-continued

AAV9 targeting peptides for each brain structure.

| Region | Peptide | SEQ ID NO |
|---|---|---|
| | GRDYTRL | 133 |
| | RGGGVYG | 126 |
| | GGDRTRG | 114 |
| Dorsal Root Ganglia Cervical | RGDLQWV | 113 |
| | KGGGFHG | 110 |
| | RRDETRT | 129 |
| | RGGGVYG | 126 |
| | GADRTRG | 127 |
| | RGDRPVS | 119 |
| | GGDRTRG | 114 |
| Dorsal Root Ganglia Thoracic | MMGRPGR | 136 |
| | AGVKPGR | 121 |
| | GGRPGSW | 123 |
| | GRDYTRL | 133 |
| | RGDFMGL | 128 |
| | RGGGVYG | 126 |
| | GGDRTRG | 114 |
| | RAKPGME | 111 |
| | AWDGTRV | 131 |
| Ependyma | KGGGFHG | 110 |
| | RGDLQWV | 113 |
| | RAKPGME | 111 |
| | RGDMYRV | 118 |
| | RSDVGSL | 120 |
| | RGDFMGL | 128 |
| | RGDRPVS | 119 |
| Ependyma; 4th Ventrical | RGDLQWV | 113 |
| | RGDLASV | 115 |
| | RSDVGSL | 120 |
| | RGDLRFI | 125 |
| | MDLTKAV | 135 |
| | RGGGVYG | 126 |
| | RAKPGME | 111 |
| | RGDRPVS | 119 |
| | GGDRTRG | 114 |
| Ependyma; Lt Ventrical | MMGRPGR | 136 |
| | RSDVGSL | 120 |
| | AGVKPGR | 121 |
| | GGRPGSW | 123 |
| | RAKPGME | 111 |
| | RGGGVYG | 126 |
| | GRDVTRS | 112 |
| | RGDLQWV | 113 |
| Ependyma; 3rd Ventrical | KGGGVHG | 117 |
| | GADRTRG | 127 |
| | GGDRTRG | 114 |
| | MMGRPGR | 136 |
| | RGDLQWV | 113 |
| | RGGGVYG | 126 |
| | GRDVTRS | 112 |
| Globus Pallidus | KGGGFHG | 110 |
| | RRDETRT | 129 |
| | RAKPGME | 111 |
| | GGDRTRG | 114 |
| | GRDVTRS | 112 |
| | RSDVGSL | 120 |
| | RGDRPVS | 119 |
| Globus Pallidus External | RAKPGME | 111 |
| | RRGDAWS | 134 |
| | RGDMYRV | 118 |
| | RGDLQWV | 113 |
| | GRDVTRS | 112 |
| | RGGGVYG | 126 |
| Globus Pallidus Internal | MDLTKAV | 135 |
| | RDTTRNL | 116 |
| | AWDGTRV | 131 |
| | RGGGVYG | 126 |

TABLE 3-continued

AAV9 targeting peptides for each brain structure.

| Region | Peptide | SEQ ID NO |
|---|---|---|
| | KGGGVHG | 117 |
| | RGDLQWV | 113 |
| Hippocampus | KGGGFHG | 110 |
| | AESPWER | 130 |
| | RGDLQWV | 113 |
| | RAKPGME | 111 |
| | RRDETRT | 129 |
| | RGDLRFI | 125 |
| | GGRPGSW | 123 |
| | RDTTRNL | 116 |
| Hippocampus CA1 | KGGGFHG | 110 |
| | ARGDGWR | 132 |
| | RGGGVYG | 126 |
| | AWDGTRV | 131 |
| | GADRTRG | 127 |
| | RAKPGME | 111 |
| Hippocampus CA3 | RAKPGME | 111 |
| | RRDETRT | 129 |
| | MDLTKAV | 135 |
| | AWDGTRV | 131 |
| | RDTTRNL | 116 |
| | GGDRTRG | 114 |
| | GRDVTRS | 112 |
| | RGGGVYG | 126 |
| Hippocampus; DG | KGGGFHG | 110 |
| | RGDFMGL | 128 |
| | RGGGVYG | 126 |
| | ARGDGWR | 132 |
| | RGDLRFI | 125 |
| | RGDLQWV | 113 |
| | GRDYTRL | 133 |
| Inferior Olive | RRGDAWS | 134 |
| | GGRPGSW | 123 |
| | KGGGFHG | 110 |
| | KGGGVHG | 117 |
| | RGDWPRG | 122 |
| | RGGGVYG | 126 |
| | GRDYTRL | 133 |
| | RGDRPVS | 119 |
| Meninges | KGGGFHG | 110 |
| | RGDLQWV | 113 |
| | RAKPGME | 111 |
| | RGDWPRG | 122 |
| | GGDRTRG | 114 |
| | AWDGTRV | 131 |
| | RGDMYRV | 118 |
| | RGDRPVS | 119 |
| | RSDVGSL | 120 |
| | KGGGVHG | 117 |
| | GRDVTRS | 112 |
| | AGVKPGR | 121 |
| | RGGGVYG | 126 |
| Optic Nerve | KGGGFHG | 110 |
| | RAKPGME | 111 |
| | RRDETRT | 129 |
| | RDTTRNL | 116 |
| | GGDRTRG | 114 |
| | ARGDGWR | 132 |
| | KGGGVHG | 117 |
| | RGDLRFI | 125 |
| | RGGGVYG | 126 |
| | AGVKPGR | 121 |
| | RGDLQWV | 113 |
| Pons | KGGGFHG | 110 |
| | RGGGVYG | 126 |
| | RRDETRT | 129 |
| | AGVKPGR | 121 |
| | KGGGVHG | 117 |

TABLE 3-continued

AAV9 targeting peptides for each brain structure.

| Region | Peptide | SEQ ID NO |
|---|---|---|
| | RAKPGME | 111 |
| | RGDLQWV | 113 |
| | GRDYTRL | 133 |
| Putamen | KGGGFHG | 110 |
| | GRDVTRS | 112 |
| | GADRTRG | 127 |
| | GRDYTRL | 133 |
| | RDTTRNL | 116 |
| | RGDLQWV | 113 |
| | RRGDAWS | 134 |
| | GGRPGSW | 123 |
| | KGGGVHG | 117 |
| | RGDMYRV | 118 |
| | RAKPGME | 111 |
| | RGGGVYG | 126 |
| | GGDRTRG | 114 |
| | RGDRPVS | 119 |
| Reticular Formation | MMGRPGR | 136 |
| | GRDVTRS | 112 |
| | GADRTRG | 127 |
| | RAKPGME | 111 |
| | RSDVGSL | 120 |
| | RGGGVYG | 126 |
| | AWDGTRV | 131 |
| Spinal Cord | KGGGFHG | 110 |
| | RGDLQWV | 113 |
| | RGDRPVS | 119 |
| | RGDWPRG | 122 |
| | RSDVGSL | 120 |
| | GGRPGSW | 123 |
| | RRGDAWS | 134 |
| | RGDFMGL | 128 |
| Spinal Cord; Thoracic | KGGGFHG | 110 |
| | RGGGVYG | 126 |
| | RGDLQWV | 113 |
| | RGDLRFI | 125 |
| | RRGDAWS | 134 |
| | RGDRPVS | 119 |
| | GRDYTRL | 133 |
| Spinal Cord; Lumbar | RGDLASV | 115 |
| | KGGGFHG | 110 |
| | RGGGVYG | 126 |
| | MMGRPGR | 136 |
| | RGDLQWV | 113 |
| | AWDGTRV | 131 |
| | RAKPGME | 111 |
| Spinal Cord; Cervical | KGGGFHG | 110 |
| | RGDLRFI | 125 |
| | RGGGVYG | 126 |
| | RRGDAWS | 134 |
| | RGDLQWV | 113 |
| | RGDWPRG | 122 |
| Substantia Nigra | KGGGFHG | 110 |
| | RAKPGME | 111 |
| | GRDVTRS | 112 |
| | GGDRTRG | 114 |
| | RRDETRT | 129 |
| | RGDLQWV | 113 |
| | KGGGVHG | 117 |
| | MDLTKAV | 135 |
| | RRGDAWS | 134 |
| | GGRPGSW | 123 |
| | GADRTRG | 127 |
| | RGGGVYG | 126 |
| Subthalamic Nuclei | KGGGFHG | 110 |
| | RAKPGME | 111 |
| | MDLTKAV | 135 |
| | RGDRPVS | 119 |
| | RGDWPRG | 122 |
| | ARGDGWR | 132 |
| | RGDLQWV | 113 |
| | RSDVGSL | 120 |
| | RGDLASV | 115 |
| | RGGGVYG | 126 |
| Thalamus | KGGGFHG | 110 |
| | GRDVTRS | 112 |
| | GGDRTRG | 114 |
| | RGDLQWV | 113 |
| | GRDYTRL | 133 |
| | RGDLRFI | 125 |
| | MMGRPGR | 136 |
| | TGRPGVW | 137 |
| Thalamus, Anterior | MDLTKAV | 135 |
| | GGRPGSW | 123 |
| | RGDLRFI | 125 |
| | RDTTRNL | 116 |
| | RAKPGME | 111 |
| | RGGGVYG | 126 |
| | GRDYTRL | 133 |
| | RGDWPRG | 122 |
| VA/VL Thalamus | RGDWPRG | 122 |
| | GGDRTRG | 114 |
| | RRGDAWS | 134 |
| | RGDLRFI | 125 |
| | RGDYPRS | 124 |
| | RGDRPVS | 119 |
| | RGGGVYG | 126 |

TABLE 4

AAV1 targeting peptides for various organs.

| Organ | Peptide | SEQ ID NO |
|---|---|---|
| Brain | RPGREAS | 144 |
| | TAPKSLK | 25 |
| | RDATRSS | 12 |
| | DKTRAGS | 5 |
| | NSVRPLT | 23 |
| | RDSTRQL | 26 |
| | RGVLVTT | 2 |

TABLE 5

AAV2 targeting peptides for various organs.

| Organ | Peptide | SEQ ID NO |
|---|---|---|
| Brain | HDGGASR | 103 |
| | KAQGVGG | 79 |
| | GSRAGVG | 105 |
| | ESTGRER | 73 |
| | RDDVPLR | 56 |
| | RGSTQVG | 94 |
| | EAQSHPR | 91 |
| Kidney | GSRAGVG | 105 |
| | TSNRGQV | 63 |
| | GRSTGMT | 95 |
| | GRGAPGG | 80 |
| | GAVGGVK | 107 |
| | KAQGVGG | 79 |
| | RDDVPLR | 56 |

TABLE 5-continued

| AAV2 targeting peptides for various organs. | | |
|---|---|---|
| Organ | Peptide | SEQ ID NO |
| Heart | HDGGASR | 103 |
| | SLSTGPK | 59 |
| | GSRAGVG | 105 |
| | RGSTQVG | 94 |
| | NARAQGV | 62 |
| | ESTGRER | 73 |
| Liver | KAQGVGG | 79 |
| | GSRAGVG | 105 |
| | RDDVPLR | 56 |
| | HDGGASR | 103 |
| | NARPVSA | 76 |
| Gonad | VPGRTAG | 81 |
| | KAQGVGG | 79 |
| | RGSTQVG | 94 |
| | HDGGASR | 103 |
| | GAVGGVK | 107 |
| | RDDVPLR | 56 |
| Spleen | KAQGVGG | 79 |
| | GSRAGVG | 105 |
| | GRGGAAL | 100 |
| | VPGRTAG | 81 |
| | ESTGRER | 73 |
| Lung | ESTGRER | 73 |
| | TKSLSSG | 92 |
| | RGSTQVG | 94 |
| | KAQGVGG | 79 |
| | NARPVSA | 76 |

TABLE 6

| AAV9 targeting peptides for various organs. | | |
|---|---|---|
| Organ | Peptide | SEQ ID NO |
| Brain | RGGGVYG | 126 |
| | RAKPGME | 111 |
| | KGGGFHG | 110 |
| | GGDRTRG | 114 |
| | MMGRPGR | 136 |
| | RGDLQWV | 113 |
| | MDLTKAV | 135 |
| | GGRPGSW | 123 |
| Kidney | MMGRPGR | 136 |
| | RGDLQWV | 113 |
| | RAKPGME | 111 |
| | RSDVGSL | 120 |
| | KGGGFHG | 110 |
| | RGGGVYG | 126 |
| Heart | GGRPGSW | 123 |
| | RSDVGSL | 120 |
| | RGDLASV | 115 |
| | KGGGFHG | 110 |
| | GRDYTRL | 133 |
| | RGGGVYG | 126 |
| | RAKPGME | 111 |
| Liver | GGDRTRG | 114 |
| | GRDVTRS | 112 |
| | RDTTRNL | 116 |
| | RRDETRT | 129 |
| | RSDVGSL | 120 |
| | RGGGVYG | 126 |
| | RAKPGME | 111 |
| | GRDYTRL | 133 |
| Gonad | KGGGVHG | 117 |
| | KGGGFHG | 110 |

TABLE 6-continued

| AAV9 targeting peptides for various organs. | | |
|---|---|---|
| Organ | Peptide | SEQ ID NO |
| | RSDVGSL | 120 |
| | GGRPGSW | 123 |
| | RRDETRT | 129 |
| | RGGGVYG | 126 |
| | GGDRTRG | 114 |
| | RGDRPVS | 119 |
| | RAKPGME | 111 |

I. ADENO-ASSOCIATED VIRUS (AAV) VECTORS

Adeno-associated virus (AAV) is a small nonpathogenic virus of the parvoviridae family. To date, numerous serologically distinct AAVs have been identified, and more than a dozen have been isolated from humans or primates. AAV is distinct from other members of this family by its dependence upon a helper virus for replication.

AAV genomes can exist in an extrachromosomal state without integrating into host cellular genomes; possess a broad host range; transduce both dividing and non-dividing cells in vitro and in vivo and maintain high levels of expression of the transduced genes. AAV viral particles are heat stable; resistant to solvents, detergents, changes in pH, and temperature; and can be column purified and/or concentrated on CsCl gradients or by other means. The AAV genome comprises a single-stranded deoxyribonucleic acid (ssDNA), either positive- or negative-sensed. The approximately 4.7 kb genome of AAV consists of one segment of single stranded DNA of either plus or minus polarity. The ends of the genome are short inverted terminal repeats (ITRs) that can fold into hairpin structures and serve as the origin of viral DNA replication.

An AAV "genome" refers to a recombinant nucleic acid sequence that is ultimately packaged or encapsulated to form an AAV particle. An AAV particle often comprises an AAV genome packaged with AAV capsid proteins. In cases where recombinant plasmids are used to construct or manufacture recombinant vectors, the AAV vector genome does not include the portion of the "plasmid" that does not correspond to the vector genome sequence of the recombinant plasmid. This non vector genome portion of the recombinant plasmid is referred to as the "plasmid backbone," which is important for cloning and amplification of the plasmid, a process that is needed for plasmid propagation and production, but is not itself packaged or encapsulated into viral particles. Thus, an AAV vector "genome" refers to nucleic acid that is packaged or encapsulated by AAV capsid proteins.

The AAV virion (particle) is a non-enveloped, icosahedral particle approximately 25 nm in diameter that comprises an AAV capsid. The AAV particle comprises an icosahedral symmetry comprised of three related capsid proteins, VP1, VP2 and VP3, which interact together to form the capsid. The genome of most native AAVs often contain two open reading frames (ORFs), sometimes referred to as a left ORF and a right ORF. The right ORF often encodes the capsid proteins VP1, VP2, and VP3. These proteins are often found in a ratio of 1:1:10 respectively, but may be in varied ratios, and are all derived from the right-hand ORF. The VP1, VP2 and VP3 capsid proteins differ from each other by the use of alternative splicing and an unusual start codon. Deletion analysis has shown that removal or alteration of VP1 which is translated from an alternatively spliced message results in a reduced yield of infectious particles. Mutations within the VP3 coding region result in the failure to produce any single-stranded progeny DNA or infectious particles. In certain embodiments, the genome of an AAV particle encodes one, two or all three VP1, VP2 and VP3 polypeptides.

The left ORF often encodes the non-structural Rep proteins, Rep 40, Rep 52, Rep 68 and Rep 78, which are involved in regulation of replication and transcription in addition to the production of single-stranded progeny genomes. Two of the Rep proteins have been associated with the preferential integration of AAV genomes into a region of the q arm of human chromosome 19. Rep68/78 have been shown to possess NTP binding activity as well as DNA and RNA helicase activities. Some Rep proteins possess a nuclear localization signal as well as several potential phosphorylation sites. In certain embodiments the genome of an AAV (e.g., an rAAV) encodes some or all of the Rep proteins. In certain embodiments the genome of an AAV (e.g., an rAAV) does not encode the Rep proteins. In certain embodiments one or more of the Rep proteins can be delivered in trans and are therefore not included in an AAV particle comprising a nucleic acid encoding a polypeptide.

The ends of the AAV genome comprise short inverted terminal repeats (ITR) which have the potential to fold into T-shaped hairpin structures that serve as the origin of viral DNA replication. Accordingly, the genome of an AAV comprises one or more (e.g., a pair of) ITR sequences that flank a single stranded viral DNA genome. The ITR sequences often have a length of about 145 bases each. Within the ITR region, two elements have been described which are believed to be central to the function of the ITR, a GAGC repeat motif and the terminal resolution site (trs). The repeat motif has been shown to bind Rep when the ITR is in either a linear or hairpin conformation. This binding is thought to position Rep68/78 for cleavage at the trs which occurs in a site- and strand-specific manner. In addition to their role in replication, these two elements appear to be central to viral integration. Contained within the chromosome 19 integration locus is a Rep binding site with an adjacent trs. These elements have been shown to be functional and necessary for locus specific integration.

The term "recombinant," as a modifier of vector, such as recombinant viral, e.g., lenti- or parvo-virus (e.g., AAV) vectors, as well as a modifier of sequences such as recombinant nucleic acid sequences and polypeptides, means that the compositions have been manipulated (i.e., engineered) in a fashion that generally does not occur in nature. A particular example of a recombinant vector, such as an AAV, retroviral, or lentiviral vector would be where a nucleic acid sequence that is not normally present in the wild-type viral genome is inserted within the viral genome. An example of a recombinant nucleic acid sequence would be where a nucleic acid (e.g., gene) encodes an inhibitory RNA cloned into a vector, with or without 5', 3' and/or intron regions that the gene is normally associated within the viral genome. Although the term "recombinant" is not always used herein in reference to vectors, such as viral vectors, as well as sequences such as polynucleotides, "recombinant" forms including nucleic acid sequences, polynucleotides, transgenes, etc. are expressly included in spite of any such omission.

A recombinant viral "vector" is derived from the wild type genome of a virus by using molecular methods to remove part of the wild type genome from the virus, and replacing with a non-native nucleic acid, such as a nucleic acid sequence. Typically, for example, for AAV, one or both inverted terminal repeat (ITR) sequences of the AAV genome are retained in the recombinant AAV vector. A "recombinant" viral vector (e.g., rAAV) is distinguished from a viral (e.g., AAV) genome, since part of the viral genome has been replaced with a non-native sequence with respect to the viral genomic nucleic acid such a nucleic acid encoding a transactivator or nucleic acid encoding an inhibitory RNA or nucleic acid encoding a therapeutic protein. Incorporation of such non-native nucleic acid sequences therefore defines the viral vector as a "recombinant" vector, which in the case of AAV can be referred to as a "rAAV vector."

In certain embodiments, an AAV (e.g., a rAAV) comprises two ITRs. In certain embodiments, an AAV (e.g., a rAAV) comprises a pair of ITRs. In certain embodiments, an AAV (e.g., a rAAV) comprises a pair of ITRs that flank (i.e., are at each 5' and 3' end) of a nucleic acid sequence that at least encodes a polypeptide having function or activity.

An AAV vector (e.g., rAAV vector) can be packaged and is referred to herein as an "AAV particle" for subsequent infection (transduction) of a cell, ex vivo, in vitro or in vivo. Where a recombinant AAV vector is encapsulated or packaged into an AAV particle, the particle can also be referred to as a "rAAV particle." In certain embodiments, an AAV particle is a rAAV particle. A rAAV particle often comprises a rAAV vector, or a portion thereof. A rAAV particle can be one or more rAAV particles (e.g., a plurality of AAV particles). rAAV particles typically comprise proteins that encapsulate or package the rAAV vector genome (e.g., capsid proteins). It is noted that reference to a rAAV vector can also be used to reference a rAAV particle.

Any suitable AAV particle (e.g., rAAV particle) can be used for a method or use herein. A rAAV particle, and/or genome comprised therein, can be derived from any suitable serotype or strain of AAV. A rAAV particle, and/or genome comprised therein, can be derived from two or more serotypes or strains of AAV. Accordingly, a rAAV can comprise proteins and/or nucleic acids, or portions thereof, of any serotype or strain of AAV, wherein the AAV particle is suitable for infection and/or transduction of a mammalian cell. Non-limiting examples of AAV serotypes include AAV1, AAV2, AAV3, AAV4, AAV5, AAV6, AAV7, AAV8, AAV9, AAV10, AAV11, AAV12, AAV-rh74, AAV-rh10 and AAV-2i8.

In certain embodiments a plurality of rAAV particles comprises particles of, or derived from, the same strain or serotype (or subgroup or variant). In certain embodiments a plurality of rAAV particles comprise a mixture of two or more different rAAV particles (e.g., of different serotypes and/or strains).

As used herein, the term "serotype" is a distinction used to refer to an AAV having a capsid that is serologically distinct from other AAV serotypes. Serologic distinctiveness is determined on the basis of the lack of cross-reactivity between antibodies to one AAV as compared to another AAV. Such cross-reactivity differences are usually due to differences in capsid protein sequences/antigenic determinants (e.g., due to VP1, VP2, and/or VP3 sequence differences of AAV serotypes). Despite the possibility that AAV variants including capsid variants may not be serologically distinct from a reference AAV or other AAV serotype, they differ by at least one nucleotide or amino acid residue compared to the reference or other AAV serotype.

In certain embodiments, a rAAV vector based upon a first serotype genome corresponds to the serotype of one or more of the capsid proteins that package the vector. For example, the serotype of one or more AAV nucleic acids (e.g., ITRs)

that comprises the AAV vector genome corresponds to the serotype of a capsid that comprises the rAAV particle.

In certain embodiments, a rAAV vector genome can be based upon an AAV (e.g., AAV2) serotype genome distinct from the serotype of one or more of the AAV capsid proteins that package the vector. For example, a rAAV vector genome can comprise AAV2 derived nucleic acids (e.g., ITRs), whereas at least one or more of the three capsid proteins are derived from a different serotype, e.g., an AAV1, AAV3, AAV4, AAV5, AAV6, AAV7, AAV8, AAV9, AAV10, AAV11, AAV12, Rh10, Rh74 or AAV-2i8 serotype or variant thereof.

In certain embodiments, a rAAV particle or a vector genome thereof related to a reference serotype has a polynucleotide, polypeptide or subsequence thereof that comprises or consists of a sequence at least 60% or more (e.g., 65%, 70%, 75%, 80%, 85%, 90%, 95%, 96%, 97%, 98%, 99%, 99.1%, 99.2%, 99.3%, 99.4%, 99.5%, etc.) identical to a polynucleotide, polypeptide or subsequence of an AAV1, AAV2, AAV3, AAV4, AAV5, AAV6, AAV7, AAV8, AAV9, AAV10, AAV11, AAV12, Rh10, Rh74 or AAV-2i8 particle. In particular embodiments, a rAAV particle or a vector genome thereof related to a reference serotype has a capsid or ITR sequence that comprises or consists of a sequence at least 60% or more (e.g., 65%, 70%, 75%, 80%, 85%, 90%, 95%, 96%, 97%, 98%, 99%, 99.1%, 99.2%, 99.3%, 99.4%, 99.5%, etc.) identical to a capsid or ITR sequence of an AAV1, AAV2, AAV3, AAV4, AAV5, AAV6, AAV7, AAV8, AAV9, AAV10, AAV11, AAV12, Rh10, Rh74 or AAV-2i8 serotype.

In certain embodiments, a method herein comprises use, administration or delivery of an rAAV1, rAAV2, rAAV3, rAAV4, rAAV5, rAAV6, rAAV7, rAAV8, rAAV9, rAAV10, rAAV11, rAAV12, rRh10, rRh74 or rAAV-2i8 particle.

In certain embodiments, a method herein comprises use, administration or delivery of a rAAV2 particle. In certain embodiments a rAAV2 particle comprises an AAV2 capsid. In certain embodiments a rAAV2 particle comprises one or more capsid proteins (e.g., VP1, VP2 and/or VP3) that are at least 60%, 65%, 70%, 75% or more identical, e.g., 80%, 85%, 85%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to a corresponding capsid protein of a native or wild-type AAV2 particle. In certain embodiments a rAAV2 particle comprises VP1, VP2 and VP3 capsid proteins that are at least 75% or more identical, e.g., 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to a corresponding capsid protein of a native or wild-type AAV2 particle. In certain embodiments, a rAAV2 particle is a variant of a native or wild-type AAV2 particle. In some aspects, one or more capsid proteins of an AAV2 variant have 1, 2, 3, 4, 5, 5-10, 10-15, 15-20 or more amino acid substitutions compared to capsid protein(s) of a native or wild-type AAV2 particle.

In certain embodiments a rAAV9 particle comprises an AAV9 capsid. In certain embodiments a rAAV9 particle comprises one or more capsid proteins (e.g., VP1, VP2 and/or VP3) that are at least 60%, 65%, 70%, 75% or more identical, e.g., 80%, 85%, 85%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to a corresponding capsid protein of a native or wild-type AAV9 particle. In certain embodiments a rAAV9 particle comprises VP1, VP2 and VP3 capsid proteins that are at least 75% or more identical, e.g., 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to a corresponding capsid protein of a native or wild-type AAV9 particle. In certain embodiments, a rAAV9 particle is a variant of a native or wild-type AAV9 particle. In some aspects, one or more capsid proteins of an AAV9 variant have 1, 2, 3, 4, 5, 5-10, 10-15, 15-20 or more amino acid substitutions compared to capsid protein(s) of a native or wild-type AAV9 particle.

In certain embodiments, a rAAV particle comprises one or two ITRs (e.g., a pair of ITRs) that are at least 75% or more identical, e.g., 80%, 85%, 85%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to corresponding ITRs of a native or wild-type AAV1, AAV2, AAV3, AAV4, AAV5, AAV6, AAV7, AAV8, AAV9, AAV10, AAV11, AAV12, AAV-rh74, AAV-rh10 or AAV-2i8, as long as they retain one or more desired ITR functions (e.g., ability to form a hairpin, which allows DNA replication; integration of the AAV DNA into a host cell genome; and/or packaging, if desired).

In certain embodiments, a rAAV2 particle comprises one or two ITRs (e.g., a pair of ITRs) that are at least 75% or more identical, e.g., 80%, 85%, 85%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to corresponding ITRs of a native or wild-type AAV2 particle, as long as they retain one or more desired ITR functions (e.g., ability to form a hairpin, which allows DNA replication; integration of the AAV DNA into a host cell genome; and/or packaging, if desired).

In certain embodiments, a rAAV9 particle comprises one or two ITRs (e.g., a pair of ITRs) that are at least 75% or more identical, e.g., 80%, 85%, 85%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to corresponding ITRs of a native or wild-type AAV2 particle, as long as they retain one or more desired ITR functions (e.g., ability to form a hairpin, which allows DNA replication; integration of the AAV DNA into a host cell genome; and/or packaging, if desired).

A rAAV particle can comprise an ITR having any suitable number of "GAGC" repeats. In certain embodiments an ITR of an AAV2 particle comprises 1, 2, 3, 4, 5, 6, 7, 8, 9 or 10 or more "GAGC" repeats. In certain embodiments a rAAV2 particle comprises an ITR comprising three "GAGC" repeats. In certain embodiments a rAAV2 particle comprises an ITR which has less than four "GAGC" repeats. In certain embodiments a rAAV2 particle comprises an ITR which has more than four "GAGC" repeats. In certain embodiments an ITR of a rAAV2 particle comprises a Rep binding site wherein the fourth nucleotide in the first two "GAGC" repeats is a C rather than a T.

Exemplary suitable length of DNA can be incorporated in rAAV vectors for packaging/encapsidation into a rAAV particle can about 5 kilobases (kb) or less. In particular, embodiments, length of DNA is less than about 5 kb, less than about 4.5 kb, less than about 4 kb, less than about 3.5 kb, less than about 3 kb, or less than about 2.5 kb.

rAAV vectors that include a nucleic acid sequence that directs the expression of an RNAi or polypeptide can be generated using suitable recombinant techniques known in the art (e.g., see Sambrook et al., 1989). Recombinant AAV vectors are typically packaged into transduction-competent AAV particles and propagated using an AAV viral packaging system. A transduction-competent AAV particle is capable of binding to and entering a mammalian cell and subsequently delivering a nucleic acid cargo (e.g., a heterologous gene) to the nucleus of the cell. Thus, an intact rAAV particle that is transduction-competent is configured to transduce a mammalian cell. A rAAV particle configured to transduce a mammalian cell is often not replication competent, and requires additional protein machinery to self-replicate. Thus, a rAAV particle that is configured to transduce a mammalian cell is engineered to bind and enter a mammalian cell and deliver a nucleic acid to the cell, wherein the nucleic acid for delivery is often positioned between a pair of AAV ITRs in the rAAV genome.

Suitable host cells for producing transduction-competent AAV particles include but are not limited to microorganisms, yeast cells, insect cells, and mammalian cells that can be, or have been, used as recipients of a heterologous rAAV vectors. Cells from the stable human cell line, HEK293 (readily available through, e.g., the American Type Culture Collection under Accession Number ATCC CRL1573) can be used. In certain embodiments a modified human embryonic kidney cell line (e.g., HEK293), which is transformed with adenovirus type-5 DNA fragments, and expresses the adenoviral Ela and E1b genes is used to generate recombinant AAV particles. The modified HEK293 cell line is readily transfected, and provides a particularly convenient platform in which to produce rAAV particles. Methods of generating high titer AAV particles capable of transducing mammalian cells are known in the art. For example, AAV particle can be made as set forth in Wright, 2008 and Wright, 2009.

In certain embodiments, AAV helper functions are introduced into the host cell by transfecting the host cell with an AAV helper construct either prior to, or concurrently with, the transfection of an AAV expression vector. AAV helper constructs are thus sometimes used to provide at least transient expression of AAV rep and/or cap genes to complement missing AAV functions necessary for productive AAV transduction. AAV helper constructs often lack AAV ITRs and can neither replicate nor package themselves. These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. A number of other vectors are known which encode Rep and/or Cap expression products.

An "expression vector" is a specialized vector that contains a gene or nucleic acid sequence with the necessary regulatory regions needed for expression in a host cell. An expression vector may contain at least an origin of replication for propagation in a cell and optionally additional elements, such as a heterologous nucleic acid sequence, expression control element (e.g., a promoter, enhancer), intron, ITR(s), and polyadenylation signal.

II. THERAPEUTIC AGENTS

In some embodiments, viral gene transfer methods can be used to introduce nucleic acids in mammalian cells or target tissues. Such methods can be used to administer nucleic acids encoding inhibitory RNAs, non-coding RNAs, and/or therapeutic proteins to cells in culture or in a host organism.

A. Inhibitory RNAs

"RNA interference (RNAi)" is the process of sequence-specific, post-transcriptional gene silencing initiated by siRNA. During RNAi, siRNA induces degradation of target mRNA with consequent sequence-specific inhibition of gene expression.

An "inhibitory RNA," "RNAi," "small interfering RNA" or "short interfering RNA" or "siRNA" molecule, "short hairpin RNA" or "shRNA" molecule, or "miRNA" is an RNA duplex of nucleotides that is targeted to a nucleic acid sequence of interest. As used herein, the term "siRNA" is a generic term that encompasses the subset of shRNAs and miRNAs. An "RNA duplex" refers to the structure formed by the complementary pairing between two regions of an RNA molecule. siRNA is "targeted" to a gene in that the nucleotide sequence of the duplex portion of the siRNA is complementary to a nucleotide sequence of the targeted gene. In certain embodiments, the siRNAs are targeted to the sequence encoding huntingtin. In some embodiments, the length of the duplex of siRNAs is less than 30 base pairs. In some embodiments, the duplex can be 29, 28, 27, 26, 25, 24, 23, 22, 21, 20, 19, 18, 17, 16, 15, 14, 13, 12, 11 or 10 base pairs in length. In some embodiments, the length of the duplex is 19 to 25 base pairs in length. In certain embodiment, the length of the duplex is 19 or 21 base pairs in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12, 13, 14, 15, 16, 17, 18, 19, 20, 21, 22, 23, 24 or 25 nucleotides in length. In certain embodiments, the loop is 18 nucleotides in length. The hairpin structure can also contain 3' and/or 5' overhang portions. In some embodiments, the overhang is a 3' and/or a 5' overhang 0, 1, 2, 3, 4 or 5 nucleotides in length.

shRNAs are comprised of stem-loop structures which are designed to contain a 5' flanking region, siRNA region segments, a loop region, a 3' siRNA region and a 3' flanking region. Most RNAi expression strategies have utilized short-hairpin RNAs (shRNAs) driven by strong p01111-based promoters. Many shRNAs have demonstrated effective knock down of the target sequences in vitro as well as in vivo, however, some shRNAs which demonstrated effective knock down of the target gene were also found to have toxicity in vivo.

miRNAs are small cellular RNAs (~22 nt) that are processed from precursor stem loop transcripts. Known miRNA stem loops can be modified to contain RNAi sequences specific for genes of interest. miRNA molecules can be preferable over shRNA molecules because miRNAs are endogenously expressed. Therefore, miRNA molecules are unlikely to induce dsRNA-responsive interferon pathways, they are processed more efficiently than shRNAs, and they have been shown to silence 80% more effectively.

A recently discovered alternative approach is the use of artificial miRNAs (pri-miRNA scaffolds shuttling siRNA sequences) as RNAi vectors. Artificial miRNAs more naturally resemble endogenous RNAi substrates and are more amenable to Pol-II transcription (e.g., allowing tissue-specific expression of RNAi) and polycistronic strategies (e.g., allowing delivery of multiple siRNA sequences). See U.S. Pat. No. 10,093,927, which is incorporated by reference.

The transcriptional unit of a "shRNA" is comprised of sense and antisense sequences connected by a loop of unpaired nucleotides. shRNAs are exported from the nucleus by Exportin-5, and once in the cytoplasm, are processed by Dicer to generate functional siRNAs. "miRNAs" stem-loops are comprised of sense and antisense sequences connected by a loop of unpaired nucleotides typically expressed as part of larger primary transcripts (pri-miRNAs), which are excised by the Drosha-DGCR8 complex generating intermediates known as pre-miRNAs, which are subsequently exported from the nucleus by Exportin-5, and once in the cytoplasm, are processed by Dicer to generate functional siRNAs. "Artificial miRNA" or an "artificial miRNA shuttle vector", as used herein interchangeably, refers to a primary miRNA transcript that has had a region of the duplex stem loop (at least about 9-20 nucleotides) which is excised via Drosha and Dicer processing replaced with the siRNA sequences for the target gene while retaining the structural elements within the stem loop necessary for effective Drosha processing. The term "artificial" arises from the fact the flanking sequences (~35 nucleotides upstream and ~40 nucleotides downstream) arise from restriction enzyme sites within the multiple cloning site of the siRNA. As used herein the term "miRNA" encompasses both the naturally occurring miRNA sequences as well as artificially generated miRNA shuttle vectors.

The siRNA can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal or a sequence of six Ts.

In designing RNAi there are several factors that need to be considered, such as the nature of the siRNA, the durability of the silencing effect, and the choice of delivery system. To produce an RNAi effect, the siRNA that is introduced into the organism will typically contain exonic sequences. Furthermore, the RNAi process is homology dependent, so the sequences must be carefully selected so as to maximize gene specificity, while minimizing the possibility of cross-interference between homologous, but not gene-specific sequences. Preferably the siRNA exhibits greater than 80%, 85%, 90%, 95%, 98%, or even 100% identity between the sequence of the siRNA and the gene to be inhibited. Sequences less than about 80% identical to the target gene are substantially less effective. Thus, the greater homology between the siRNA and the gene to be inhibited, the less likely expression of unrelated genes will be affected.

In addition, the size of the siRNA is an important consideration. In some embodiments, the present invention relates to siRNA molecules that include at least about 19-25 nucleotides and are able to modulate gene expression. In the context of the present invention, the siRNA is preferably less than 500, 200, 100, 50, or 25 nucleotides in length. More preferably, the siRNA is from about 19 nucleotides to about 25 nucleotides in length.

A siRNA target generally means a polynucleotide comprising a region that encodes a polypeptide, or a polynucleotide region that regulates replication, transcription, or translation or other processes important to expression of the polypeptide, or a polynucleotide comprising both a region that encodes a polypeptide and a region operably linked thereto that regulates expression. Any gene being expressed in a cell can be targeted. Preferably, a target gene is one involved in or associated with the progression of cellular activities important to disease or of particular interest as a research object.

B. Non-Coding RNAs

As evidenced by cDNA cloning projects and genomic tiling arrays, more than 90% of the human genome undergoes transcription but does not code for proteins. These transcriptional products are referred to as non-protein coding RNAs (ncRNAs). A variety of ncRNA transcripts, such as ribosomal RNAs, transfer RNAs, competing endogenous RNA (ceRNA), small nuclear RNA (snRNA), and small nucleolar RNA (snoRNA), are essential for cell function. Similarly, a large number of short ncRNAs such as microRNAs (miRNAs), endogenous short interfering RNAs (siRNAs), PIWI-interacting RNAs (piRNAs), and small nucleolar RNAs (snoRNAs) are also known to play important regulatory roles in eukaryotic cells. Recent studies have demonstrated a group of long ncRNA (lncRNA) transcripts that exhibit cell type-specific expression and localize into specific subcellular compartments. lncRNAs are also known to play important roles during cellular development and differentiation supporting the view that they have been selected during the evolutionary process.

LncRNAs appear to have many different functions. In many cases, they seem to play a role in regulating the activity or localization of proteins, or serve as organizational frameworks for subcellular structures. In other cases, lncRNAs are processed to yield multiple small RNAs or they may modulate how other RNAs are processed. The latest edition of data produced by the public research consortium GenCode (version #27) catalogs just under 16,000 lncRNAs in the human genome, producing nearly 28,000 transcripts; when other databases are included, more than 40,000 lncRNAs are known.

Interestingly, lncRNAs can influence the expression of specific target proteins at specific genomic loci, modulate the activity of protein binding partners, direct chromatin-modifying complexes to their sites of action, and are post-transcriptionally processed to produce numerous 5'-capped small RNAs. Epigenetic pathways can also regulate the differential expression of lncRNAs.

A growing body of evidence also suggests that aberrantly expressed lncRNAs play important roles in normal physiological processes as well as multiple disease states. lncRNAs are misregulated in various diseases, including ischaemia, heart disease, Alzheimer's disease, psoriasis, and spinocerebellar ataxia type 8. This misregulation has also been shown in various types of cancers, such as breast cancer, colon cancer, prostate cancer, hepatocellular carcinoma and leukemia. Several lncRNAs, e.g. gadd74 and lncRNA-RoR5, modulate cell cycle regulators such as cyclins, cyclin-dependent kinases (CDKs), CDK inhibitors and p53 and thus provide an additional layer of flexibility and robustness to cell cycle progression. In addition, some lncRNAs are linked to mitotic processes such as centromeric satellite RNA, which is essential for kinetochore formation and thus crucial for chromosome segregation during mitosis in humans and flies. Another nuclear lncRNA, MA-lincl, regulates M phase exit by functioning in cis to repress the expression of its neighbouring gene Pura, a regulator of cell proliferation.

lncRNAs are a group that is commonly defined as transcripts of more than 200 nucleotides (e.g. about 200 to about 1200 nt, about 2500 nt, or more) that lack an extended open reading frame (ORF). The term "non-coding RNA" (ncRNA) includes lncRNA as well as shorter transcripts of, e.g., less than about 200 nt, such as about 30 to 200 nt.

Thus, in some embodiments, delivery of a ncRNA, such as to a specific brain structure of interest, corrects aberrant RNA expression levels or modulates levels of disease-causing lncRNA. Accordingly, in some embodiments, the present invention provides an rAAV, wherein the viral genome is engineered to encode a therapeutic non-coding RNA (ncRNA). In some embodiments, the ncRNA is a long non-coding RNA (lncRNA) of about 200 nucleotides (nt) in length or greater. In some embodiments, the therapeutic is a ncRNA of about 25 nt or about 30 nt to about 200 nt in length. In some embodiments, the lncRNA is about 200 nt to about 1,200 nt in length. In some embodiments, the lncRNA is about 200 nt to about 1,100, about 1,000, about 900, about 800, about 700, about 600, about 500, about 400, or about 300 nt in length.

C. CRISPR Systems

Gene editing is a technology that allows for the modification of target genes within living cells. Recently, harnessing the bacterial immune system of CRISPR to perform on demand gene editing revolutionized the way scientists approach genomic editing. The Cas9 protein of the CRISPR system, which is an RNA guided DNA endonuclease, can be engineered to target new sites with relative ease by altering its guide RNA sequence. This discovery has made sequence specific gene editing functionally effective.

In general, "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), and/or other sequences and transcripts from a CRISPR locus.

The CRISPR/Cas nuclease or CRISPR/Cas nuclease system can include a non-coding RNA molecule (guide) RNA, which sequence-specifically binds to DNA, and a Cas protein (e.g., Cas9), with nuclease functionality (e.g., two nuclease domains). One or more elements of a CRISPR system can derive from a type I, type II, or type III CRISPR system, e.g., derived from a particular organism comprising an endogenous CRISPR system, such as *Streptococcus pyogenes.*

The CRISPR system can induce double stranded breaks (DSBs) at the target site, followed by disruptions as discussed herein. In other embodiments, Cas9 variants, deemed "nickases," are used to nick a single strand at the target site. Paired nickases can be used, e.g., to improve specificity, each directed by a pair of different gRNAs targeting sequences such that upon introduction of the nicks simultaneously, a 5' overhang is introduced. In other embodiments, catalytically inactive Cas9 is fused to a heterologous effector domain such as a transcriptional repressor (e.g., KRAB) or activator, to affect gene expression. Alternatively, a CRISPR system with a catalytically inactivate Cas9 further comprises a transcriptional repressor or activator fused to a ribosomal binding protein.

In some aspects, a Cas nuclease and gRNA (including a fusion of crRNA specific for the target sequence and fixed tracrRNA) are introduced into the cell. In general, target sites at the 5' end of the gRNA target the Cas nuclease to the target site, e.g., the gene, using complementary base pairing. The target site may be selected based on its location immediately 5' of a protospacer adjacent motif (PAM) sequence, such as typically NGG, or NAG. In this respect, the gRNA is targeted to the desired sequence by modifying the first 20, 19, 18, 17, 16, 15, 14, 14, 12, 11, or 10 nucleotides of the guide RNA to correspond to the target DNA sequence. In general, a CRISPR system is characterized by elements that promote the formation of a CRISPR complex at the site of a target sequence. Typically, "target sequence" generally refers to a sequence to which a guide sequence is designed to have complementarity, where hybridization between the target sequence and a guide sequence promotes the formation of a CRISPR complex. Full complementarity is not necessarily required, provided there is sufficient complementarity to cause hybridization and promote formation of a CRISPR complex.

The target sequence may comprise any polynucleotide, such as DNA or RNA polynucleotides. The target sequence may be located in the nucleus or cytoplasm of the cell, such as within an organelle of the cell. Generally, a sequence or template that may be used for recombination into the targeted locus comprising the target sequences is referred to as an "editing template" or "editing polynucleotide" or "editing sequence." In some aspects, an exogenous template polynucleotide may be referred to as an editing template. In some aspects, the recombination is homologous recombination.

Typically, in the context of an endogenous CRISPR system, formation of the CRISPR complex (comprising the guide sequence hybridized to the target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. The tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of the CRISPR complex, such as by hybridization along at least a portion of the tracr sequence to all or a portion of a tracr mate sequence that is operably linked to the guide sequence. The tracr sequence has sufficient complementarity to a tracr mate sequence to hybridize and participate in formation of the CRISPR complex, such as at least 50%, 60%, 70%, 80%, 90%, 95% or 99% of sequence complementarity along the length of the tracr mate sequence when optimally aligned.

One or more vectors driving expression of one or more elements of the CRISPR system can be introduced into the cell such that expression of the elements of the CRISPR system direct formation of the CRISPR complex at one or more target sites. Components can also be delivered to cells as proteins and/or RNA. For example, a Cas enzyme, a guide sequence linked to a tracr-mate sequence, and a tracr sequence could each be operably linked to separate regulatory elements on separate vectors. The Cas enzyme may be a target gene under the control of a regulated alternative splicing event, as disclosed herein, either as a chimeric target gene minigene or as a target gene for a chimeric minigene transactivator. The gRNA may be under the control of a constitutive promoter.

Alternatively, two or more of the elements expressed from the same or different regulatory elements, may be combined in a single vector, with one or more additional vectors providing any components of the CRISPR system not included in the first vector. The vector may comprise one or more insertion sites, such as a restriction endonuclease recognition sequence (also referred to as a "cloning site"). In some embodiments, one or more insertion sites are located upstream and/or downstream of one or more sequence elements of one or more vectors. When multiple different guide sequences are used, a single expression construct may be used to target CRISPR activity to multiple different, corresponding target sequences within a cell.

A vector may comprise a regulatory element operably linked to an enzyme-coding sequence encoding the CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of *S. pyogenes* Cas9 protein may be found in the SwissProt database under accession number Q99ZW2.

The CRISPR enzyme can be Cas9 (e.g., from *S. pyogenes* or *S. pneumonia*). The CRISPR enzyme can direct cleavage of one or both strands at the location of a target sequence, such as within the target sequence and/or within the complement of the target sequence. The vector can encode a CRISPR enzyme that is mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). In some embodiments, a Cas9 nickase may be used in combination with guide sequence(s), e.g., two guide sequences, which target respectively sense and antisense strands of the DNA target. This combination allows both strands to be nicked and used to induce NHEJ or HDR.

In some embodiments, an enzyme coding sequence encoding the CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

In general, a guide sequence is any polynucleotide sequence having sufficient complementarity with a target polynucleotide sequence to hybridize with the target sequence and direct sequence-specific binding of the CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more.

Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), Clustal W, Clustal X, BLAT, Novoalign (Novocraft Technologies, ELAND (Illumina, San Diego, Calif.), SOAP (available at soap.genomics.org.cn), and Maq (available at maq.sourceforge.net).

The CRISPR enzyme may be part of a fusion protein comprising one or more heterologous protein domains. A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-5-transferase (GST), horseradish peroxidase (HRP), chloramphenicol acetyltransferase (CAT) beta galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4A DNA binding domain fusions, and herpes simplex virus (HSV) BP16 protein fusions. Additional domains that may form part of a fusion protein comprising a CRISPR enzyme are described in US 20110059502, incorporated herein by reference.

D. Therapeutic Proteins

Some embodiments concern expression of recombinant proteins and polypeptides. In some aspects, the protein or polypeptide may be modified to increase serum stability. Thus, when the present application refers to the function or activity of "modified protein" or a "modified polypeptide," one of ordinary skill in the art would understand that this includes, for example, a protein or polypeptide that possesses an additional advantage over the unmodified protein or polypeptide. It is specifically contemplated that embodiments concerning a "modified protein" may be implemented with respect to a "modified polypeptide," and vice versa.

Recombinant proteins may possess deletions and/or substitutions of amino acids; thus, a protein with a deletion, a protein with a substitution, and a protein with a deletion and a substitution are modified proteins. In some embodiments, these proteins may further include insertions or added amino acids, such as with fusion proteins or proteins with linkers, for example. A "modified deleted protein" lacks one or more residues of the native protein, but may possess the specificity and/or activity of the native protein. A "modified deleted protein" may also have reduced immunogenicity or antigenicity. An example of a modified deleted protein is one that has an amino acid residue deleted from at least one antigenic region, i.e. a region of the protein determined to be antigenic in a particular organism, such as the organism to which the modified protein is being administered.

Substitution or replacement variants typically contain the exchange of one amino acid for another at one or more sites within the protein and may be designed to modulate one or more properties of the polypeptide, particularly its effector functions and/or bioavailability. Substitutions may or may not be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate;

glycine to proline; histidine to asparagine or glutamine; isoleucine to leucine or valine; leucine to valine or isoleucine; lysine to arginine; methionine to leucine or isoleucine; phenylalanine to tyrosine, leucine, or methionine; serine to threonine; threonine to serine; tryptophan to tyrosine; tyrosine to tryptophan or phenylalanine; and valine to isoleucine or leucine.

In addition to a deletion or substitution, a modified protein may possess an insertion of residues, which typically involves the addition of at least one residue in the polypeptide. This may include the insertion of a targeting peptide or polypeptide or simply a single residue. Terminal additions, called fusion proteins, are discussed below.

The term "biologically functional equivalent" is well understood in the art and is further defined in detail herein. Accordingly, sequences that have between about 70% and about 80%, or between about 81% and about 90%, or even between about 91% and about 99% of amino acids that are identical or functionally equivalent to the amino acids of a control polypeptide are included, provided the biological activity of the protein is maintained. A recombinant protein may be biologically functionally equivalent to its native counterpart in certain aspects.

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

As used herein, a protein or peptide generally refers, but is not limited to, a protein of greater than about 200 amino acids, up to a full-length sequence translated from a gene; a polypeptide of greater than about 100 amino acids; and/or a peptide of from about 3 to about 100 amino acids. For convenience, the terms "protein," "polypeptide," and "peptide are used interchangeably herein.

As used herein, an "amino acid residue" refers to any naturally occurring amino acid, any amino acid derivative, or any amino acid mimic known in the art. In certain embodiments, the residues of the protein or peptide are sequential, without any non-amino acids interrupting the sequence of amino acid residues. In other embodiments, the sequence may comprise one or more non-amino acid moieties. In particular embodiments, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid.

Certain embodiments of the present invention concern fusion proteins. These molecules may have a therapeutic protein linked at the N- or C-terminus to a heterologous domain. For example, fusions may also employ leader sequences from other species to permit the recombinant expression of a protein in a heterologous host. Another useful fusion includes the addition of a protein affinity tag, such as a serum albumin affinity tag or six histidine residues, or an immunologically active domain, such as an antibody epitope, preferably cleavable, to facilitate purification of the fusion protein. Non-limiting affinity tags include polyhistidine, chitin binding protein (CBP), maltose binding protein (MBP), and glutathione-S-transferase (GST).

Methods of generating fusion proteins are well known to those of skill in the art. Such proteins can be produced, for example, by de novo synthesis of the complete fusion protein, or by attachment of the DNA sequence encoding the heterologous domain, followed by expression of the intact fusion protein.

Production of fusion proteins that recover the functional activities of the parent proteins may be facilitated by connecting genes with a bridging DNA segment encoding a peptide linker that is spliced between the polypeptides connected in tandem. The linker would be of sufficient length to allow proper folding of the resulting fusion protein.

III. METHODS OF ADMINISTRATION

Viral vectors in some aspects may be administered directly to patients (in vivo) or they can be used to treat cells in vitro or ex vivo, and then administered to patients. The term "vector" refers to small carrier nucleic acid molecule, a plasmid, virus (e.g., AAV vector, retroviral vector, lentiviral vector), or other vehicle that can be manipulated by insertion or incorporation of a nucleic acid. Vectors, such as viral vectors, can be used to introduce/transfer nucleic acid sequences into cells, such that the nucleic acid sequence therein is transcribed and, if encoding a protein, subsequently translated by the cells.

Any suitable cell or mammal can be administered or treated by a method or use described herein. Typically, a mammal in need of a method described herein is suspected of having or expressing an abnormal or aberrant protein that is associated with a disease state. Alternative, the mammalian recipient may have a condition that is amenable to gene replacement therapy. As used herein, "gene replacement therapy" refers to administration to the recipient of exogenous genetic material encoding a therapeutic agent and subsequent expression of the administered genetic material in situ. Thus, the phrase "condition amenable to gene replacement therapy" embraces conditions such as genetic diseases (i.e., a disease condition that is attributable to one or more gene defects), acquired pathologies (i.e., a pathological condition which is not attributable to an inborn defect), cancers and prophylactic processes (i.e., prevention of a disease or of an undesired medical condition). Accordingly, as used herein, the term "therapeutic agent" refers to any agent or material, which has a beneficial effect on the mammalian recipient. Thus, "therapeutic agent" embraces both therapeutic and prophylactic molecules having nucleic acid or protein components.

Non-limiting examples of mammals include humans, non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). In certain embodiments a mammal is a human. In certain embodiments a mammal is a non-rodent mammal (e.g., human, pig, goat, sheep, horse, dog, or the like). In certain embodiments a non-rodent mammal is a human. A mammal can be any age or at any stage of development (e.g., an adult, teen, child, infant, or a mammal in utero). A mammal can be male or female. In certain embodiments a mammal can be an animal disease model, for example, animal models having or expressing an abnormal or aberrant protein that is associated with a disease state or animal models with insufficient expression of a protein, which causes a disease state.

Mammals (subjects) treated by a method or composition described herein include adults (18 years or older) and children (less than 18 years of age). Adults include the elderly. Representative adults are 50 years or older. Children range in age from 1-2 years old, or from 2-4, 4-6, 6-18, 8-10, 10-12, 12-15 and 15-18 years old. Children also include infants. Infants typically range from 1-12 months of age.

In certain embodiments, a method includes administering a plurality of viral particles to a mammal as set forth herein, where severity, frequency, progression or time of onset of one or more symptoms of a disease state, such as a neuro-degenerative disease, decreased, reduced, prevented, inhibited or delayed. In certain embodiments, a method includes administering a plurality of viral particles to a mammal to treat an adverse symptom of a disease state, such as a neuro-degenerative disease. In certain embodiments, a method includes administering a plurality of viral particles to a mammal to stabilize, delay or prevent worsening, or progression, or reverse and adverse symptom of a disease state, such as a neuro-degenerative disease.

In certain embodiments a method includes administering a plurality of viral particles to the central nervous system, or portion thereof as set forth herein, of a mammal and severity, frequency, progression or time of onset of one or more symptoms of a disease state, such as a neuro-degenerative disease, are decreased, reduced, prevented, inhibited or delayed by at least about 5 to about 10, about 10 to about 25, about 25 to about 50, or about 50 to about 100 days.

In certain embodiments, a symptom or adverse effect comprises an early stage, middle or late stage symptom; a behavior, personality or language symptom; swallowing, movement, seizure, tremor or fidgeting symptom; ataxia; and/or a cognitive symptom such as memory, ability to organize.

IV. PHARMACEUTICAL COMPOSITIONS

As used herein the term "pharmaceutically acceptable" and "physiologically acceptable" mean a biologically acceptable composition, formulation, liquid or solid, or mixture thereof, which is suitable for one or more routes of administration, in vivo delivery or contact. A "pharmaceutically acceptable" or "physiologically acceptable" composition is a material that is not biologically or otherwise undesirable, e.g., the material may be administered to a subject without causing substantial undesirable biological effects. Such composition, "pharmaceutically acceptable" and "physiologically acceptable" formulations and compositions can be sterile. Such pharmaceutical formulations and compositions may be used, for example in administering a viral particle to a subject.

Such formulations and compositions include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Supplementary active compounds (e.g., preservatives, antibacterial, antiviral and antifungal agents) can also be incorporated into the formulations and compositions.

Pharmaceutical compositions typically contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, Tween80, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as surfactants, wetting or emulsifying agents, pH buffering substances, and the like, may be present in such vehicles.

Pharmaceutical compositions can be formulated to be compatible with a particular route of administration or delivery, as set forth herein or known to one of skill in the art. Thus, pharmaceutical compositions include carriers, diluents, or excipients suitable for administration or delivery by various routes.

Pharmaceutical forms suitable for injection or infusion of viral particles can include sterile aqueous solutions or dispersions which are adapted for the extemporaneous preparation of sterile injectable or infusible solutions or dispersions, optionally encapsulated in liposomes. In all cases, the ultimate form should be a sterile fluid and stable under the conditions of manufacture, use and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Isotonic agents, for example, sugars, buffers or salts (e.g., sodium chloride) can be included. Prolonged absorption of injectable compositions can be brought about by the use in the compositions of agents delaying absorption, for example, aluminum monostearate and gelatin.

Solutions or suspensions of viral particles can optionally include one or more of the following components: a sterile diluent such as water for injection, saline solution, such as phosphate buffered saline (PBS), artificial CSF, a surfactants, fixed oils, a polyol (for example, glycerol, propylene glycol, and liquid polyethylene glycol, and the like), glycerin, or other synthetic solvents; antibacterial and antifungal agents such as parabens, chlorobutanol, phenol, ascorbic acid, and the like; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose.

Pharmaceutical formulations, compositions and delivery systems appropriate for the compositions, methods and uses of the invention are known in the art (see, e.g., Remington: The Science and Practice of Pharmacy (2003) $20^{th}$ ed., Mack Publishing Co., Easton, PA; Remington's Pharmaceutical Sciences (1990) $18^{th}$ ed., Mack Publishing Co., Easton, PA; The Merck Index (1996) $12^{th}$ ed., Merck Publishing Group, Whitehouse, NJ; Pharmaceutical Principles of Solid Dosage Forms (1993), Technonic Publishing Co., Inc., Lancaster, Pa.; Ansel and Stoklosa, Pharmaceutical Calculations (2001) $11^{th}$ ed., Lippincott Williams & Wilkins, Baltimore, MD; and Poznansky et al., Drug Delivery Systems (1980), R. L. Juliano, ed., Oxford, N.Y., pp. 253-315).

Viral particles and their compositions may be formulated in dosage unit form for ease of administration and uniformity of dosage. Dosage unit form as used herein refers to physically discrete units suited as unitary dosages for an individual to be treated; each unit containing a predetermined quantity of active compound calculated to produce the desired therapeutic effect in association with the required pharmaceutical carrier. The dosage unit forms are dependent upon the number of viral particles believed necessary to produce the desired effect(s). The amount necessary can be formulated in a single dose, or can be formulated in multiple dosage units. The dose may be adjusted to a suitable viral particle concentration, optionally combined with an anti-inflammatory agent, and packaged for use.

In one embodiment, pharmaceutical compositions will include sufficient genetic material to provide a therapeutically effective amount, i.e., an amount sufficient to reduce or ameliorate symptoms or an adverse effect of a disease state in question or an amount sufficient to confer the desired benefit.

A "unit dosage form" as used herein refers to physically discrete units suited as unitary dosages for the subject to be treated; each unit containing a predetermined quantity optionally in association with a pharmaceutical carrier (excipient, diluent, vehicle or filling agent) which, when administered in one or more doses, is calculated to produce a desired effect (e.g., prophylactic or therapeutic effect). Unit dosage forms may be within, for example, ampules and vials, which may include a liquid composition, or a composition in a freeze-dried or lyophilized state; a sterile liquid carrier, for example, can be added prior to administration or delivery in vivo. Individual unit dosage forms can be included in multi-dose kits or containers. Thus, for example, viral particles, and pharmaceutical compositions thereof, can be packaged in single or multiple unit dosage form for ease of administration and uniformity of dosage.

Formulations containing viral particles typically contain an effective amount, the effective amount being readily determined by one skilled in the art. The viral particles may typically range from about 1% to about 95% (w/w) of the composition, or even higher if suitable. The quantity to be administered depends upon factors such as the age, weight and physical condition of the mammal or the human subject considered for treatment. Effective dosages can be established by one of ordinary skill in the art through routine trials establishing dose response curves.

V. DEFINITIONS

The terms "polynucleotide," "nucleic acid" and "transgene" are used interchangeably herein to refer to all forms of nucleic acid, oligonucleotides, including deoxyribonucleic acid (DNA) and ribonucleic acid (RNA) and polymers thereof.

Polynucleotides include genomic DNA, cDNA and antisense DNA, and spliced or unspliced mRNA, rRNA, tRNA and inhibitory DNA or RNA (RNAi, e.g., small or short hairpin (sh)RNA, microRNA (miRNA), small or short interfering (si)RNA, trans-splicing RNA, or antisense RNA). Polynucleotides can include naturally occurring, synthetic, and intentionally modified or altered polynucleotides (e.g., variant nucleic acid). Polynucleotides can be single stranded, double stranded, or triplex, linear or circular, and can be of any suitable length. In discussing polynucleotides, a sequence or structure of a particular polynucleotide may be described herein according to the convention of providing the sequence in the 5' to 3' direction.

A nucleic acid encoding a polypeptide often comprises an open reading frame that encodes the polypeptide. Unless otherwise indicated, a particular nucleic acid sequence also includes degenerate codon substitutions.

Nucleic acids can include one or more expression control or regulatory elements operably linked to the open reading frame, where the one or more regulatory elements are configured to direct the transcription and translation of the polypeptide encoded by the open reading frame in a mammalian cell. Non-limiting examples of expression control/regulatory elements include transcription initiation sequences (e.g., promoters, enhancers, a TATA box, and the like), translation initiation sequences, mRNA stability sequences, poly A sequences, secretory sequences, and the like. Expression control/regulatory elements can be obtained from the genome of any suitable organism.

A "promoter" refers to a nucleotide sequence, usually upstream (5') of a coding sequence, which directs and/or controls the expression of the coding sequence by providing the recognition for RNA polymerase and other factors required for proper transcription. A pol II promoter includes a minimal promoter that is a short DNA sequence comprised of a TATA-box and optionally other sequences that serve to specify the site of transcription initiation, to which regulatory elements are added for control of expression. A type 1 pol III promoter includes three cis-acting sequence elements downstream of the transcriptional start site: a) 5'sequence element (A block); b) an intermediate sequence element (I block); c) 3' sequence element (C block). A type 2 pol III promoter includes two essential cis-acting sequence elements downstream of the transcription start site: a) an A box (5' sequence element); and b) a B box (3' sequence element). A type 3 pol III promoter includes several cis-acting promoter elements upstream of the transcription start site, such as a traditional TATA box, proximal sequence element (PSE), and a distal sequence element (DSE).

An "enhancer" is a DNA sequence that can stimulate transcription activity and may be an innate element of the promoter or a heterologous element that enhances the level or tissue specificity of expression. It is capable of operating in either orientation (5'→3' or 3'→5'), and may be capable of functioning even when positioned either upstream or downstream of the promoter.

Promoters and/or enhancers may be derived in their entirety from a native gene, or be composed of different elements derived from different elements found in nature, or even be comprised of synthetic DNA segments. A promoter or enhancer may comprise DNA sequences that are involved in the binding of protein factors that modulate/control effectiveness of transcription initiation in response to stimuli, physiological or developmental conditions.

Non-limiting examples of promoters include SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, pol II promoters, pol III promoters, synthetic promoters, hybrid promoters, and the like. In addition, sequences derived from non-viral genes, such as the murine metallothionein gene, will also find use herein. Exemplary constitutive promoters include the promoters for the following genes which encode certain constitutive or "housekeeping" functions: hypoxanthine phosphoribosyl transferase (HPRT), dihydrofolate reductase (DHFR), adenosine deaminase, phosphoglycerol kinase (PGK), pyruvate kinase, phosphoglycerol mutase, actin promoter, U6, and other constitutive promoters known to those of skill in the art. In addition, many viral promoters function constitutively in eukaryotic cells. These include:

the early and late promoters of SV40; the long terminal repeats (LTRs) of Moloney Leukemia Virus and other retroviruses; and the thymidine kinase promoter of Herpes Simplex Virus, among many others. In addition, sequences derived from intronic miRNA promoters, such as, for example, the miR107, miR206, miR208b, miR548f-2, miR569, miR590, miR566, and miR128 promoter, will also find use herein (see, e.g., Monteys et al., 2010). Accordingly, any of the above-referenced constitutive promoters can be used to control transcription of a heterologous gene insert.

A “transgene” is used herein to conveniently refer to a nucleic acid sequence/polynucleotide that is intended or has been introduced into a cell or organism. Transgenes include any nucleic acid, such as a gene that encodes an inhibitory RNA or polypeptide or protein, and are generally heterologous with respect to naturally occurring AAV genomic sequences.

The term “transduce” refers to introduction of a nucleic acid sequence into a cell or host organism by way of a vector (e.g., a viral particle). Introduction of a transgene into a cell by a viral particle is can therefore be referred to as “transduction” of the cell. The transgene may or may not be integrated into genomic nucleic acid of a transduced cell. If an introduced transgene becomes integrated into the nucleic acid (genomic DNA) of the recipient cell or organism it can be stably maintained in that cell or organism and further passed on to or inherited by progeny cells or organisms of the recipient cell or organism. Finally, the introduced transgene may exist in the recipient cell or host organism extra chromosomally, or only transiently. A “transduced cell” is therefore a cell into which the transgene has been introduced by way of transduction. Thus, a “transduced” cell is a cell into which, or a progeny thereof in which a transgene has been introduced. A transduced cell can be propagated, transgene transcribed and the encoded inhibitory RNA or protein expressed. For gene therapy uses and methods, a transduced cell can be in a mammal.

Transgenes under control of inducible promoters are expressed only or to a greater degree, in the presence of an inducing agent, (e.g., transcription under control of the metallothionein promoter is greatly increased in presence of certain metal ions). Inducible promoters include responsive elements (REs) which stimulate transcription when their inducing factors are bound. For example, there are REs for serum factors, steroid hormones, retinoic acid and cyclic AMP. Promoters containing a particular RE can be chosen in order to obtain an inducible response and in some cases, the RE itself may be attached to a different promoter, thereby conferring inducibility to the recombinant gene. Thus, by selecting a suitable promoter (constitutive versus inducible; strong versus weak), it is possible to control both the existence and level of expression of a polypeptide in the genetically modified cell. If the gene encoding the polypeptide is under the control of an inducible promoter, delivery of the polypeptide in situ is triggered by exposing the genetically modified cell in situ to conditions for permitting transcription of the polypeptide, e.g., by intraperitoneal injection of specific inducers of the inducible promoters which control transcription of the agent. For example, in situ expression by genetically modified cells of a polypeptide encoded by a gene under the control of the metallothionein promoter, is enhanced by contacting the genetically modified cells with a solution containing the appropriate (i.e., inducing) metal ions in situ.

A nucleic acid/transgene is “operably linked” when it is placed into a functional relationship with another nucleic acid sequence. A nucleic acid/transgene encoding and RNAi or a polypeptide, or a nucleic acid directing expression of a polypeptide may include an inducible promoter, or a tissue-specific promoter for controlling transcription of the encoded polypeptide. A nucleic acid operably linked to an expression control element can also be referred to as an expression cassette.

In certain embodiments, CNS-specific or inducible promoters, enhancers and the like, are employed in the methods and uses described herein. Non-limiting examples of CNS-specific promoters include those isolated from the genes from myelin basic protein (MBP), glial fibrillary acid protein (GFAP), and neuron specific enolase (NSE). Non-limiting examples of inducible promoters include DNA responsive elements for ecdysone, tetracycline, hypoxia and IFN.

In certain embodiments, an expression control element comprises a CMV enhancer. In certain embodiments, an expression control element comprises a beta actin promoter. In certain embodiments, an expression control element comprises a chicken beta actin promoter. In certain embodiments, an expression control element comprises a CMV enhancer and a chicken beta actin promoter.

As used herein, the terms “modify” or “variant” and grammatical variations thereof, mean that a nucleic acid, polypeptide or subsequence thereof deviates from a reference sequence. Modified and variant sequences may therefore have substantially the same, greater or less expression, activity or function than a reference sequence, but at least retain partial activity or function of the reference sequence. A particular type of variant is a mutant protein, which refers to a protein encoded by a gene having a mutation, e.g., a missense or nonsense mutation.

A “nucleic acid” or “polynucleotide” variant refers to a modified sequence which has been genetically altered compared to wild-type. The sequence may be genetically modified without altering the encoded protein sequence. Alternatively, the sequence may be genetically modified to encode a variant protein. A nucleic acid or polynucleotide variant can also refer to a combination sequence which has been codon modified to encode a protein that still retains at least partial sequence identity to a reference sequence, such as wild-type protein sequence, and also has been codon-modified to encode a variant protein. For example, some codons of such a nucleic acid variant will be changed without altering the amino acids of a protein encoded thereby, and some codons of the nucleic acid variant will be changed which in turn changes the amino acids of a protein encoded thereby.

The terms “protein” and “polypeptide” are used interchangeably herein. The “polypeptides” encoded by a “nucleic acid” or “polynucleotide” or “transgene” disclosed herein include partial or full-length native sequences, as with naturally occurring wild-type and functional polymorphic proteins, functional subsequences (fragments) thereof, and sequence variants thereof, so long as the polypeptide retains some degree of function or activity. Accordingly, in methods and uses of the invention, such polypeptides encoded by nucleic acid sequences are not required to be identical to the endogenous protein that is defective, or whose activity, function, or expression is insufficient, deficient or absent in a treated mammal.

Non-limiting examples of modifications include one or more nucleotide or amino acid substitutions (e.g., about 1 to about 3, about 3 to about 5, about 5 to about 10, about 10 to about 15, about 15 to about 20, about 20 to about 25, about 25 to about 30, about 30 to about 40, about 40 to about 50, about 50 to about 100, about 100 to about 150, about 150 to about 200, about 200 to about 250, about 250 to about 500, about 500 to about 750, about 750 to about 1000 or more nucleotides or residues).

An example of an amino acid modification is a conservative amino acid substitution or a deletion. In particular embodiments, a modified or variant sequence retains at least part of a function or activity of the unmodified sequence (e.g., wild-type sequence).

Another example of an amino acid modification is a targeting peptide introduced into a capsid protein of a viral particle. Peptides have been identified that target recombinant viral vectors, to the central nervous system, such as to distinct brain regions.

A recombinant virus so modified may preferentially bind to one type of tissue (e.g., CNS tissue) over another type of tissue (e.g., liver tissue). In certain embodiments, a recombinant virus bearing a modified capsid protein may "target" brain vascular epithelia tissue by binding at level higher than a comparable, unmodified capsid protein. For example, a recombinant virus having a modified capsid protein may bind to brain vascular epithelia tissue at a level 50% to 100% greater than an unmodified recombinant virus.

A "nucleic acid fragment" is a portion of a given nucleic acid molecule. Deoxyribonucleic acid (DNA) in the majority of organisms is the genetic material while ribonucleic acid (RNA) is involved in the transfer of information contained within DNA into proteins. Fragments and variants of the disclosed nucleotide sequences and proteins or partial-length proteins encoded thereby are also encompassed by the present invention. By "fragment" or "portion" is meant a full length or less than full length of the nucleotide sequence encoding, or the amino acid sequence of, a polypeptide or protein. In certain embodiments, the fragment or portion is biologically functional (i.e., retains 5%, 10%, 15%, 20%, 25%, 30%, 35%, 40%, 45%, 50%, 55%, 60%, 65%, 70%, 75%, 80%, 85%, 90%, 95%, 99% or 100% of activity or function of wild-type).

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of molecular biology techniques, as, for example, with polymerase chain reaction (PCR) and hybridization techniques. Variant nucleotide sequences also include synthetically derived nucleotide sequences, such as those generated, for example, by using site-directed mutagenesis, which encode the native protein, as well as those that encode a polypeptide having amino acid substitutions. Generally, nucleotide sequence variants of the invention will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence. In certain embodiments, the variant is biologically functional (i.e., retains 5%, 10%, 15%, 20%, 25%, 30%, 35%, 40%, 45%, 50%, 55%, 60%, 65%, 70%, 75%, 80%, 85%, 90%, 95%, 99% or 100% of activity or function of wild-type).

"Conservative variations" of a particular nucleic acid sequence refers to those nucleic acid sequences that encode identical or essentially identical amino acid sequences. Because of the degeneracy of the genetic code, a large number of functionally identical nucleic acids encode any given polypeptide. For instance, the codons CGT, CGC, CGA, CGG, AGA and AGG all encode the amino acid arginine. Thus, at every position where an arginine is specified by a codon, the codon can be altered to any of the corresponding codons described without altering the encoded protein. Such nucleic acid variations are "silent variations," which are one species of "conservatively modified variations." Every nucleic acid sequence described herein that encodes a polypeptide also describes every possible silent variation, except where otherwise noted. One of skill in the art will recognize that each codon in a nucleic acid (except ATG, which is ordinarily the only codon for methionine) can be modified to yield a functionally identical molecule by standard techniques. Accordingly, each "silent variation" of a nucleic acid that encodes a polypeptide is implicit in each described sequence.

The term "substantial identity" of polynucleotide sequences means that a polynucleotide comprises a sequence that has at least 70%, 71%, 72%, 73%, 74%, 75%, 76%, 77%, 78%, or 79%, or at least 80%, 81%, 82%, 83%, 84%, 85%, 86%, 87%, 88%, or 89%, or at least 90%, 91%, 92%, 93%, or 94%, or even at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, or even at least 95%.

The term "substantial identity" in the context of a polypeptide indicates that a polypeptide comprises a sequence with at least 70%, 71%, 72%, 73%, 74%, 75%, 76%, 77%, 78%, or 79%, or 80%, 81%, 82%, 83%, 84%, 85%, 86%, 87%, 88%, or 89%, or at least 90%, 91%, 92%, 93%, or 94%, or even, 95%, 96%, 97%, 98% or 99%, sequence identity to the reference sequence over a specified comparison window. An indication that two polypeptide sequences are identical is that one polypeptide is immunologically reactive with antibodies raised against the second polypeptide. Thus, a polypeptide is identical to a second polypeptide, for example, where the two peptides differ only by a conservative substitution.

The terms "treat" and "treatment" refer to both therapeutic treatment and prophylactic or preventative measures, wherein the object is to prevent, inhibit, reduce, or decrease an undesired physiological change or disorder, such as the development, progression or worsening of the disorder. For purposes of this invention, beneficial or desired clinical results include, but are not limited to, alleviation of symptoms, diminishment of extent of disease, stabilizing a (i.e., not worsening or progressing) symptom or adverse effect of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those predisposed (e.g., as determined by a genetic assay).

VI. KITS

The invention provides kits with packaging material and one or more components therein. A kit typically includes a label or packaging insert including a description of the components or instructions for use in vitro, in vivo, or ex vivo, of the components therein. A kit can contain a collection of such components, e.g., a nucleic acid, recombinant vector, and/or viral particles.

A kit refers to a physical structure housing one or more components of the kit. Packaging material can maintain the components sterilely, and can be made of material commonly used for such purposes (e.g., paper, corrugated fiber, glass, plastic, foil, ampules, vials, tubes, etc.).

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer, lot numbers, manufacture location and date, expiration dates. Labels or inserts can include information identifying manufacturer information, lot numbers, manufacturer location and date. Labels or inserts can include information on a disease for which a kit component may be used. Labels or inserts can include instructions for the clinician or subject for using one or more of the kit components in a method, use, or treatment protocol or therapeutic regimen. Instructions can include dosage amounts, frequency or duration, and instructions for practicing any of the methods, uses, treatment protocols or prophylactic or therapeutic regimes described herein.

Labels or inserts can include information on any benefit that a component may provide, such as a prophylactic or therapeutic benefit. Labels or inserts can include information on potential adverse side effects, complications or reactions, such as warnings to the subject or clinician regarding situations where it would not be appropriate to use a particular composition. Adverse side effects or complications could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a bar-coded printed label, a disk, optical disk such as CD- or DVD-ROM/RAM, DVD, MP3, or an electrical storage media such as RAM and ROM or hybrids of these such as magnetic/optical storage media, FLASH memory, hybrids and memory type cards.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Identification of AAV Variants that Target Brain Parenchyma

Figure 3:
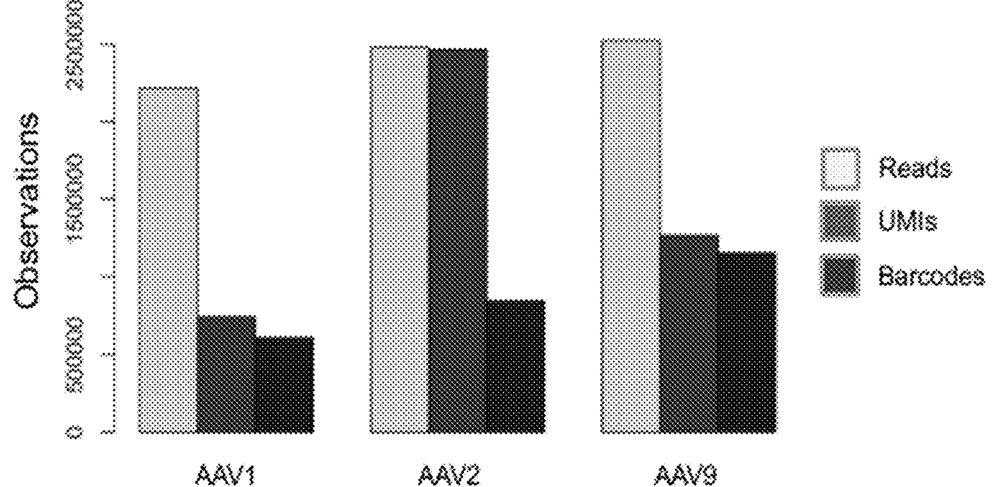
FIG. 3. Graphical representation of input library diversity. Diversity of the input viral library measured from aliquots of AAV1, AAV2, and AAV9 viral vector prior to Round1 ICV injection.

Advanced bar-coded AAV libraries were developed using AAV1, AAV2 and AAV9 capsids as starting platforms. AAV1, AAV2, and AAV9 peptide display libraries were generated by insertion of random sequences at position 590 of AAV1 capsid, position 587 of AAV2 capsid, and position 588 of AAV9 capsid, respectively (FIG. 1). The library had a diversity of $1\times10^7$ unique clones (FIG. 3).

To test the utility of the libraries, pilot studies were performed with bench-grade (low titer, low purity) capsid modified AAV2. The AAV2 library was injected intravenously into two C57BL/6 mice at $8\times10^{10}$ vector genomes per animal. After 72 hours, the cerebral cortex, cerebellum, and spinal cord were dissected. Of note, heart, skeletal muscle, and diaphragm were separately harvested in order to identify the muscle tropism. Viral genomic DNA was isolated, and the recovered random oligonucleotide sequences were amplified by PCR. The PCR products from brain were pooled to generate the second-round library, which was injected into two mice at $4\times10^{10}$ vector genomes per animal. After the second injection, vector genomes were recovered as before and were subjected to NexGen sequencing along with the starting library and P t round tissues. To test if sequences showing enrichment in brain tissues could indeed extend AAV2s reach to the brain, individual hits were cloned into the AAV2 capsid packaging plasmid, and eGFP-expressing AAV2s were generated. Bench-grade vectors were made, and $3\times10^{10}$ vector genomes of the AAV2-based capsid modified viruses were injected into mice. Four weeks later, eGFP fluorescence was seen in the brain, even for these low titer variants.

Figure 2:
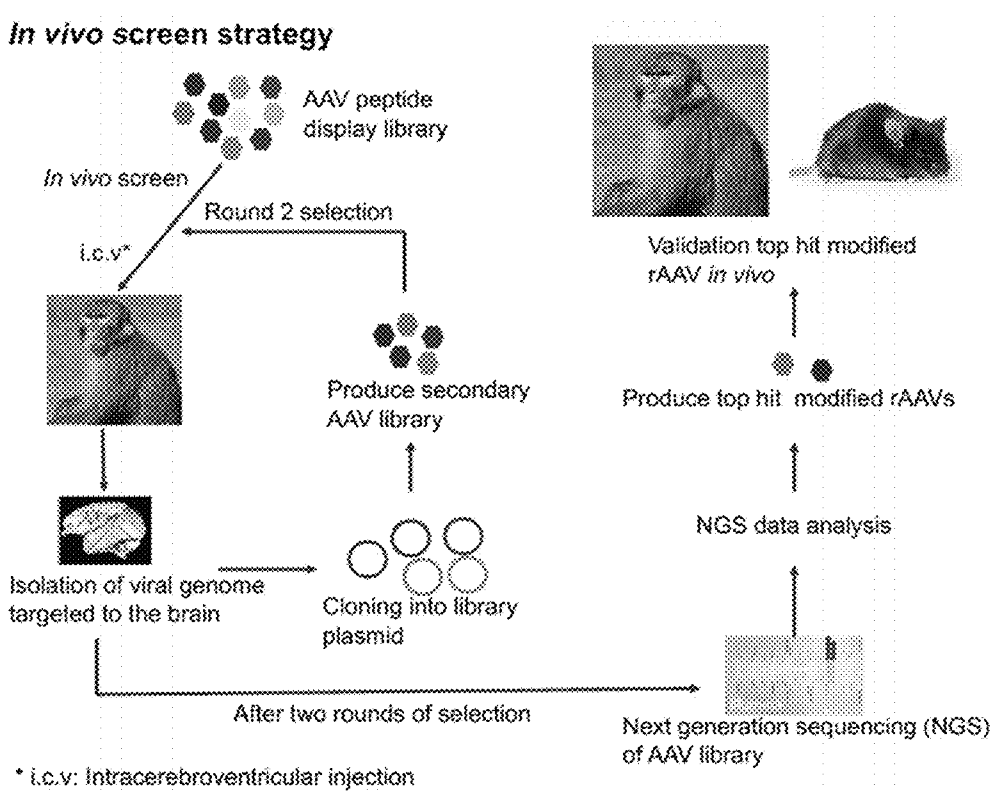
FIG. 2 In vivo screen strategy schematic.

Using these advanced bar-coded AAV libraries, AAV variants that can target distinct primate brain structures in non-human primates were identified. The AAV1, AAV2, and AAV9 libraries were delivered via intracerebroventricular injection to one non-human primate (FIG. 2). Seventy-two hours post-infusion, brain regions were microdissected for viral DNA isolation and AAV DNA amplified by PCR. Products were pooled and used for packaging the 2nd round library, which was infused into an additional NHP. Brain regions were then microdissected 12 days after infusion. After two rounds of panning, vector genomes were recovered and subjected to next generation sequencing. Specifically, genomic DNA extracted from the round1 and round2 tissues was PCR amplified to generate Illumina amplicon sequencing libraries at the position of the vector barcode. The resulting libraries were pooled and run on a single lane of an Illumina HiSeq 4000 using 100 bp single end read chemistry. To illustrate the utility of the approach, several target regions were tested as examples: the ependyma, the meninges and the cerebellum. In general, the sequences directing the AAVx to the ependyma, meninges and cerebellum were different, and different for the various serotypes.

Figure 4:
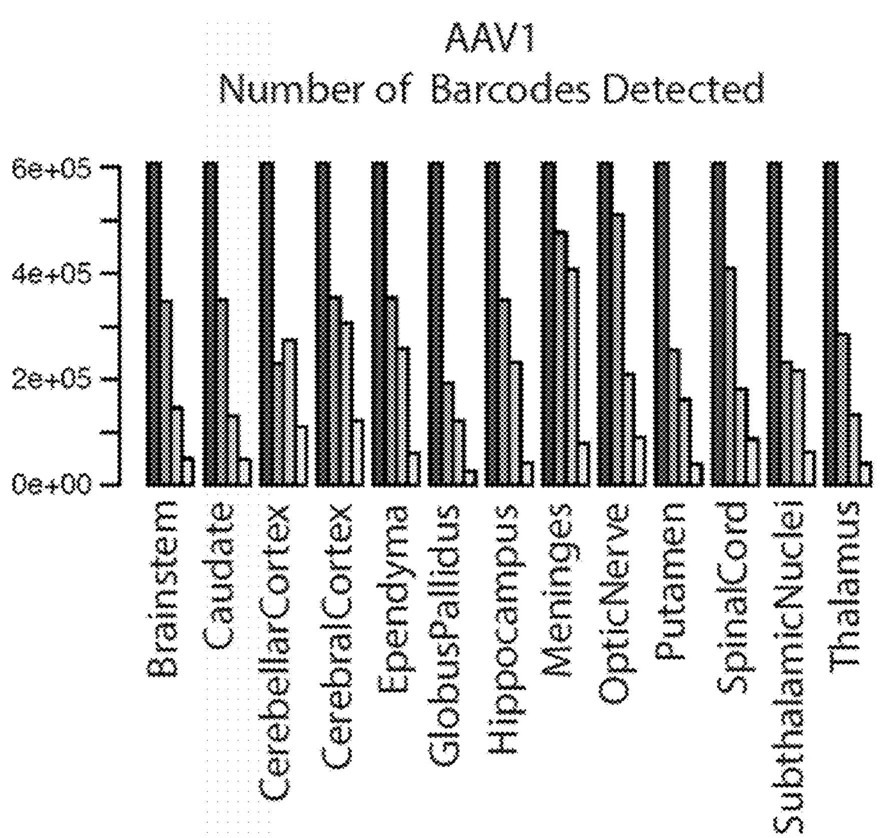
FIG. 4. Graphical representation of round-over-round barcode enrichment. The total number of unique barcodes recovered after Round 1 and Round 2 enrichment in Rhesus macaque for each tissue collected. Round 2 values for DNA and RNA are shown.
Figure 5:
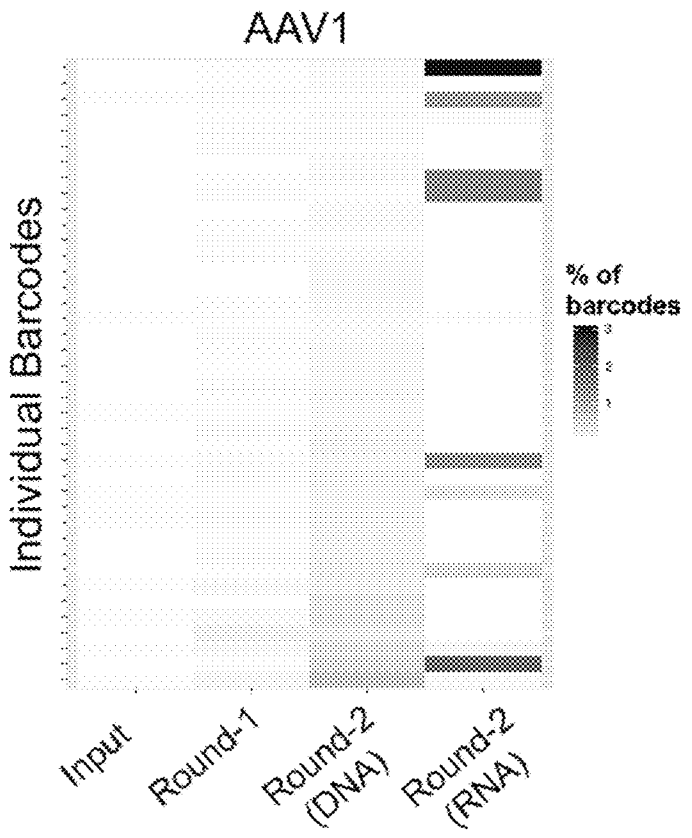
FIG. 5. Illustration of round-over-round enrichment of barcodes in AAV1, AAV2, and AAV9 serotypes for cerebellar cortex.
Figure 6:
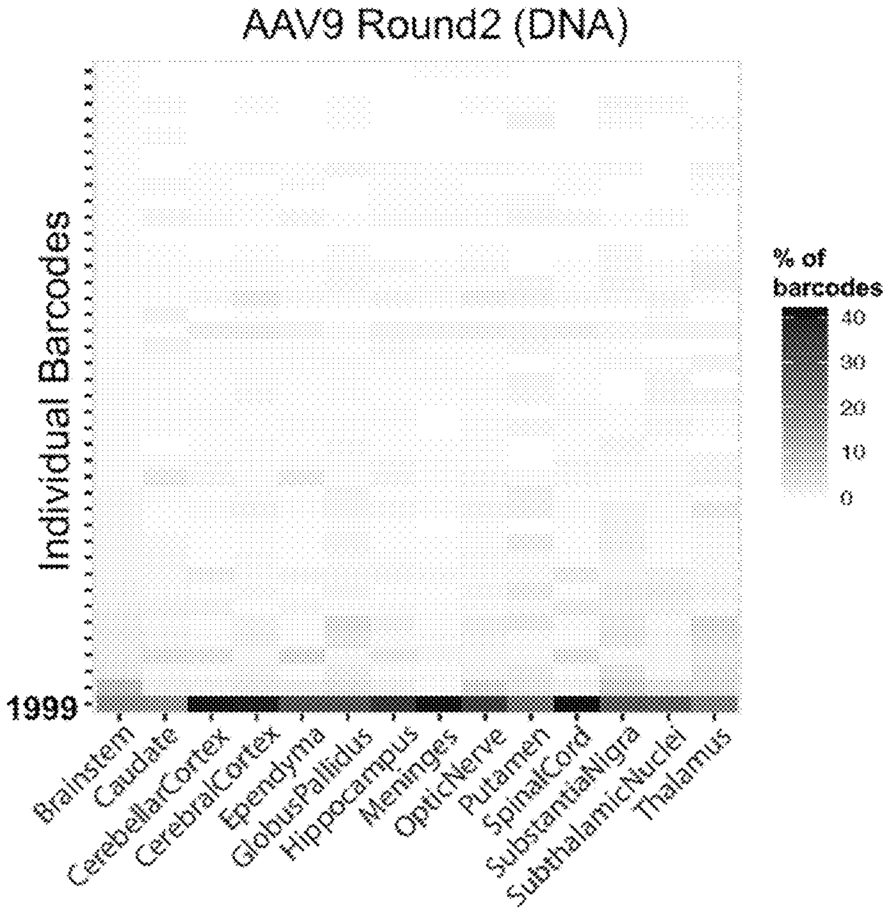
FIG. 6. Illustration of enrichment for AAV9 1999. Heatmap depictions of barcode enrichment from AAV9, cells are colored by the percentage of barcodes detected from the indicated tissue. Barcodes recovered from DNA are shown on the left while barcodes recovered from RNA are on the right.
Figure 7A:
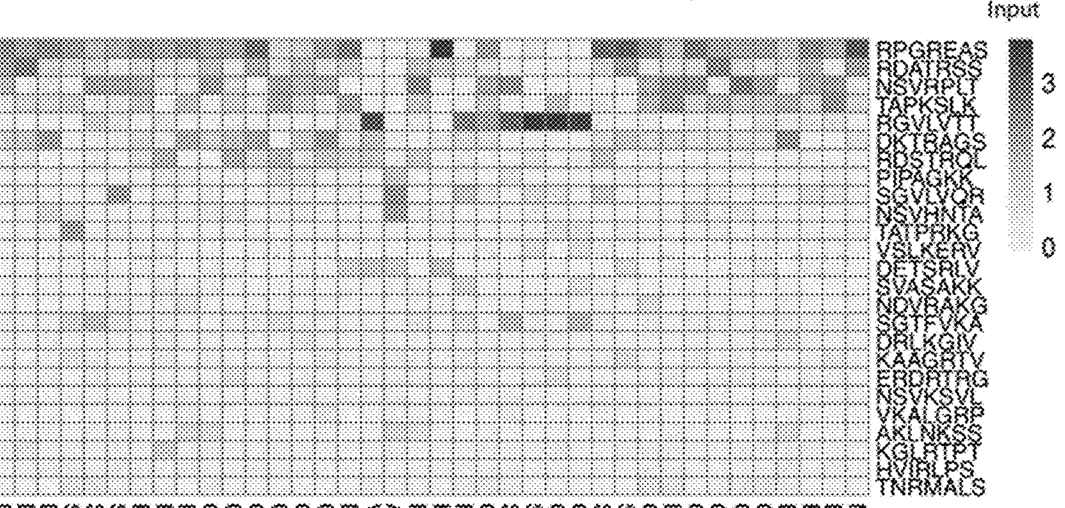
FIGS. 7A-C. Heatmap depictions of opool barcode enrichment from AAV1 (FIG. 7A), AAV2 (FIG. 7B), and AAV9 (FIG. 7C).
Figure 7B:
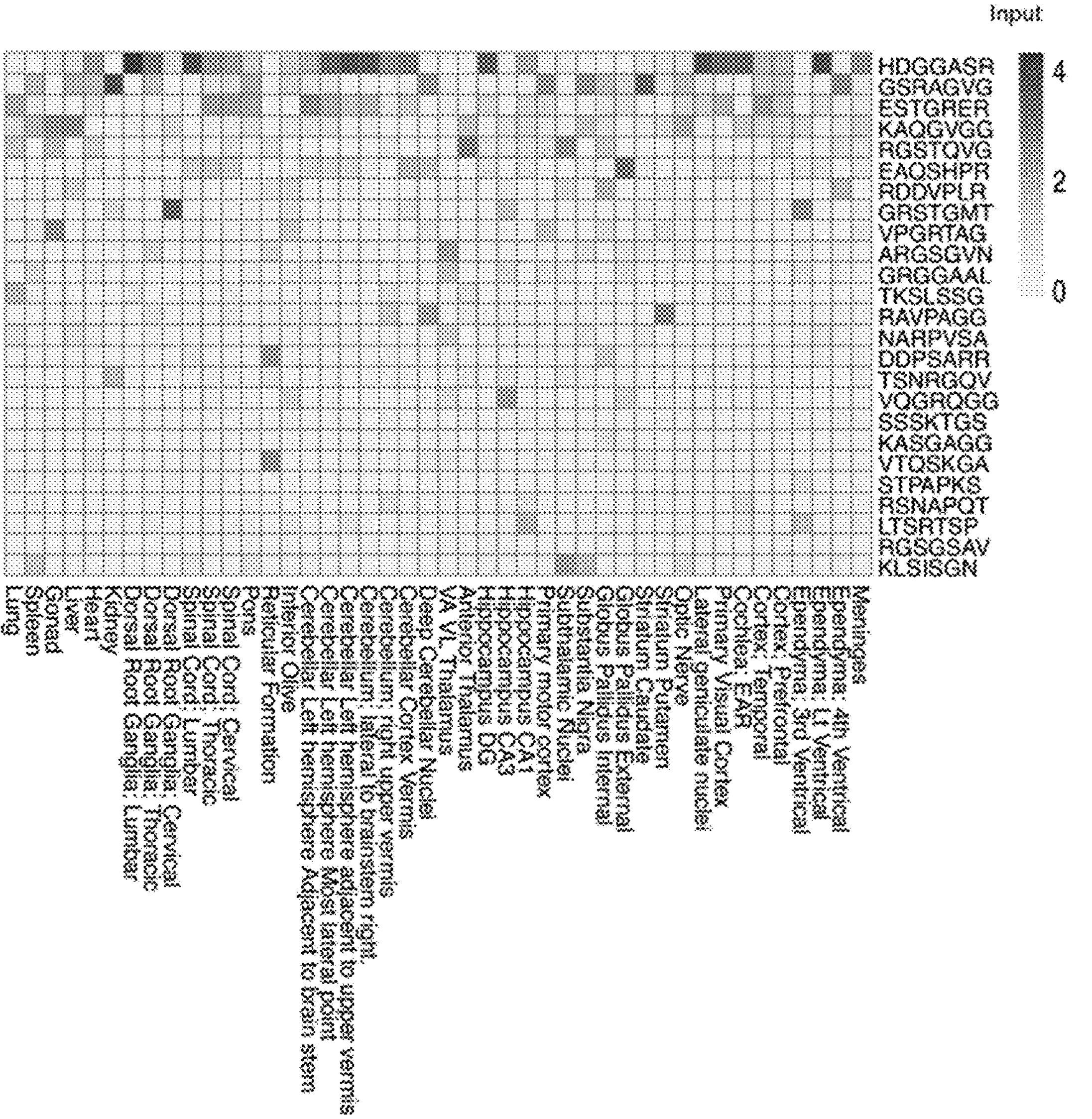
Figure 7C:
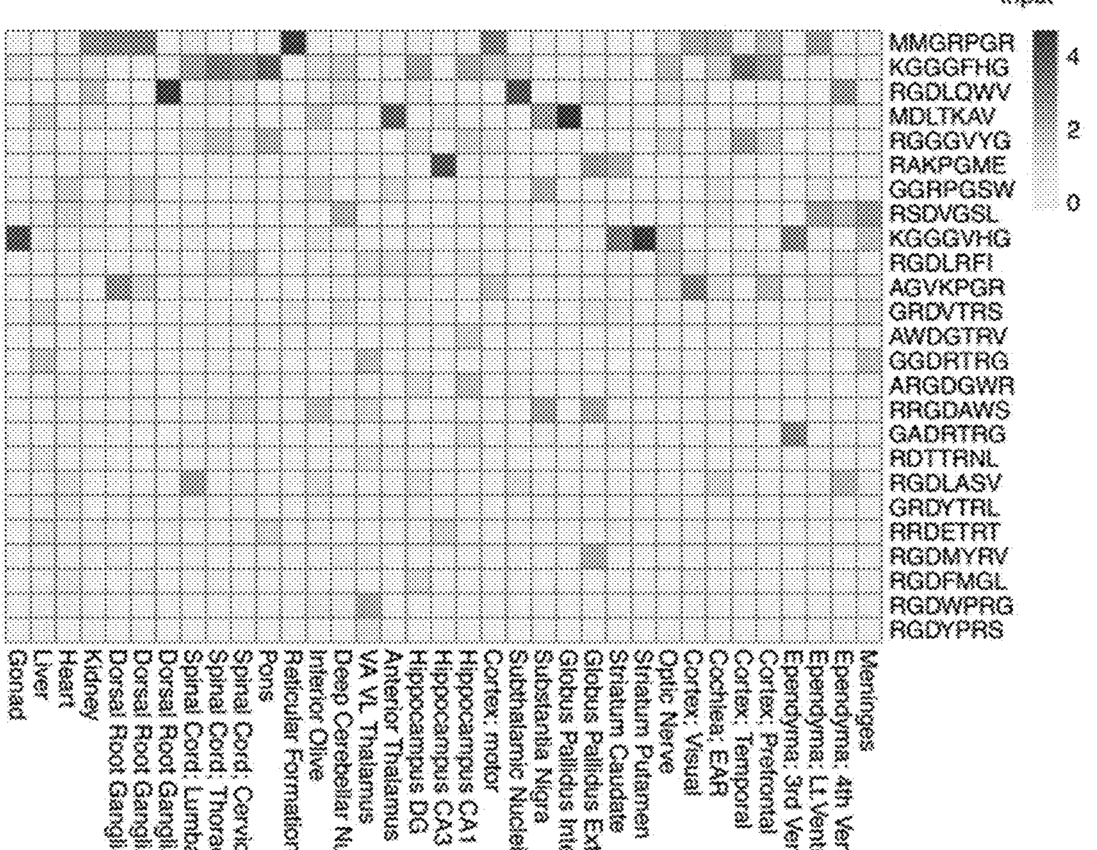

Round-over-Round enrichment graphs (FIG. 4) and heatmaps (FIGS. 5 and 6) were generated for the following tissues: brainstem, caudate, cerebellar cortex (FIG. 5), cerebral cortex, ependyma, globus pallidus, hippocampus, meninges, optic nerve, putamen, spinal cord, substantia nigra, subthalamic nuclei, and thalamus. These illustrate the enrichment of indicated barcodes at baseline (round 0), and after rounds one and two of in vivo passaging through rhesus macaque. To generate these, the fastq results files for each tissue and round combination were processed using a custom Python script designed to extract and quantify unique barcode configurations observed at the DNA level. A custom R script was used to calculate the percentages of barcodes present in each sample and convert DNA barcodes to amino acid barcodes. Table 1 corresponds to samples treated with the AAV1-derived library; Table 2 represents tissues treated with the AAV2-derived library; Table 3 corresponds to samples treated with the AAV9-derived library. Top hits were selected from these three libraries and were assembled and generated into a validation library containing 50 (AAV1), 58 (AAV2), and 30 (AAV9) derived barcodes. This validation library was delivered into an additional Rhesus macaque by ICV injection. Tissues were again collected and processed to facilitate recovery of barcode abundance by deep sequencing. Barcode abundance was evaluated in recovered tissues and the input viral library. Enrichment values for each barcode were calculated relative to their abundance in the input viral library. The resulting relative enrichment values are a robust indicator of vector performance amongst the various tissues evaluated, facilitating identification of broad and specific AAV vector variants (FIGS. 7A-C).

Figure 8:
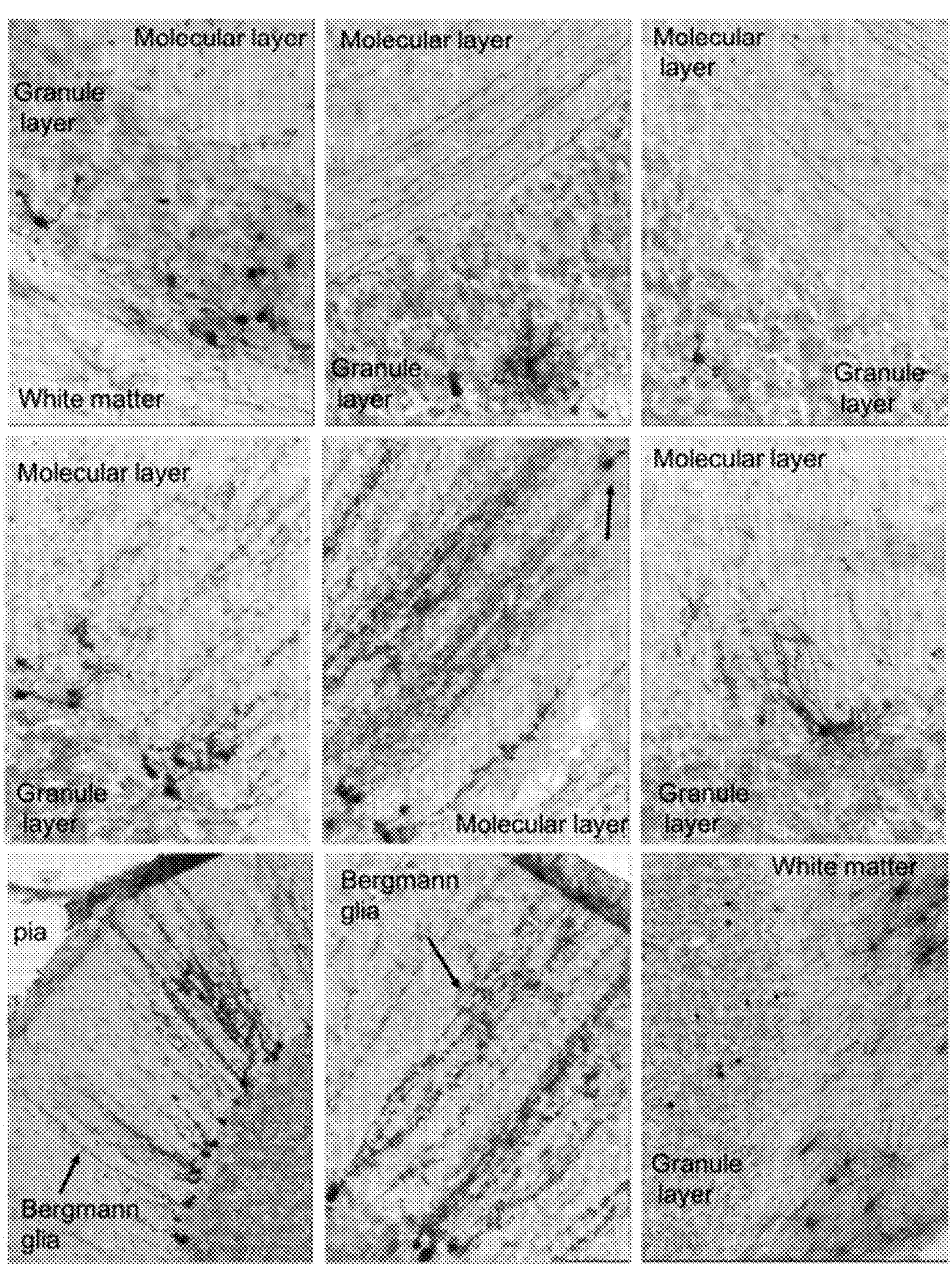
FIG. 8. AAV9 1999 in vivo Rhesus macaque validation. An eGFP expression construct was packaged into AAV9 1999 driven by the CAG promoter. 1.5E13 vg of AAV9 1999 was delivered to a 5 year old, female Rhesus macaque by ICV injection. Representative images of H&E stained cerebellum depicting the transduction pattern of AAV9 1999 are shown.

In order to validate the identified cell-type specificity, AAV9-1999 (having a targeting peptide sequence of KGGGFHG; SEQ ID NO: 110) was selected for in vivo validation. An eGFP expression construct was packaged into AAV9-1999 driven by the CAG promoter. A 5-year-old, female Rhesus macaque was administered 1.5E13 vg of AAV9-1999 by ICV injection to the left lateral ventricle. Brain was collected 30 days post-injection for histological analysis. Cerebellum slices were H&E stained to depict the transduction pattern of AAV9-1999 (FIG. 8). The cochlea were also collected from this animal and surprisingly had strong transduction of hair cells. In addition, AAV9-1999 and AAV9 capsids containing the eGFP construct were delivered to C57BL/6 p0 mouse pups by ICV injection at 1E10 vg per hemisphere. After 21 days, the mice were perfused. Whole mount brains (FIG. 9A), 40 μm whole brain sagittal sections (FIG. 9B), 40 μm 51 cortex sections (FIG. 9C, left), 40 μm hippocampus sections (FIG. 9C, middle), 40 μm cerebellum sagittal sections (FIG. 9C, right), and 40 μm lumbar spinal cord coronal sections (FIG. 9D) were imaged for eGFP fluorescence signal. AAV9-1999 injected into B1/6 neonate mouse pups showed ubiquitous expression greater than dose-matched injections of AAV9.

One adult rhesus macaque was injected with a mixture of four modified AAVs: AAV9 with a RGDLQWV (SEQ ID NO: 113) targeting peptide sequence and a mTAGBFP2 tag; AAV1 with a ERDRTRG (SEQ ID NO: 21) targeting peptide sequence as a mTFP1 tag; AAV2 with a GRGAPGG (SEQ ID NO: 80) targeting peptide sequence and a mNG tag; and AAV2 with a DDPSARR (SEQ ID NO: 53) targeting peptide sequence and a mRuby3 tag. The viruses were mixed straight at equal volumes to achieve the final total doses for each as follows:

| | |
|---|---|
| AAV9.RGDL mTagBFP2 | 6.13E12 total vg |
| AAV1.ERDR mTFP1 | 1.23E13 total vg |
| AAV2.GRGA mNG | 8.8E12 total vg |
| AAV2.DDPS mRuby3 | 1.32E13 total vg |

Figure 10A:
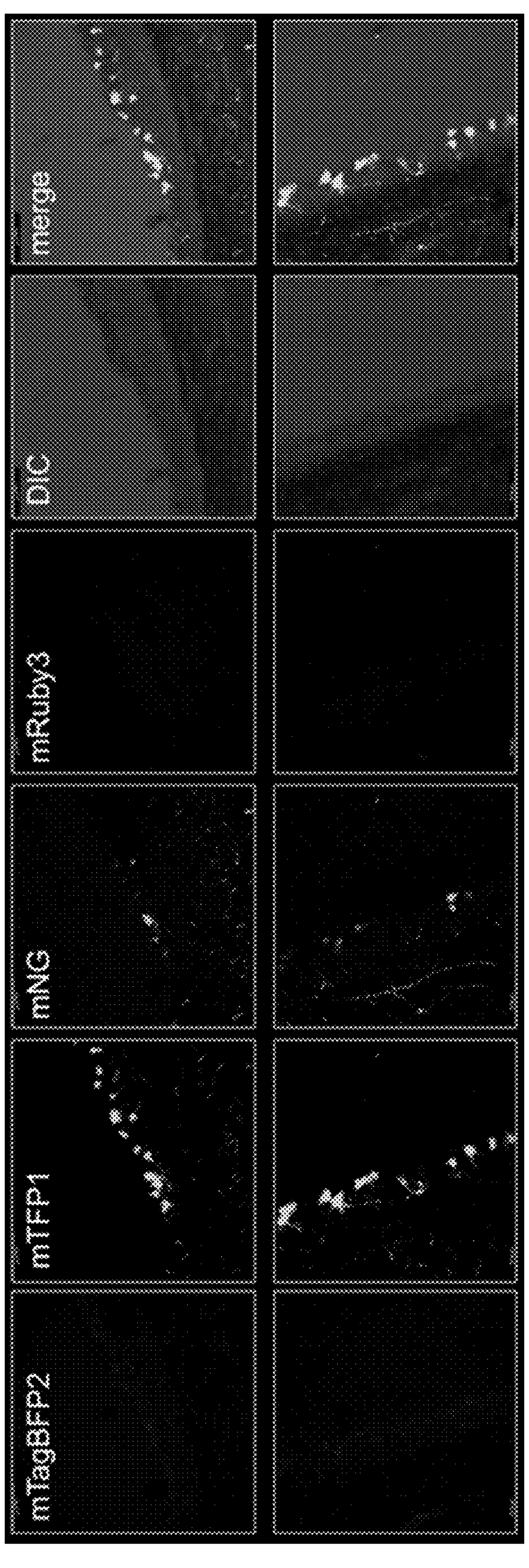
FIGS. 10A-C. Fluorescent images of AAV mixture in vivo Rhesus macaque lateral ventricle (A), fourth ventricle (B), and meninges (C).
Figure 10B:
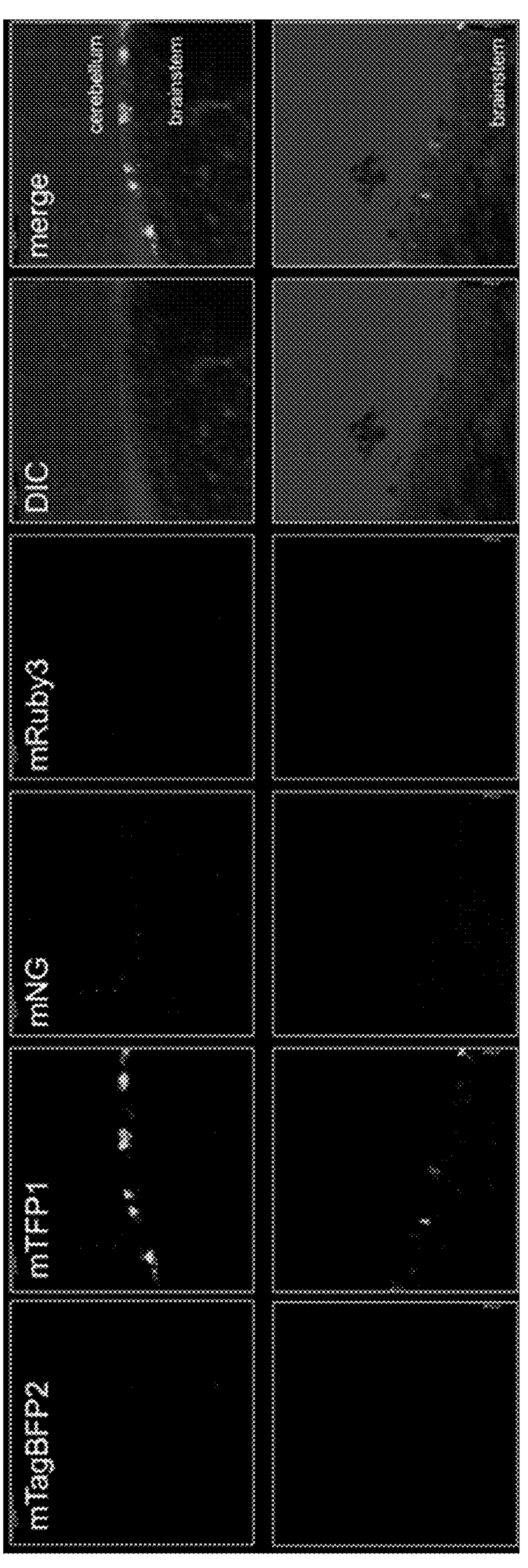
Figure 10C:
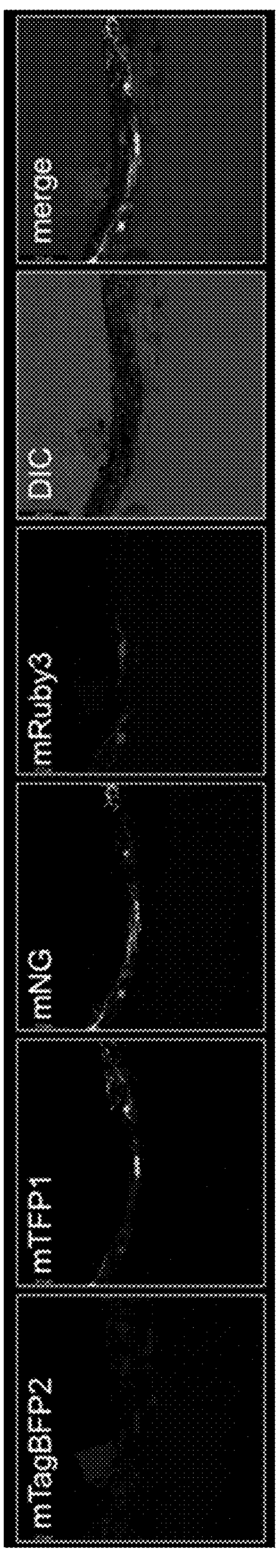

Brain was collected 30 days post-injection for fluorescence imaging. Lateral ventricle sections (FIG. 10A), fourth ventricle sections (FIG. 10B), and meninges sections (FIG. 10C) were imaged for mTagBFP2, mTFP2, mNG, and mRuby3 fluorescence signals.

Figure 11A:
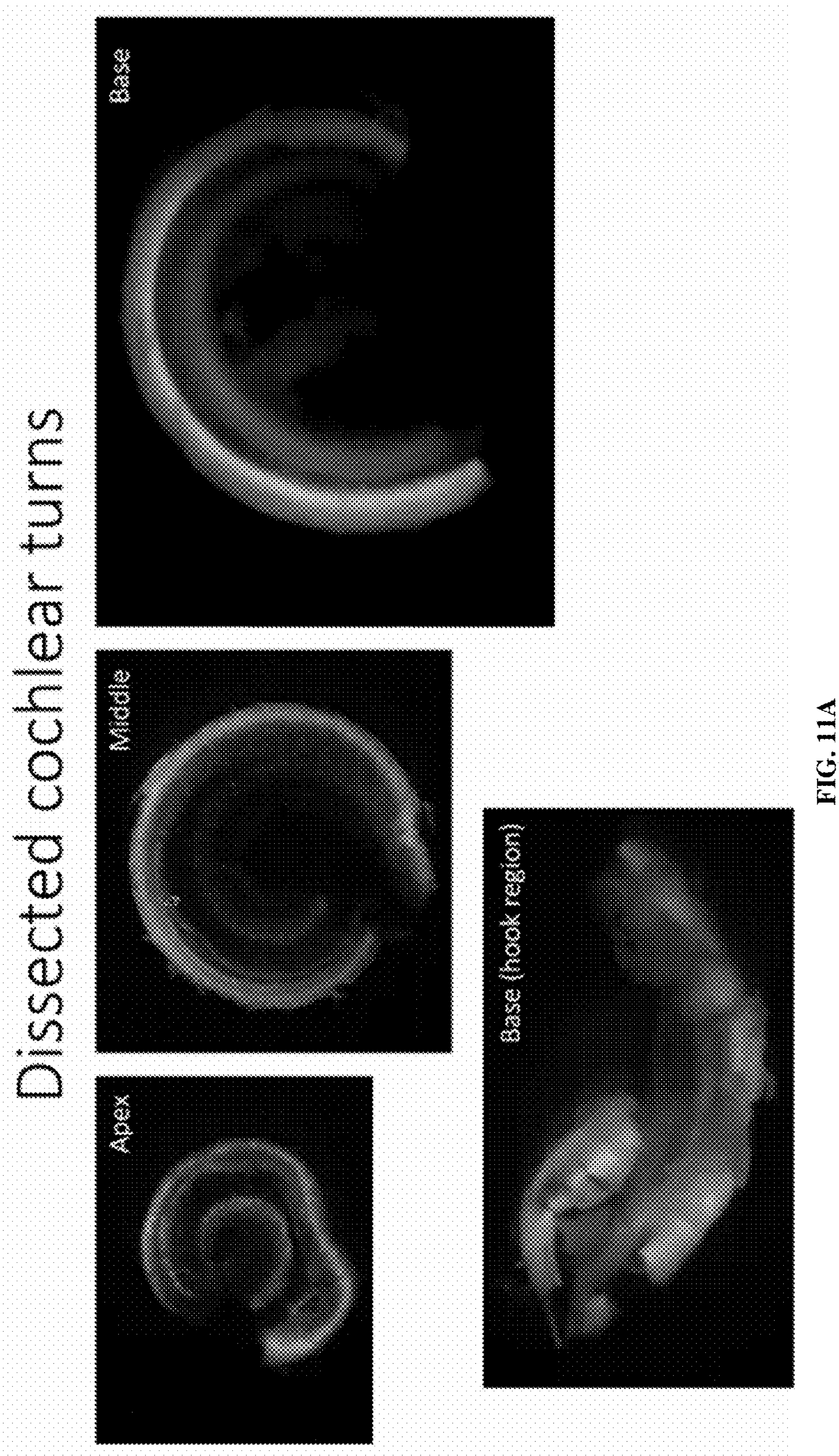
FIGS. 11A-C. Fluorescent images of cochlear turns (A), inner hair cells (B), organ of corti (C), and distal modiolus (C) following cochlear administration of AAV9 1999 capsids containing the eGFP construct to mice.
Figure 11B:
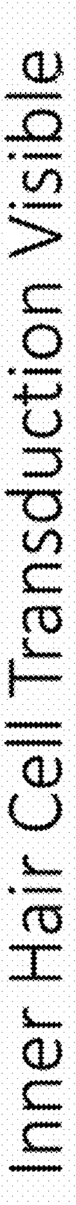
Figure 11B:
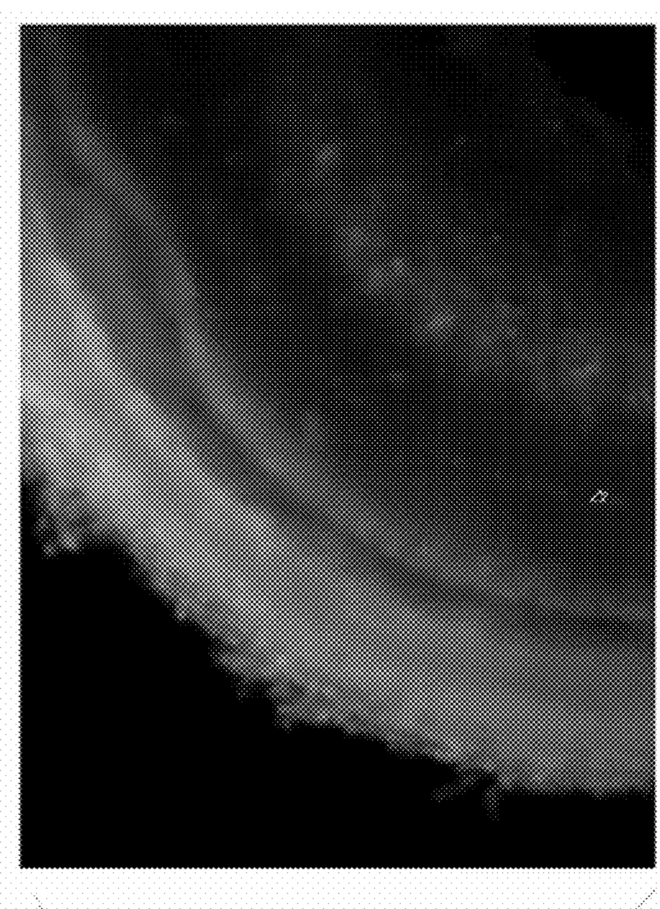
Figure 11B:
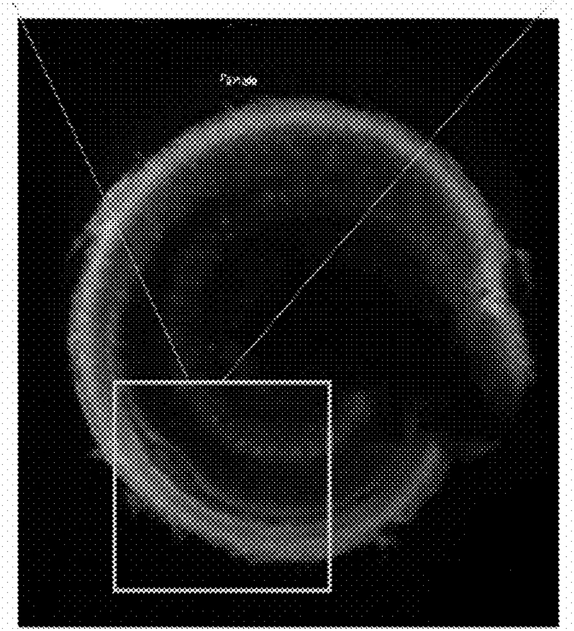
Figure 11C:
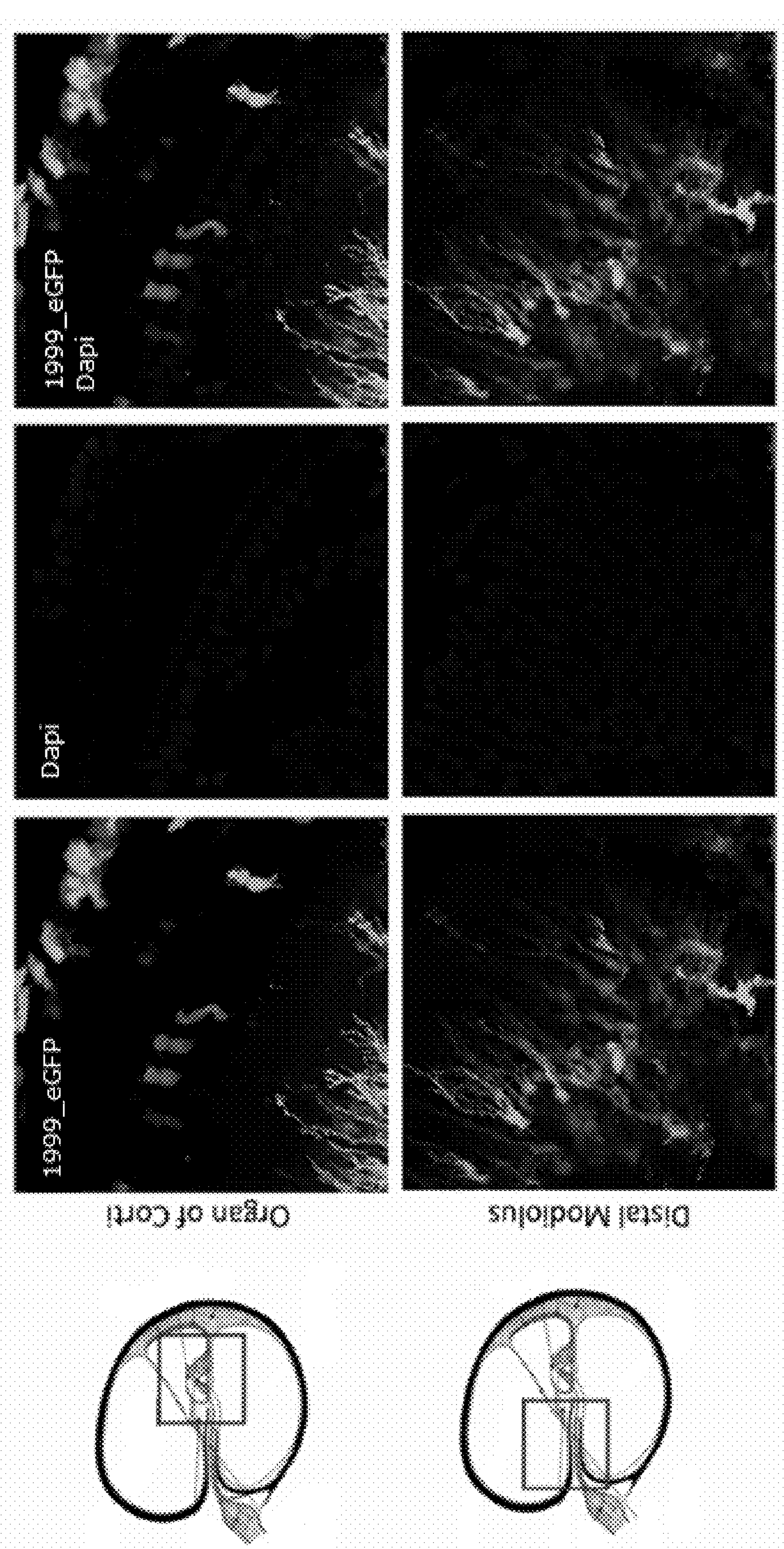

Additional experiments were performed by injecting the AAV9-1999 into the cochlea of rhesus macaques. Based on the results of cochlear transduction, an animal received AAV9-1999 to their lateral ventricle. A single animal received 3E11 vg of AAV9-1999 injected directly to their round window with canal fenestrations (FIGS. 11A-C).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 8,299,215

U.S. Pat. No. 8,691,948

United States Patent Application Publication No. 2018/0142259

Chen et al., Molecular signatures of disease brain endothelia provide new sites for CNS-directed enzyme therapy. Nat Med, 2009. 15(10): p. 1215-8.

Chen et al., Overcoming Limitations Inherent in Sulfamidase to Improve Mucopolysaccharidosis IIIA Gene Therapy. Mol Ther, 2018. 26(4): p. 1118-1126.

Deverman et al., Cre-dependent selection yields AAV variants for widespread gene transfer to the adult brain. Nat Biotechnol, 2016. 34(2): p. 204-9.

Hartz et al., Isolation of Cerebral Capillaries from Fresh Human Brain Tissue. J Vis Exp, 2018(139).

Hordeaux et al., The Neurotropic Properties of AAV-PHP.B Are Limited to C57BL/6J Mice. Mol Ther, 2018. 26(3): p. 664-668.

Katz et al., AAV gene transfer delays disease onset in a TPP1-deficient canine model of the late infantile form of Batten disease. Sci Transl Med, 2015. 7(313): p. 313ra180.

Keiser et al., Broad distribution of ataxin 1 silencing in rhesus cerebella for spinocerebellar ataxia type 1 therapy. Brain, 2015. 138(Pt 12): p. 3555-66.

Koerber et al., DNA shuffling of adeno-associated virus yields functionally diverse viral progeny. Mol Ther, 2008. 16(10): p. 1703-9.

Matsuzaki et al., Intravenous administration of the adeno-associated virus-PHP.B capsid fails to upregulate transduction efficiency in the marmoset brain. Neurosci Lett, 2018. 665: p. 182-188.

McBride et al., Preclinical safety of RNAi-mediated HTT suppression in the rhesus macaque as a potential therapy for Huntington's disease. Mol Ther, 2011. 19(12): p. 2152-62.

Monteys et al., CRISPR/Cas9 Editing of the Mutant Huntingtin Allele In Vitro and In Vivo. Mol Ther, 2017. 25(1): p. 12-23.

Muller et al., Random peptide libraries displayed on adeno-associated virus to select for targeted gene therapy vectors. Nat Biotechnol, 2003. 21(9): p. 1040-6.

Schaffer & Maheshri, Directed evolution of AAV mutants for enhanced gene delivery. Conf Proc IEEE Eng Med Biol Soc, 2004. 5: p. 3520-3.

Zhong et al., Next generation of adeno-associated virus 2 vectors: point mutations in tyrosines lead to high-efficiency transduction at lower doses. Proc Natl Acad Sci USA, 2008. 105(22): p. 7827-32.

SEQUENCE LISTING

```
Sequence total quantity: 144
SEQ ID NO: 1            moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 1
RPGREQA                                                                  7

SEQ ID NO: 2            moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 2
RGVLVTT                                                                  7

SEQ ID NO: 3            moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 3
RPGRESA                                                                  7

SEQ ID NO: 4            moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 4
NESLKKK                                                                  7

SEQ ID NO: 5            moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 5
DKTRAGS                                                                  7

SEQ ID NO: 6            moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 6
TAKSKQA                                                                  7

SEQ ID NO: 7            moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 7
PVKKKDA                                                                  7
```

```
SEQ ID NO: 8             moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 8
GRETLKG                                                                    7

SEQ ID NO: 9             moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 9
PIPAGKK                                                                    7

SEQ ID NO: 10            moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 10
NVVRAGT                                                                    7

SEQ ID NO: 11            moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 11
KATANTR                                                                    7

SEQ ID NO: 12            moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 12
RDATRSS                                                                    7

SEQ ID NO: 13            moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 13
VPTKSPK                                                                    7

SEQ ID NO: 14            moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 14
AGVARSK                                                                    7

SEQ ID NO: 15            moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 15
RSRSEVL                                                                    7
```

```
SEQ ID NO: 16          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 16
EVKGKGK                                                       7

SEQ ID NO: 17          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 17
AKLNKSS                                                       7

SEQ ID NO: 18          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 18
NSVHNTA                                                       7

SEQ ID NO: 19          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 19
NVVRGGA                                                       7

SEQ ID NO: 20          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 20
NRLVAGG                                                       7

SEQ ID NO: 21          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 21
ERDRTRG                                                       7

SEQ ID NO: 22          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 22
VQGSKMK                                                       7

SEQ ID NO: 23          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 23
```

```
NSVRPLT                                                            7

SEQ ID NO: 24          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 24
NKIHANP                                                            7

SEQ ID NO: 25          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 25
TAPKSLK                                                            7

SEQ ID NO: 26          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 26
RDSTRQL                                                            7

SEQ ID NO: 27          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 27
NSVKSVL                                                            7

SEQ ID NO: 28          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 28
NVTIKSK                                                            7

SEQ ID NO: 29          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 29
VSLKERV                                                            7

SEQ ID NO: 30          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 30
DETSRLV                                                            7

SEQ ID NO: 31          moltype = AA  length = 7
FEATURE                Location/Qualifiers
REGION                 1..7
                       note = Synthetic polypeptide
source                 1..7
                       mol_type = protein
                       organism = synthetic construct
```

```
SEQUENCE: 31
DRLKGIV                                                                 7

SEQ ID NO: 32          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 32
SGVLVQR                                                                 7

SEQ ID NO: 33          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 33
SGTFVKA                                                                 7

SEQ ID NO: 34          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 34
NSIARPV                                                                 7

SEQ ID NO: 35          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 35
NRARAGE                                                                 7

SEQ ID NO: 36          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 36
ARHALGG                                                                 7

SEQ ID NO: 37          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 37
HSSRPVA                                                                 7

SEQ ID NO: 38          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 38
KTGTARL                                                                 7

SEQ ID NO: 39          moltype = AA  length = 7
FEATURE                Location/Qualifiers
REGION                 1..7
                       note = Synthetic polypeptide
source                 1..7
                       mol_type = protein
```

```
                        organism = synthetic construct
SEQUENCE: 39
VKALGRP                                                                      7

SEQ ID NO: 40           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 40
NDVRAKG                                                                      7

SEQ ID NO: 41           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 41
QGVLVVR                                                                      7

SEQ ID NO: 42           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 42
KQYAGSQ                                                                      7

SEQ ID NO: 43           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 43
TNRMALS                                                                      7

SEQ ID NO: 44           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 44
GITLGRL                                                                      7

SEQ ID NO: 45           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 45
AGIMVRV                                                                      7

SEQ ID NO: 46           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 46
KAAGRTV                                                                      7

SEQ ID NO: 47           moltype = AA  length = 7
FEATURE                 Location/Qualifiers
REGION                  1..7
                        note = Synthetic polypeptide
source                  1..7
```

```
                        mol_type = protein
                        organism = synthetic construct
SEQUENCE: 47
HVIRLPS                                                         7

SEQ ID NO: 48           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 48
SVASAKK                                                         7

SEQ ID NO: 49           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 49
TATPRKG                                                         7

SEQ ID NO: 50           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 50
TKTGLKL                                                         7

SEQ ID NO: 51           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 51
KGLRTPT                                                         7

SEQ ID NO: 52           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 52
LTSRTSP                                                         7

SEQ ID NO: 53           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 53
DDPSARR                                                         7

SEQ ID NO: 54           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 54
GEQDLRR                                                         7

SEQ ID NO: 55           moltype = AA  length = 7
FEATURE                 Location/Qualifiers
REGION                  1..7
                        note = Synthetic polypeptide
```

```
source                  1..7
                        mol_type = protein
                        organism = synthetic construct
SEQUENCE: 55
VSTALPR                                                                    7

SEQ ID NO: 56           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 56
RDDVPLR                                                                    7

SEQ ID NO: 57           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 57
TRVGTAG                                                                    7

SEQ ID NO: 58           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 58
SSSKTGS                                                                    7

SEQ ID NO: 59           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 59
SLSTGPK                                                                    7

SEQ ID NO: 60           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 60
VQGRQGG                                                                    7

SEQ ID NO: 61           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 61
RGASGAV                                                                    7

SEQ ID NO: 62           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 62
NARAQGV                                                                    7

SEQ ID NO: 63           moltype = AA  length = 7
FEATURE                 Location/Qualifiers
REGION                  1..7
```

```
                         note = Synthetic polypeptide
source                   1..7
                         mol_type = protein
                         organism = synthetic construct
SEQUENCE: 63
TSNRGQV                                                                   7

SEQ ID NO: 64            moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 64
AVRGGMA                                                                   7

SEQ ID NO: 65            moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 65
RGLDKGT                                                                   7

SEQ ID NO: 66            moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 66
KGVDLKP                                                                   7

SEQ ID NO: 67            moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 67
TAVREER                                                                   7

SEQ ID NO: 68            moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 68
GNAGITK                                                                   7

SEQ ID NO: 69            moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 69
SARAGAP                                                                   7

SEQ ID NO: 70            moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 70
SGEFVGR                                                                   7

SEQ ID NO: 71            moltype = AA  length = 7
FEATURE                  Location/Qualifiers
```

```
REGION                  1..7
                        note = Synthetic polypeptide
source                  1..7
                        mol_type = protein
                        organism = synthetic construct
SEQUENCE: 71
SGRKLEV                                                                    7

SEQ ID NO: 72           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 72
SARSGSV                                                                    7

SEQ ID NO: 73           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 73
ESTGRER                                                                    7

SEQ ID NO: 74           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 74
VTQSKGA                                                                    7

SEQ ID NO: 75           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 75
RGSGSAV                                                                    7

SEQ ID NO: 76           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 76
NARPVSA                                                                    7

SEQ ID NO: 77           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 77
TARGGGG                                                                    7

SEQ ID NO: 78           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 78
GRSASGS                                                                    7

SEQ ID NO: 79           moltype = AA  length = 7
```

-continued

```
FEATURE                Location/Qualifiers
REGION                 1..7
                       note = Synthetic polypeptide
source                 1..7
                       mol_type = protein
                       organism = synthetic construct
SEQUENCE: 79
KAQGVGG                                                                    7

SEQ ID NO: 80          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 80
GRGAPGG                                                                    7

SEQ ID NO: 81          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 81
VPGRTAG                                                                    7

SEQ ID NO: 82          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 82
ARGSGVN                                                                    7

SEQ ID NO: 83          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 83
SVRVGGQ                                                                    7

SEQ ID NO: 84          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 84
RAVPAGG                                                                    7

SEQ ID NO: 85          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 85
VMSSGKP                                                                    7

SEQ ID NO: 86          moltype = AA  length = 7
FEATURE                Location/Qualifiers
REGION                 1..7
                       note = Synthetic polypeptide
source                 1..7
                       mol_type = protein
                       organism = synthetic construct
SEQUENCE: 86
STPAPKS                                                                    7
```

```
SEQ ID NO: 87            moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 87
RGGAQVV                                                                 7

SEQ ID NO: 88            moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 88
KASGAGG                                                                 7

SEQ ID NO: 89            moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 89
TGTAGLK                                                                 7

SEQ ID NO: 90            moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 90
RSNAPQT                                                                 7

SEQ ID NO: 91            moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 91
EAQSHPR                                                                 7

SEQ ID NO: 92            moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 92
TKSLSSG                                                                 7

SEQ ID NO: 93            moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 93
AAGAKVM                                                                 7

SEQ ID NO: 94            moltype = AA  length = 7
FEATURE                  Location/Qualifiers
REGION                   1..7
                         note = Synthetic polypeptide
source                   1..7
                         mol_type = protein
                         organism = synthetic construct
SEQUENCE: 94
RGSTQVG                                                                 7
```

```
SEQ ID NO: 95           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 95
GRSTGMT                                                           7

SEQ ID NO: 96           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 96
RATSQST                                                           7

SEQ ID NO: 97           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 97
VGRSVGA                                                           7

SEQ ID NO: 98           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 98
GEGGGGR                                                           7

SEQ ID NO: 99           moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 99
TAAGGQR                                                           7

SEQ ID NO: 100          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 100
GRGGAAL                                                           7

SEQ ID NO: 101          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 101
VAPISKS                                                           7

SEQ ID NO: 102          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 102
```

```
APPVKLS                                                            7

SEQ ID NO: 103          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 103
HDGGASR                                                            7

SEQ ID NO: 104          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 104
RSGGAAV                                                            7

SEQ ID NO: 105          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 105
GSRAGVG                                                            7

SEQ ID NO: 106          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 106
KLSISGN                                                            7

SEQ ID NO: 107          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 107
GAVGGVK                                                            7

SEQ ID NO: 108          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 108
KNESGKV                                                            7

SEQ ID NO: 109          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 109
AGQLAGR                                                            7

SEQ ID NO: 110          moltype = AA  length = 7
FEATURE                 Location/Qualifiers
REGION                  1..7
                        note = Synthetic polypeptide
source                  1..7
                        mol_type = protein
                        organism = synthetic construct
```

```
SEQUENCE: 110
KGGGFHG                                                          7

SEQ ID NO: 111          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 111
RAKPGME                                                          7

SEQ ID NO: 112          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 112
GRDVTRS                                                          7

SEQ ID NO: 113          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 113
RGDLQWV                                                          7

SEQ ID NO: 114          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 114
GGDRTRG                                                          7

SEQ ID NO: 115          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 115
RGDLASV                                                          7

SEQ ID NO: 116          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 116
RDTTRNL                                                          7

SEQ ID NO: 117          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 117
KGGGVHG                                                          7

SEQ ID NO: 118          moltype = AA  length = 7
FEATURE                 Location/Qualifiers
REGION                  1..7
                        note = Synthetic polypeptide
source                  1..7
                        mol_type = protein
```

```
                        organism = synthetic construct
SEQUENCE: 118
RGDMYRV                                                                    7

SEQ ID NO: 119          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 119
RGDRPVS                                                                    7

SEQ ID NO: 120          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 120
RSDVGSL                                                                    7

SEQ ID NO: 121          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 121
AGVKPGR                                                                    7

SEQ ID NO: 122          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 122
RGDWPRG                                                                    7

SEQ ID NO: 123          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 123
GGRPGSW                                                                    7

SEQ ID NO: 124          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 124
RGDYPRS                                                                    7

SEQ ID NO: 125          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 125
RGDLRFI                                                                    7

SEQ ID NO: 126          moltype = AA  length = 7
FEATURE                 Location/Qualifiers
REGION                  1..7
                        note = Synthetic polypeptide
source                  1..7
```

```
                      mol_type = protein
                      organism = synthetic construct
SEQUENCE: 126
RGGGVYG                                                                    7

SEQ ID NO: 127        moltype = AA  length = 7
FEATURE               Location/Qualifiers
REGION                1..7
                      note = Synthetic polypeptide
source                1..7
                      mol_type = protein
                      organism = synthetic construct
SEQUENCE: 127
GADRTRG                                                                    7

SEQ ID NO: 128        moltype = AA  length = 7
FEATURE               Location/Qualifiers
REGION                1..7
                      note = Synthetic polypeptide
source                1..7
                      mol_type = protein
                      organism = synthetic construct
SEQUENCE: 128
RGDFMGL                                                                    7

SEQ ID NO: 129        moltype = AA  length = 7
FEATURE               Location/Qualifiers
REGION                1..7
                      note = Synthetic polypeptide
source                1..7
                      mol_type = protein
                      organism = synthetic construct
SEQUENCE: 129
RRDETRT                                                                    7

SEQ ID NO: 130        moltype = AA  length = 7
FEATURE               Location/Qualifiers
REGION                1..7
                      note = Synthetic polypeptide
source                1..7
                      mol_type = protein
                      organism = synthetic construct
SEQUENCE: 130
AESPWER                                                                    7

SEQ ID NO: 131        moltype = AA  length = 7
FEATURE               Location/Qualifiers
REGION                1..7
                      note = Synthetic polypeptide
source                1..7
                      mol_type = protein
                      organism = synthetic construct
SEQUENCE: 131
AWDGTRV                                                                    7

SEQ ID NO: 132        moltype = AA  length = 7
FEATURE               Location/Qualifiers
REGION                1..7
                      note = Synthetic polypeptide
source                1..7
                      mol_type = protein
                      organism = synthetic construct
SEQUENCE: 132
ARGDGWR                                                                    7

SEQ ID NO: 133        moltype = AA  length = 7
FEATURE               Location/Qualifiers
REGION                1..7
                      note = Synthetic polypeptide
source                1..7
                      mol_type = protein
                      organism = synthetic construct
SEQUENCE: 133
GRDYTRL                                                                    7

SEQ ID NO: 134        moltype = AA  length = 7
FEATURE               Location/Qualifiers
REGION                1..7
                      note = Synthetic polypeptide
```

```
source                  1..7
                        mol_type = protein
                        organism = synthetic construct
SEQUENCE: 134
RRGDAWS                                                             7

SEQ ID NO: 135          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 135
MDLTKAV                                                             7

SEQ ID NO: 136          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 136
MMGRPGR                                                             7

SEQ ID NO: 137          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 137
TGRPGVW                                                             7

SEQ ID NO: 138          moltype = AA  length = 736
FEATURE                 Location/Qualifiers
source                  1..736
                        mol_type = protein
                        organism = Adeno-associated dependoparvovirus A
SEQUENCE: 138
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ  120
AKKRVLEPLG LVEEGAKTAP GKKRPVEQSP QEPDSSSGIG KTGQQPAKKR LNFGQTGDSE  180
SVPDPQPLGE PPATPAAVGP TTMASGGGAP MADNNEGADG VGNASGNWHC DSTWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTTNDGV TTIANNLTST VQVFSDSEYQ LPYVLGSAHQ  360
GCLPPFPADV FMIPQYGYLT LNNGSQAVGR SSFYCLEYFP SQMLRTGNNF TFSYTFEEVP  420
FHSSYAHSQS LDRLMNPLID QYLYYLNRTQ NQSGSAQNKD LLFSRGSPAG MSVQPKNWLP  480
GPCYRQQRVS KTKTDNNNSN FTWTGASKYN LNGRESIINP GTAMASHKDD EDKFFPMSGV  540
MIFGKESAGA SNTALDNVMI TDEEEIKATN PVATERFGTV AVNFQSSSTD PATGDVHAMG  600
ALPGMVWQDR DVYLQGPIWA KIPHTDGHFH PSPLMGGFGL KNPPPQILIK NTPVPANPPA  660
EFSATKFASF ITQYSTGQVS VEIEWELQKE NSKRWNPEVQ YTSNYAKSAN VDFTVDNNGL  720
YTEPRPIGTR YLTRPL                                                   736

SEQ ID NO: 139          moltype = AA  length = 735
FEATURE                 Location/Qualifiers
source                  1..735
                        mol_type = protein
                        organism = Adeno-associated dependoparvovirus A
SEQUENCE: 139
MAADGYLPDW LEDTLSEGIR QWWKLKPGPP PPKPAERHKD DSRGLVLPGY KYLGPFNGLD  60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP VEPDSSSGTG KAGQQPARKR LNFGQTGDAD  180
SVPDPQPLGQ PPAAPSGLGT NTMATGSGAP MADNNEGADG VGNSSGNWHC DSTWMGDRVI  240
TTSTRTWALP TYNNHLYKQI SSQSGASNDN HYFGYSTPWG YFDFNRFHCH FSPRDWQRLI  300
NNNWGFRPKR LNFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFT FSYTFEDVPF  420
HSSYAHSQSL DRLMNPLIDQ YLYYLSRTNT PSGTTTQSRL QFSQAGASDI RDQSRNWLPG  480
PCYRQQRVSK TSADNNNSEY SWTGATKYHL NGRDSLVNPG PAMASHKDDE EKFFPQSGVL  540
IFGKQGSEKT NVDIEKVMIT DEEEIRTTNP VATEQYGSVS TNLQRGNRQA ATADVNTQGV  600
LPGMVWQDRD VYLQGPIWAK IPHTDGHFHP SPLMGGFGLK HPPPQILIKN TPVPANPSTT  660
FSAAKFASFI TQYSTGQVSV EIEWELQKEN SKRWNPEIQY TSNYNKSVNV DFTVDTNGVY  720
SEPRPIGTRY LTRNL                                                    735

SEQ ID NO: 140          moltype = AA  length = 736
FEATURE                 Location/Qualifiers
source                  1..736
```

```
                         mol_type = protein
                         organism = Adeno-associated dependoparvovirus A
SEQUENCE: 140
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAQ AQTGWVQNQG  600
ILPGMVWQDR DVYLQGPIWA KIPHTDGNFH PSPLMGGFGM KHPPPQILIK NTPVPADPPT  660
AFNKDKLNSF ITQYSTGQVS VEIEWELQKE NSKRWNPEIQ YTSNYYKSNN VEFAVNTEGV  720
YSEPRPIGTR YLTRNL                                                  736

SEQ ID NO: 141           moltype = AA  length = 748
FEATURE                  Location/Qualifiers
REGION                   1..748
                         note = Synthetic polypeptide
VARIANT                  594..600
                         note = X is any amino acid
source                   1..748
                         mol_type = protein
                         organism = synthetic construct
SEQUENCE: 141
MAADGYLPDW LEDNLSEGIR EWWDLKPGAP KPKANQQKQD DGRGLVLPGY KYLGPFNGLD  60
KGEPVNAADA AALEHDKAYD QQLKAGDNPY LRYNHADAEF QERLQEDTSF GGNLGRAVFQ  120
AKKRVLEPLG LVEEGAKTAP GKKRPVEQSP QEPDSSSGIG KTGQQPAKKR LNFGQTGDSE  180
SVPDPQPLGE PPATPAAVGP TTMASGGGAP MADNNEGADG VGNASGNWHC DSTWLGDRVI  240
TTSTRTWALP TYNNHLYKQI SSASTGASND NHYFGYSTPW GYFDFNRFHC HFSPRDWQRL  300
INNNWGFRPK RLNFKLFNIQ VKEVTTNDGV TTIANNLTST VQVFSDSEYQ LPYVLGSAHQ  360
GCLPPFPADV FMIPQYGYLT LNNGSQAVGR SSFYCLEYFP SQMLRTGNNF TFSYTFEEVP  420
FHSSYAHSQS LDRLMNPLID QYLYYLNRTQ NQSGSAQNKD LLFSRGSPAG MSVQPKNWLP  480
GPCYRQQRVS KTKTDNNNSN FTWTGASKYN LNGRESIINP GTAMASHKDD EDKFFPMSGV  540
MIFGKESAGA SNTALDNVMI TDEEEIKATN PVATERFGTV AVNFQSSSTD SSAXXXXXXX  600
ASPATGDVHA MGALPGMVWQ DRDVYLQGPI WAKIPHTDGH FHPSPLMGGF GLKNPPPQIL  660
IKNTPVPANP PAEFSATKFA SFITQYSTGQ VSVEIEWELQ KENSKRWNPE VQYTSNYAKS  720
ANVDFTVDNN GLYTEPRPIG TRYLTRPL                                     748

SEQ ID NO: 142           moltype = AA  length = 747
FEATURE                  Location/Qualifiers
REGION                   1..747
                         note = Synthetic polypeptide
VARIANT                  591..597
                         note = X is any amino acid
source                   1..747
                         mol_type = protein
                         organism = synthetic construct
SEQUENCE: 142
MAADGYLPDW LEDTLSEGIR QWWKLKPGPP PPKPAERHKD DSRGLVLPGY KYLGPFNGLD  60
KGEPVNEADA AALEHDKAYD RQLDSGDNPY LKYNHADAEF QERLKEDTSF GGNLGRAVFQ  120
AKKRVLEPLG LVEEPVKTAP GKKRPVEHSP VEPDSSSGTG KAGQQPARKR LNFGQTGDAD  180
SVPDPQPLGQ PPAAPSGLGT NTMATGSGAP MADNNEGADG VGNSSGNWHC DSTWMGDRVI  240
TTSTRTWALP TYNNHLYKQI SSQSGASNDN HYFGYSTPWG YFDFNRFHCH FSPRDWQRLI  300
NNNWGFRPKR LNFKLFNIQV KEVTQNDGTT TIANNLTSTV QVFTDSEYQL PYVLGSAHQG  360
CLPPFPADVF MVPQYGYLTL NNGSQAVGRS SFYCLEYFPS QMLRTGNNFT FSYTFEDVPF  420
HSSYAHSQSL DRLMNPLIDQ YLYYLSRTNT PSGTTTQSRL QFSQAGASDI RDQSRNWLPG  480
PCYRQQRVSK TSADNNNSEY SWTGATKYHL NGRDSLVNPG PAMASHKDDE EKFFPQSGVL  540
IFGKQGSEKT NVDIEKVMIT DEEEIRTTNP VATEQYGSVS TNLQRGNAAA XXXXXXXAAR  600
QAATADVNTQ GVLPGMVWQD RDVYLQGPIW AKIPHTDGHF HPSPLMGGFG LKHPPPQILI  660
KNTPVPANPS TTFSAAKFAS FITQYSTGQV SVEIEWELQK ENSKRWNPEI QYTSNYNKSV  720
NVDFTVDTNG VYSEPRPIGT RYLTRNL                                      747

SEQ ID NO: 143           moltype = AA  length = 748
FEATURE                  Location/Qualifiers
REGION                   1..748
                         note = Synthetic polypeptide
VARIANT                  592..598
                         note = X is any amino acid
source                   1..748
                         mol_type = protein
                         organism = synthetic construct
SEQUENCE: 143
MAADGYLPDW LEDNLSEGIR EWWALKPGAP QPKANQQHQD NARGLVLPGY KYLGPGNGLD  60
KGEPVNAADA AALEHDKAYD QQLKAGDNPY LKYNHADAEF QERLKEDTSF GGNLGRAVFQ  120
AKKRLLEPLG LVEEAAKTAP GKKRPVEQSP QEPDSSAGIG KSGAQPAKKR LNFGQTGDTE  180
SVPDPQPIGE PPAAPSGVGS LTMASGGGAP VADNNEGADG VGSSSGNWHC DSQWLGDRVI  240
```

-continued

```
TTSTRTWALP TYNNHLYKQI SNSTSGGSSN DNAYFGYSTP WGYFDFNRFH CHFSPRDWQR  300
LINNNWGFRP KRLNFKLFNI QVKEVTDNNG VKTIANNLTS TVQVFTDSDY QLPYVLGSAH  360
EGCLPPFPAD VFMIPQYGYL TLNDGSQAVG RSSFYCLEYF PSQMLRTGNN FQFSYEFENV  420
PFHSSYAHSQ SLDRLMNPLI DQYLYYLSKT INGSGQNQQT LKFSVAGPSN MAVQGRNYIP  480
GPSYRQQRVS TTVTQNNNSE FAWPGASSWA LNGRNSLMNP GPAMASHKEG EDRFFPLSGS  540
LIFGKQGTGR DNVDADKVMI TNEEEIKTTN PVATESYGQV ATNHQSAQAA AXXXXXXXAS  600
AQAQTGWVQN QGILPGMVWQ DRDVYLQGPI WAKIPHTDGN FHPSPLMGGF GMKHPPPQIL  660
IKNTPVPADP PTAFNKDKLN SFITQYSTGQ VSVEIEWELQ KENSKRWNPE IQYTSNYYKS  720
NNVEFAVNTE GVYSEPRPIG TRYLTRNL                                    748

SEQ ID NO: 144          moltype = AA  length = 7
FEATURE                 Location/Qualifiers
REGION                  1..7
                        note = Synthetic polypeptide
source                  1..7
                        mol_type = protein
                        organism = synthetic construct
SEQUENCE: 144
RPGREAS                                                           7
```

What is claimed is:

1. A modified adeno-associated virus (AAV) capsid protein comprising a targeting peptide that targets a viral vector comprising the modified AAV capsid protein to a distinct organ or brain structure, wherein the targeting peptide comprises the amino acid sequence of SEQ ID NO: 21, wherein the modified AAV capsid protein is a modified AAV1 capsid protein having an amino acid sequence at least 95% identical to the amino acid sequence of SEQ ID NO: 138 and the targeting peptide is inserted after residue 590 of the amino acid sequence of SEQ ID NO: 138.

2. The modified AAV capsid protein of claim 1, wherein the distinct brain structure is the brainstem, caudate, cerebellar, cochlea (ear), cortex, cerebral cortex, deep cerebellar nuclei, ependyma, globus pallidus, hippocampus, meninges, motor cortex, optic nerve, prefrontal cortex, putamen, spinal cord, substantia nigra, subthalamic nuclei, temporal cortex, thalamus, or visual cortex.

3. The modified AAV capsid protein of claim 1, wherein the modified AAV capsid protein comprises an AAV1 capsid protein comprising the amino acid sequence of SEQ ID NO: 138.

4. The modified AAV capsid protein of claim 3, wherein the targeting peptide is flanked by linker sequences.

5. The modified AAV capsid protein of claim 4, wherein the linker sequences are SSA on the N-terminal side of the targeting peptide and AS on the C-terminal side of the targeting peptide.

6. The modified AAV capsid protein of claim 5, wherein the modified AAV1 capsid protein has an amino acid sequence at least 95% identical to the amino acid sequence of SEQ ID NO: 141.

7. The modified AAV capsid protein of claim 1, wherein the targeting peptide consists of the amino acid sequence of SEQ ID NO: 21.

8. The modified AAV capsid protein of claim 1, wherein the distinct brain structure is the brainstem, caudate, cerebellar cortex, cerebral cortex, ependyma, globus pallidus, hippocampus, meninges, optic nerve, putamen, spinal cord, substantia nigra, subthalamic nuclei, or thalamus.

9. The modified AAV capsid protein of claim 4, wherein the linker sequences on each side of the targeting peptide are two or three amino acids long.

10. A recombinant adeno-associated virus (rAAV) comprising the modified AAV1 capsid protein of claim 6.

11. The rAAV of claim 10, wherein the modified AAV1 capsid protein has an amino acid sequence at least 96% identical to the amino acid sequence of SEQ ID NO: 141.

12. The rAAV of claim 10, wherein the modified AAV1 capsid protein has an amino acid sequence at least 97% identical to the amino acid sequence of SEQ ID NO: 141.

13. The rAAV of claim 10, wherein the modified AAV1 capsid protein has an amino acid sequence at least 98% identical to the amino acid sequence of SEQ ID NO: 141.

14. The rAAV of claim 10, wherein the modified AAV1 capsid protein has an amino acid sequence at least 99% identical to the amino acid sequence of SEQ ID NO: 141.

15. A recombinant adeno-associated virus (rAAV) comprising the modified AAV1 capsid protein of claim 7.

16. A pharmaceutical composition comprising the rAAV of any one of claims 10-15 and a pharmaceutically acceptable carrier.

17. An in vitro cell comprising the rAAV of any one of claims 10-15.

18. The cell of claim 17, wherein the cell is a mammalian cell.

19. The cell of claim 18, wherein the mammalian cell is a human cell.

* * * * *